US012709734B2

(12) United States Patent
Martinez Arias et al.

(10) Patent No.: US 12,709,734 B2
(45) Date of Patent: Aug. 18, 2026

(54) HUMAN POLARISED THREE-DIMENSIONAL CELLULAR AGGREGATES

(71) Applicant: CAMBRIDGE ENTERPRISE LIMITED, Cambridgeshire (GB)

(72) Inventors: Alfonso Martinez Arias, Cambridgeshire (GB); Naomi Moris, Cambridgeshire (GB)

(73) Assignee: Cambridge Enterprise Limited, Cambridge (GB)

( * ) Notice: Subject to any disclaimer, the term of this patent is extended or adjusted under 35 U.S.C. 154(b) by 442 days.

(21) Appl. No.: 17/277,195

(22) PCT Filed: Sep. 23, 2019

(86) PCT No.: PCT/GB2019/052670

§ 371 (c)(1),
(2) Date: Mar. 17, 2021

(87) PCT Pub. No.: WO2020/058733

PCT Pub. Date: Mar. 26, 2020

(65) Prior Publication Data

US 2021/0348121 A1 Nov. 11, 2021

(30) Foreign Application Priority Data

Sep. 21, 2018 (GB) ..................................... 1815439

(51) Int. Cl.

| | |
|---|---|
| ***C12N 5/00*** | (2006.01) |
| ***C12N 5/071*** | (2010.01) |
| ***C12N 5/0735*** | (2010.01) |
| ***C12N 5/074*** | (2010.01) |

(52) U.S. Cl.

CPC ......... *C12N 5/0062* (2013.01); *C12N 5/0606* (2013.01); *C12N 5/0696* (2013.01); *C12N 5/0697* (2013.01); *C12N 2501/15* (2013.01); *C12N 2501/155* (2013.01); *C12N 2501/16* (2013.01); *C12N 2501/415* (2013.01); *C12N 2513/00* (2013.01)

(58) Field of Classification Search

CPC .. C12N 5/0062; C12N 5/0606; C12N 5/0696; C12N 5/0697; C12N 2501/15; C12N 2501/155; C12N 2501/16; C12N 2501/415; C12N 2513/00

See application file for complete search history.

(56) References Cited

FOREIGN PATENT DOCUMENTS

| | | |
|---|---|---|
| EP | 2716751 | 4/2014 |
| IN | 201647007612 | 7/2016 |
| WO | 2005005621 | 1/2005 |
| WO | 2013166488 | 11/2013 |

OTHER PUBLICATIONS

Etoc, F., et al., "A Balance between Secreted Inhibitors and Edge Sensing Controls Gastruloid Self-Organization," Developmental Cell 39(3): 302-315. doi: 10.1016/j.devcel.2016.09.016. Epub Oct. 13, 2016. (Year: 2016).*

Zhang, X., et al., "CellMarker: a manually curated resource of cell markers in human and mouse," Nucleic Acids Research 47(D1): D721-D728. doi: 10.1093/nar/gky900. Published online Oct. 5, 2018 (Year: 2018).*

Xue, X., et al., "Mechanics-guided embryonic patterning of neuroectoderm tissue from human pluripotent stem cells," Nature Materials 17(7): 633-641. doi: 10.1038/s41563-018-0082-9. Epub May 21, 2018. (Year: 2018).*

Deschamps, J., and Duboule, D., "Embryonic timing, axial stem cells, chromatin dynamics, and the Hox clock," Genes & Development 31(14): 1406-1416. doi: 10.1101/gad.303123.117. (Year: 2017).*

Heemskerk, I., and Warmflash, A., "Pluripotent stem cells as a model for embryonic patterning: From signaling dynamics to spatial organization in a dish," Developmental Dynamics 245(10): 976-990 (2016). doi: 10.1002/dvdy.24432. Epub Aug. 25, 2016. (Year: 2016).*

Saito, S., and Suzuki, T., "How do signaling and transcription factors regulate both axis elongation and Hox gene expression along the anteroposterior axis?" Dev Growth Differ 62(5): 363-375. doi: 10.1111/dgd.12682. Epub Jun. 12, 2020. (Year: 2020).*

Chen, D., et al., "Human Primordial Germ Cells Are Specified from Lineage-Primed Progenitors," Cell Rep. 29(13): 4568-4582.e5. doi: 10.1016/j.celrep.2019.11.083. (Year: 2019).*

Aulehla, A., and Pourquie, O., "Signaling gradients during paraxial mesoderm development," Cold Spring Harb Perspect Biol 2(2): a000869. doi: 10.1101/cshperspect.a000869. (Year: 2010).*

Kurosawa, H., "Application of Rho-associated protein kinase (ROCK) inhibitor to human pluripotent stem cells," J Biosci Bioeng 114(6): 577-581. doi: 10.1016/j.jbiosc.2012.07.013. (Year: 2013).*

Munteanu, O., et al., "The etiopathogenic and morphological spectrum of anencephaly: a comprehensive review of literature," Rom J Morphol Embryol 61(2): 335-343. doi: 10.47162/RJME.61.2.03. (Year: 2020).*

Heemskerk, I., and Warmflash, A., "Pluripotent stem cells as a model for embryonic patterning: From signaling dynamics to spatial organization in a dish," Dev Dyn 245(10): 976-990. doi: 10.1002/dvdy.24432 (Year: 2016).*

Yu, J., et al., "Reduced H3K27me3 leads to abnormal Hox gene expression in neural tube defects," Epigenetics Chromatin 12(1):76. doi: 10.1186/s13072-019-0318-1. (Year: 2019).*

Tepekoy, F., et al., "The role of Wnt signaling members in the uterus and embryo during pre-implantation and implantation," J Assist Reprod Genet 32(3):337-346. doi: 10.1007/s10815-014-0409-7. Epub Dec. 24, 2014. (Year: 2014).*

(Continued)

*Primary Examiner* — Tracy Vivlemore
*Assistant Examiner* — Eric J Rogers
(74) *Attorney, Agent, or Firm* — Brian E. Davy; Bozicevic, Field & Francis LLP

(57) ABSTRACT

Human polarised three-dimensional cellular aggregates generated in vitro from one or more human pluripotent stem cells are provided. Methods for obtaining human polarised three-dimensional cellular aggregates and cells obtained from the human polarised three-dimensional cellular aggregates are also provided.

17 Claims, 53 Drawing Sheets

(56) References Cited

OTHER PUBLICATIONS

Malinska, N., et al., "Maternal-Fetal Microchimerism: Impacts on Offspring's Immune Development and Transgenerational Immune Memory Transfer," Physiol Res 73(3): 315-332. doi: 10.33549/physiolres.935296. (Year: 2024).*
Deglincerti et al. (2016) "Self-organization of human embryonic stem cells on micropatterns" Nature Protocols, 11(11):2223-2232.
Etoc et al. (2016) "A Balance between Secreted Inhibitors and Edge Sensing Controls Gastruloid Self-Organization" Developmental Cell, 39(3):302-315.
International Preliminary Report on Patentability dated Apr. 1, 2021, Appl. No. PCT/GB2019/052670, 8 pp.
Shao et al. (2017) "A pluripotent stem cell-based model for post-implantation human amniotic sac development" Nature Communications, 8:208, 15 pp.
Siggia et al. (2018) "Modeling Mammalian Gastrulation with Embryonic Stem Cells" Current Topics In Developmental Biology, 129:1-23.
Simunovic et al. (2017) "Embryoids, organoids and gastruloids: new approaches to understanding embryogenesis" Development, 144(6):976-985.
Turner et al. (2017) "Anteroposterior polarity and elongation in the absence of extra-embryonic tissues and of spatially localised signalling in gastruloids: mammalian embryonic organoids" Development, 144(21):3894-3906.
Barrett et al. (2006) "Response preferences for "what" and "where" in human non-primary auditory cortex" Neurolmage, 32:968-977.
Lin et al. (2016) "Adipose-derived stem cells mediate immunosuppression of Th17 in multiple sclerosis" Chinese Journal of Pathophysiology, 32(1):51-57.
Office Action and Search Report (English Translation) dated Dec. 1, 2023, Appl. No. CN 201980076517.X, 9 pp.
Examination Report dated Nov. 29, 2024, Appl. No. EP 19778622.1, 5 pp.
Third Office Action (English Translation) dated Oct. 30, 2024, Appl. No. CN 201980076517.X, 5 pp.
Warmflash et al. (2014) "A method to recapitulate early embryonic spatial patterning in human embryonic stem cells" Nat Methods. 11(8): 847-854.
Office Action (English Translation) dated Apr. 25, 2024, Appl. No. CN 201980076517.X, 9 pp.
Amel et al. (2022) "Gastruloids: A Novel System for Disease Modelling and Drug Testing" Stem Cell Reviews and Reports, 10 pages.
Moris et al. (2020) "An in vitro model of early anteroposterior organization during human development" Nature, 24 pages.

* cited by examiner a
Anterior
Posterior
b
transcripts
sections
genes
sections
c
relative expression (a.u.)
sections
d
Anterior
Central
Peaked
Posterior
GATA6
ID2
IRX3
TBX1
TCF15
PAX3
MEOX1
FST
MESP1
MESP2
MSX1
DLL1
BRA
CDX2
MNX1
CHRD
Relative Gene Expression (a.u.)
Section (#) Anterior-Posterior e d MasterShef 7: 72h 1.5 μM Chi PT 0 μM Chi 0.5 μM Chi 3 μM Chi 48h 72h 96h 3 μM Chi PT 0 μM Chi 0.5 μM Chi 3 μM Chi 48h 72h 96h 5 μM Chi PT 0 μM Chi 0.5 μM Chi 3 μM Chi 48h 72h 96h RUES2-GLR: 72h 3 μM Chi PT 0.5 μM Chi 3.25 μM Chi PT 0.5 μM Chi 3.5 μM Chi PT 0.5 μM Chi 4 μM Chi PT 0.5 μM Chi

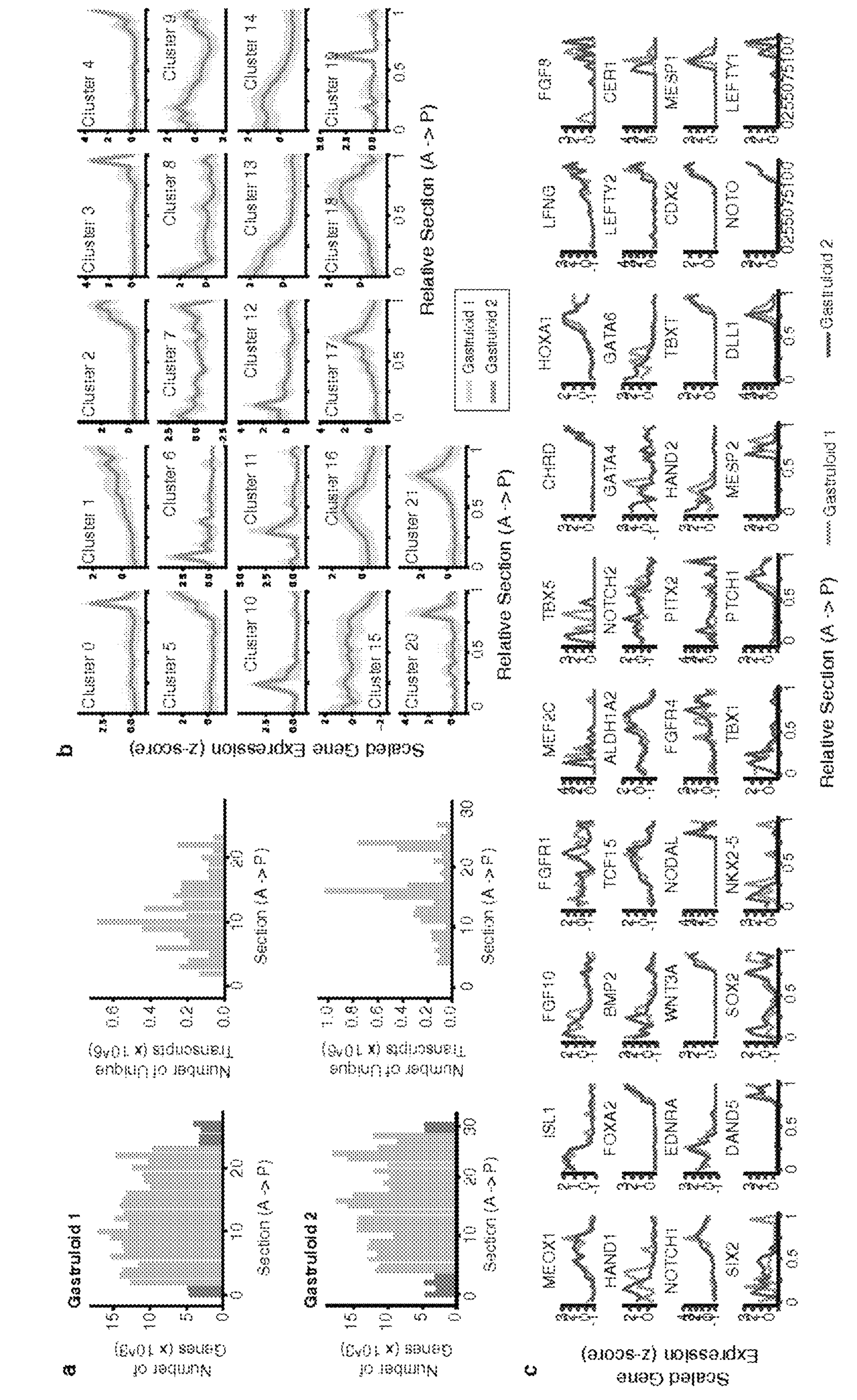

FIG. 16 a

Gastruloid 1

Gastruloid 2

Number of Genes (x 10^3)

Number of Unique Transcripts (x 10^6)

Section (A -> P)

b

Scaled Gene Expression (z-score)

Cluster 0 Cluster 1 Cluster 2 Cluster 3 Cluster 4

Cluster 5 Cluster 6 Cluster 7 Cluster 8 Cluster 9

Cluster 10 Cluster 11 Cluster 12 Cluster 13 Cluster 14

Cluster 15 Cluster 16 Cluster 17 Cluster 18 Cluster 19

Cluster 20 Cluster 21

Gastruloid 1

Gastruloid 2

Relative Section (A -> P)

c

Scaled Gene Expression (z-score)

MEOX1 ISL1 FGF10 FGFR1 MEF2C TBX5 CHRD HOXA1 LFNG FGF8

HAND1 FOXA2 BMP2 TCF15 ALDH1A2 NOTCH2 GATA4 GATA6 LEFTY2 CER1

NOTCH1 EDNRA WNT3A NODAL FGFR4 PITX2 HAND2 TBXT CDX2 MESP1

SIX2 DAND5 SOX2 NKX2-5 TBX1 PTCH1 MESP2 DLL1 NOTO LEFTY1

Relative Section (A -> P)

Gastruloid 1 Gastruloid 2 d e

HUMAN POLARISED THREE-DIMENSIONAL CELLULAR AGGREGATES

TECHNICAL FIELD

The present invention relates to human polarised three-dimensional cellular aggregates generated in vitro from one or more human pluripotent stem cells, methods for obtaining human polarised three-dimensional cellular aggregates and cells obtained from the human polarised three-dimensional cellular aggregates.

BACKGROUND

During development, the body-plan of a mammalian embryo emerges through a process known as 'gastrulation', which transforms an isotropic group of cells into an ensemble of tissues from all three germ layers (mesoderm, endoderm and neuroectoderm), arranged along the axes of the embryo. While model organisms have provided us with much insight into the processes that occur during early embryonic development, we know very little about similar stages in humans, due to obvious ethical and practical restrictions. Therefore, in vitro models are necessary to gain insight into the principles of the developing human body plan.

Recent advances with in vitro culture of human embryos have raised the possibility of probing the initial stages of human gastrulation. However, these studies are limited by technical challenges associated with keeping embryos alive and healthy during in vitro culture and by ethical regulations preventing culture beyond Day 14.

The derivation of human pluripotent stem cells (PSCs) from human embryos has opened up alternatives for functional studies of early cell fate decisions, particularly in adherent culture. In these conditions human PSCs differentiate in heterogeneous and heterochronic fashion that challenge attempts to understand the mechanisms underlying cell fate decisions as well as tissue and organ formation. Constraining the growth of human PSCs on micropatterned surfaces reduces these heterogeneities and leads to the emergence of complex patterns of gene expression that resemble the germ layer organization of the early mammalian embryo, with separate domains for ectoderm, endoderm and mesoderm (Warmflash et al., 2014). However, while the geometry of the micropatterns (a two-dimensional disc) resembles that of the human embryo, exposure to signals leads to radially symmetric patterns of gene expression rather than the multi-axial organization that is characteristic of embryos.

When mouse PSCs are aggregated under defined conditions in three dimensions, they generate 'gastruloids', an in vitro experimental system that exhibits an embryo-like spatiotemporal organization (Turner et al., 2014; Turner et al., 2017[1]; and van den Brink et al., 2014).

Growth of human ESCs in three-dimensions within the confines of artificial matrices leads, at a low frequency (<10%), to the emergence of structures resembling the amniotic sac, in which cells undergo initial gastrulation-like movements, including Bra expression and epithelial-to-mesenchymal transition (EMT), before collapsing (Shao et al., 2017). In addition, growth of human ESCs as gel-embedded cell mixtures have generated a 3D model of a human epiblast (Simunovic et a., 2018). While these methods have proved useful in understanding some of the principles of pregastrulation development in humans, they are notably distinct from the three-dimensional, axially organised and multilineage differentiated features of early embryos.

DESCRIPTION

The invention provides polarised three-dimensional cellular aggregates (or human gastruloids) generated in vitro from one or more human pluripotent stem cells, methods for obtaining polarised three-dimensional cellular aggregates and human cells (e.g. progenitor cells and derivatives thereof) obtained from the polarised three-dimensional cellular aggregates. Also provided are tissues and organs comprising human cells derived from the polarised three-dimensional cellular aggregates.

The polarised three-dimensional cellular aggregates derived from hPSCs (i.e. human gastruloids) have a wide range of applications including: Basic biology (understanding developmental events: gastrulation, specification of tissue and organ primordia, lineages and principles of gene regulatory networks); Cell type characterisation (combinatorial gene expression of rare and early cell types), Cell type generation (production of any of the derivatives of the 3 germ layers or primordial germ cells, for research or therapy); Mutant analysis and Disease modelling (patient-derived, patient-specific or through, for example, genetic knock-outs); An experimental system for the analysis of gene expression, epigenetic regulatory mechanisms and the molecular mechanisms underlying human development. Analysis of regulatory regions of genes; Drug screening; Toxicity assays (particularly in early development, or for multi-organ specificity/sensitivity analysis); Cell line validation (PSC validation assays replacing mouse teratoma assays or directed differentiation as a measure of pluripotency potential); IVF blastomere assessment (non-Genetic pre-natal screening); and the generation of functional cell types, organs and tissues for regenerative medicine.

The polarised three-dimensional cellular aggregates are, like embryos, dynamic entities. These entities have emergent, embryo-like characteristics, in that over time they exhibit sequences of the different combination of markers, gene expression patterns and morphological changes described herein.

The invention provides a polarised three-dimensional cellular aggregate generated in vitro from one or more human pluripotent stem cells, wherein:

(a) the polarised three-dimensional cellular aggregate comprises
  i. cells comprising one or more markers characteristic of endodermal cells or derivatives thereof,
  ii. cells comprising one or more markers characteristic of mesodermal cells or derivatives thereof, and
  iii. cells comprising one or more markers characteristic of ectodermal cells or derivatives thereof; and (b) the polarised three-dimensional cellular aggregate is polarised along the anterior-posterior axis, wherein the anterior-posterior axis is defined by at least an anterior region of cells and a posterior region of cells, and wherein the cells of the anterior region express a higher or lower level of one or more genes than the cells of the posterior region.

The invention provides a polarised three-dimensional cellular aggregate generated in vitro from one or more human pluripotent stem cells, wherein:

(a) the polarised three-dimensional cellular aggregate comprises cells comprising one or more markers characteristic of primordial germ cells or derivatives thereof; and (b) the polarised three-dimensional cellular aggregate is polarised along the anterior-posterior axis, wherein the anterior-posterior axis is defined by at least an anterior region of cells and a posterior region of cells, and wherein the cells of the anterior region express a higher or lower level of one or more genes than the cells of the posterior region.

The invention provides a polarised three-dimensional cellular aggregate generated in vitro from one or more human pluripotent stem cells, wherein:

(a) the polarised three-dimensional cellular aggregate comprises
  i. cells comprising one or more markers characteristic of endodermal cells or derivatives thereof,
  ii. cells comprising one or more markers characteristic of mesodermal cells or derivatives thereof,
  iii. cells comprising one or more markers characteristic of ectodermal cells or derivatives thereof, and
  iv. cells comprising one or more markers characteristic of primordial germ cells or derivatives thereof; and
(b) the polarised three-dimensional cellular aggregate is polarised along the anterior-posterior axis, wherein the anterior-posterior axis is defined by at least an anterior region of cells and a posterior region of cells, and wherein the cells of the anterior region express a higher or lower level of one or more genes than the cells of the posterior region.

The one or more markers may be gDNA, RNA, polypeptide or other molecules. Preferably, the one or more markers are genes the expression of which is characteristic of the specified cell type.

The polarised three-dimensional cellular aggregate may be polarised along the dorsal-ventral axis, wherein the dorsal-ventral axis is defined by at least a dorsal region of cells and a ventral region of cells, wherein the cells of the dorsal region express a higher or lower level of one or more genes than the cells of the ventral region.

The polarised three-dimensional cellular aggregate may be polarised along the medio-lateral, wherein the medio-lateral axis is defined by at least a medial region of cells and two lateral regions of cells, wherein the cells of the medial region express a higher or lower level of one or more genes than the cells of the lateral regions.

The polarised three-dimensional cellular aggregate may be polarised along the left-right axis, wherein the left-right axis is defined by at least a left region of cells and a right region of cells, wherein the cells of the left region express a higher or lower level of one or more genes than the cells of the right region.

The cells of the anterior region may express a lower level of one or more genes than the cells of the posterior region, and wherein the one or more genes are selected from BRA, WNT3a, CDX2, CDH2 (N-cadherin), BMP7, CHRD, CYP26A, DAND5, NOTO1, FOXA2, CER1, DLL1, DLL3, LEFTY1, LEFTY2, SHH and PTCH1. Preferably, the cells of the anterior region express a lower level of BRA than the cells of the posterior region.

The cells of the anterior region may express a higher level of one or more genes than the cells of the posterior region, and wherein the one or more genes are selected from GATA6, HAND2, PRDM1, TBX1, BMP2, CDH3, LHX1, PAX8 and BMP4. Preferably, the cells of the anterior region express a higher level of GATA6 than the cells of the posterior region.

The cells of the anterior region may express a lower level of BRA than the cells of the posterior region, and wherein the cells of the anterior region express a higher level of GATA6 than the cells of the posterior region.

The cells of the anterior region may express a lower level of BRA, WNT3A, CDX2, BMP7, CHRD, CYP26A1, DAND5, NOTO1, FOXA2, CER1, DLL1, DLL3, LEFTY1, LEFTY2, SHH and/or PTCH1 than the cells of the posterior region, and wherein the cells of the anterior region express a higher level of GATA6 than the cells of the posterior region.

The cells of the anterior region may express a lower level of BRA, WNT3A, CDX2, BMP7, CHRD, CYP26A1, DAND5, NOTO1, FOXA2, CER1, DLL1, DLL3, LEFTY1, LEFTY2, SHH and/or PTCH1 than the cells of the posterior region, and wherein the cells of the anterior region express a higher level of HAND2 than the cells of the posterior region.

The cells of the anterior region may express a lower level of BRA, WNT3A, CDX2, BMP7, CHRD, CYP26A1, DAND5, NOTO1, FOXA2, CER1, DLL1, DLL3, LEFTY1, LEFTY2, SHH and/or PTCH1 than the cells of the posterior region, and wherein the cells of the anterior region express a higher level of PRDM1 than the cells of the posterior region.

The cells of the anterior region may express a lower level of BRA, WNT3A, CDX2, BMP7, CHRD, CYP26A1, DAND5, NOTO1, FOXA2, CER1, DLL1, DLL3, LEFTY1, LEFTY2, SHH and/or PTCH1 than the cells of the posterior region, and wherein the cells of the anterior region express a higher level of TBX1 than the cells of the posterior region.

The cells of the anterior region may express a lower level of BRA, WNT3A, CDX2, BMP7, CHRD, CYP26A1, DAND5, NOTO1, FOXA2, CER1, DLL1, DLL3, LEFTY1, LEFTY2, SHH and/or PTCH1 than the cells of the posterior region, and wherein the cells of the anterior region express a higher level of BMP2 than the cells of the posterior region.

The cells of the posterior region may express BRA and wherein the polarised three-dimensional cellular aggregate comprises one or more SOX17-expressing cells, wherein optionally the SOX17-expressing cells are adjacent to the posterior region.

The cells of the posterior region may express BRA and wherein polarised three-dimensional cellular aggregate comprises a SOX2-expressing region, and wherein the SOX2-expressing region comprises SOX2-expressing cells. The SOX2-expressing region may be anterior to the posterior region. The SOX2-expressing region may be adjacent to the posterior region. The SOX2-expressing region may be overlapping with the posterior region.

The anterior region may consist of at least 2%, at least 5%, at least 10%, at least 15%, at least 20%, at least 25%, at least 30%, at least 35%, at least 40%, at least 45% or 50% of the polarised three-dimensional cellular aggregate. Preferably, the anterior region consists of at least 5% of the polarised three-dimensional cellular aggregate The posterior region may consist of at least 2%, at least 5%, at least 10%, at least 15%, at least 20%, at least 25%, at least 30%, at least 35%, at least 40%, at least 45% or 50% of the polarised three-dimensional cellular aggregate. Preferably, the posterior region consists of at least 5% of the polarised three-dimensional cellular aggregate.

The polarised three-dimensional cellular aggregate may comprise two or more of:

a. a region of cells expressing at least BRA,
b. a region of cells expressing at least SOX2,
c. a region of cells expressing at least TBX6,
d. a region of cells expressing at least MEOX1,
e. a region of cells expressing at least MESP2, f. a region of cells expressing at least TCF15;
g. a region of cells expressing at least GATA6; and
h. a region of cells expressing at least BMP2;
wherein (a)-(h) are arranged from posterior to anterior in the polarised three-dimensional cellular aggregate.

The polarised three-dimensional cellular aggregate may comprise:

a. a region of cells expressing at least BRA,
b. a region of cells expressing at least SOX2,
c. a region of cells expressing at least TBX6,
d. a region of cells expressing at least MEOX1,
e. a region of cells expressing at least MESP2,
f. a region of cells expressing at least TCF15;
g. a region of cells expressing at least GATA6; and
h. a region of cells expressing at least BMP2;
wherein (a)-(h) are arranged from posterior to anterior in the polarised three-dimensional cellular aggregate.

The polarised three-dimensional cellular aggregate may comprise a tail bud-like region of cells in the posterior region, optionally wherein the cells of the tail bud-like region of cells express one or more of BRA, CDX2, WNT3a, WNT5a, FGF8 and CYP26a1.

The polarised three-dimensional cellular aggregate may comprise a node-like structure. The node-like structure may comprise cells expressing one or more of NODAL, CER1, DAND5, BMP7. FOXA2, NOTO1, SHH, CDH1 and LEFTY1,2.

The anterior-posterior axis is further defined by a central region (or mid-gastruloid region as also referred to herein) of cells between the anterior region of cells and the posterior region of cells, wherein the cells of the central region express a higher or lower level of one or more genes than the cells of the anterior or posterior regions.

The cells of the central region express a higher level of one or more genes than the cells of the anterior or posterior regions, and wherein the one or more genes are selected from ALDH1A2, DKK1, MEOX1, MESP1, MESP2, OSR1, PITX2, TCF15, PAX3 and/or SIX1.

The cells of the central region express a higher level of one or more genes than the cells of the anterior or posterior regions, and wherein the one or more genes are selected from ALDH1A2, DKK1, MEOX1, MESP1, MESP2, OSR1, PITX2, TCF15, PAX3, UNCX, RIPPLY1, RIPPLY2 and/or SIX1

The central region may consist of at least 2%, at least 5%, at least 10%, at least 15%, at least 20%, at least 25%, at least 30%, at least 35%, at least 40%, at least 45% or 50% of the polarised three-dimensional cellular aggregate. Preferably, the central region consists of at least 5% of the polarised three-dimensional cellular aggregate.

The anterior-posterior axis may be further defined by a somitogenesis-like region of cells between the posterior region of cells and the central region of cells, wherein the cells of the somitogenesis-like region express a higher or lower level of one or more genes than the cells of the anterior, posterior or central regions. The cells of the somitogenesis-like region may express a higher level of one or more genes than the cells of the anterior, posterior or central regions, and wherein the one or more genes are selected from BRA, MSGN, DLL1, MESP1, TBX6, MEOX1, MESP1 and MESP2. The cells of the somitogenesis-like region may express a higher level of one or more genes than the cells of the anterior, posterior or central regions, and wherein the one or more genes are selected from BRA, MSGN, DLL1, TBX6, MEOX1, MESP1, MESP2, RIPPLY1, RIPPLY2, TCF15 and UNCX. The cells of the somitogenesis-like region may be selected from one or more of somite cells and precursors thereof, optionally wherein the precursors are one or more presomitic mesoderm cells.

The somitogenesis-like region may consist of at least 2%, at least 5%, at least 10%, at least 15%, at least 20%, at least 25%, at least 30%, at least 35%, at least 40%, at least 45% or 50% of the polarised three-dimensional cellular aggregate. Preferably, the somitogenesis-like region consists of at least 5% of the polarised three-dimensional cellular aggregate.

The anterior-posterior axis may be further defined by a node-like region of cells between the posterior region of cells and the central region of cells, wherein the cells of the node-like region express a higher or lower level of one or more genes than the cells of the anterior, posterior or central regions. The cells of the node-like region may express a higher level of one or more genes than the cells of the anterior, posterior or central regions, and wherein the one or more genes are selected from group 1 (i.e. BRA, MSGN, DLL1, MESP1, TBX6, MEOX1, MESP1 and MESP2). The cells of the node-like region may express a higher level of one or more genes than the cells of the anterior, posterior or central regions, and wherein the one or more genes are selected from group 2 (i.e. NODAL, CER1, DAND5, BMP7. FOXA2, NOTO1, SHH and LEFTY1,2.). The expression level of one or more genes of group 2 in the node-like region may be higher than the expression level of one or more genes of group 1 in the node-like region.

The node-like region may consist of at least 1%, at least 2%, at least 5%, at least 10%, at least 15%, at least 20%, at least 25%, at least 30%, at least 35%, at least 40%, at least 45% or 50% of the polarised three-dimensional cellular aggregate. Preferably, the node-like region consists of at least 1% of the polarised three-dimensional cellular aggregate.

The anterior-posterior axis may be further defined by a central-posterior region of cells between the central region of cells and the posterior region of cells, wherein the cells of the central-posterior region express a higher or lower level of one or more genes than the cells of the anterior, posterior or central regions. The cells of the central-posterior region may express a higher level of one or more genes than the cells of the anterior, posterior or central regions, and wherein the one or more genes are selected from NODAL, CER1, DAND5, BMP7. FOXA2, NOTO1, SHH and LEFTY1,2.

The central-posterior region may consist of at least 2%, at least 5%, at least 10%, at least 15%, at least 20%, at least 25%, at least 30%, at least 35%, at least 40%, at least 45% or 50% of the polarised three-dimensional cellular aggregate. Preferably, the central-posterior region consists of at least 5% of the polarised three-dimensional cellular aggregate.

The polarised three-dimensional cellular aggregate may exhibit spatial collinearity of HOX gene expression along the anterior-posterior axis. The polarised three-dimensional cellular aggregate may exhibit spatial and temporal collinearity of HOX gene expression along the anterior-posterior axis. The spatial collinearity of HOX gene expression along the anterior-posterior axis may comprise the sequential and ordered expression along this axis of HOX 1-13 from each of the A, B, C and D clusters. The spatial collinearity of Hox gene expression along the anterior-posterior axis may comprise the temporally sequential and ordered expression along this axis of HOX 1-13 from each of the A, B, C and D clusters.

The cells of the dorsal region may express a lower level of one or more genes than the cells of the ventral region, and wherein the one or more genes are selected from SHH, NODAL, LEFTY1, 2, TBX6 and KDR.

The cells of the dorsal region may express a higher level of one or more genes than the cells of the ventral region, and wherein the one or more genes are selected from SOX2, OTX2, IRX3, SOX1, POU3F1, POU3F2 AND PAX6.

The cells of the dorsal region may express a lower level of SHH, NODAL, LEFTY1, 2, TBX6 and/or KDR than the cells of the ventral region, and wherein the cells of the dorsal region express a higher level of SOX1 than the cells of the ventral region.

The cells of the dorsal region may express a lower level of SHH, NODAL, LEFTY1, 2, TBX6 and/or KDR than the cells of the ventral region, and wherein the cells of the dorsal region express a higher level of SOX2 than the cells of the ventral region.

The cells of the dorsal region may express a lower level of SHH, NODAL, LEFTY1, 2, TBX6 and/or KDR than the cells of the ventral region, and wherein the cells of the dorsal region express a higher level of SOX1 and SOX2 than the cells of the ventral region.

The dorsal region may consist of at least 2%, at least 5%, at least 10%, at least 15%, at least 20%, at least 25%, at least 30%, at least 35%, at least 40%, at least 45% or 50% of the polarised three-dimensional cellular aggregate. Preferably, the dorsal region consists of at least 5% of the polarised three-dimensional cellular aggregate The ventral region may consist of at least 2%, at least 5%, at least 10%, at least 15%, at least 20%, at least 25%, at least 30%, at least 35%, at least 40%, at least 45% or 50% of the polarised three-dimensional cellular aggregate. Preferably, the ventral region consists of at least 5% of the polarised three-dimensional cellular aggregate.

The cells of the medial region may express a lower level of one or more genes than the cells of the lateral regions, and wherein the one or more genes are selected from OSR1, PECAM, MEOX1, TBX6, PAX2, LEFTY1 and PITX2. The cells of the medial region may express a lower level of OSR1, MEOX1, and PAX2 than the cells of the lateral regions.

The cells of the medial region express a higher level of one or more genes than the cells of the lateral regions, and wherein the one or more genes are selected from SOX1, SOX2, DAND5, CER1, LFNG, FOXA2, and NOTO1.

The cells of the medial region may express a lower level of MEOX1 and/or TBX6 than the cells of the lateral regions, and wherein the cells of the medial region express a higher level of SOX2 than the cells of the lateral regions.

The cells of the medial region may express a lower level of MEOX1 and/or TBX6 than the cells of the lateral regions, and wherein the cells of the medial region express a higher level of SOX1 than the cells of the lateral regions.

The medial region may consist of at least 2%, at least 5%, at least 10%, at least 15%, at least 20%, at least 25%, at least 30%, at least 35%, at least 40%, at least 45% or 50% of the polarised three-dimensional cellular aggregate. Preferably, the medial region consists of at least 5% of the polarised three-dimensional cellular aggregate.

The lateral regions may consist of at least 2%, at least 5%, at least 10%, at least 15%, at least 20%, at least 25%, at least 30%, at least 35%, at least 40%, at least 45% or 50% of the polarised three-dimensional cellular aggregate. Preferably, the lateral regions consist of at least 5% of the polarised three-dimensional cellular aggregate.

The cells of the right region may express a lower or higher level of one or more genes than the cells of the left region and wherein the one or more genes are selected from NODAL, LEFTY1, LEFTY2 and PITX2.

The cells of the right region may express a lower or higher level of one or more genes than the cells of the left region or one or more genes than the cells in the right region, and wherein the one or more genes are selected from NODAL, LEFTY1, LEFTY2 and PITX2.

The polarised three-dimensional axial aggregate may have axial organisation. The axial organisation may be as described herein with reference to the anterior-posterior, dorso-ventral and medio-lateral axes.

The one or more markers characteristic of endodermal cells or derivatives thereof may be one or more genes the expression of which is characteristic of endodermal cells or derivatives thereof. The one or more genes the expression of which is characteristic of endodermal cells or derivatives thereof may be selected from GSC, CDX2, NEDD9, PYY, SHH, SORCS2, CER1, SOX17, FOXA2, TRH1 and FOXA1.

The one or more genes the expression of which is characteristic of endodermal cells or derivatives thereof may be one or more genes the expression of which is characteristic of mesendodermal cells or derivatives thereof. The one or more genes the expression of which is characteristic of mesendodermal cells or derivatives thereof may be selected from BRA, MIXL1, LEFTY1, LEFTY2, AXIN2, TRH1, NODAL, WNT3a, WMT5a, DII1, and CDX2.

The one or more markers characteristic of derivatives of endodermal cells may be one or more genes the expression of which is characteristic of gut cells, optionally wherein the gut cells are foregut cells, midgut and/or hindgut cells and/or derivatives thereof (e.g.oesophagus, lung, trachea, pancreas, liver, stomach, intestine and/or colon cells).

The three-dimensional cellular aggregate may comprise an endoderm-like field of cells. The cells of the endoderm-like field of cells may express one or more of GSC, CDX2, NEDD9, PYY, SHH, SORCS2, CER1, SOX17, FOXA2, TRH1 and FOXA1. The cells of the endoderm-like field of cells may express SOX17, further optionally wherein the cells of the endoderm-like field of cells express one or more of GSC, CDX2, NEDD9, PYY, SHH, SORCS2, CER1, SOX17, FOXA2, TRH1 and FOXA1. The endoderm-like field of cells may be arranged in one or more tube-like structures.

The one or more markers characteristic of mesodermal cells or derivatives thereof may be one or more genes the expression of which is characteristic of mesodermal cells or derivatives thereof. The one or more markers characteristic of mesodermal cells or derivatives thereof may be selected from, BRA, MEOX1, OSR1, PAX2, ALDH1A2, MESP1, MESP2, TBX6, TCF15, MEOX1, FLK1/KDR, FOXA2, PITX2 and TBX1.

The one or more genes the expression of which is characteristic of mesodermal cells or derivatives thereof may be one or more genes the expression of which is characteristic of axial mesoderm or derivatives thereof. The one or more genes the expression of which is characteristic of axial mesoderm or derivatives thereof may be selected from BRA, FOXA2, NOTO1, CER1, SHH and NOGGIN.

The polarised three-dimensional cellular aggregate may comprise an axial mesoderm-like field of cells, optionally wherein the cells of the axial mesoderm-like field of cells express one or more of BRA, FOXA2, NOTO1, CER1, SHH and NOGGIN.

The one or more genes the expression of which is characteristic of mesodermal cells or derivatives thereof may be one or more genes the expression of which is characteristic of paraxial mesoderm or derivatives thereof. The one or more genes the expression of which is characteristic of paraxial mesoderm or derivatives thereof may be selected from MEOX1, MSGN1, TBX6, TCF15, MESP1, MESP2, and ALDH1A2.

The polarised three-dimensional cellular aggregate may comprise a paraxial mesoderm-like field of cells, optionally wherein the cells of the paraxial mesoderm-like field of cells express one or more of MEOX1, MSGN1, TBX6, TCF15, MESP1, MESP2, and ALDH1A2.

The three-dimensional cellular aggregate may comprise neuromesodermal progenitor cells (NMPs), optionally wherein the neuromesodermal progenitor cells co-express SOX2, BRA and NKX1.2.

The one or more genes the expression of which is characteristic of mesodermal cells or derivatives thereof may be one or more genes the expression of which is characteristic of somitic mesoderm, optionally wherein the one or more genes are selected from TCF15, MESP1, MESP2, RIPPLY1, RIPPLY2, MEOX1 and UNCX4.1.

The polarised three-dimensional cellular aggregate may comprise a somitic mesoderm-like field of cells, optionally wherein the cells of the somitic mesoderm-like field of cells express one or more of TCF15, MESP1, MESP2, MEOX1, UNCX4.1.

The one or more genes the expression of which is characteristic of mesodermal cells or derivatives thereof may be one or more genes the expression of which is characteristic of intermediate mesoderm or derivatives thereof, optionally wherein the one or more genes are selected from OSR1 and PAX2.

The polarised three-dimensional cellular aggregate may comprise an intermediate mesoderm-like field of cells, optionally wherein the cells of the intermediate mesoderm-like field of cells express one or more of OSR1 and PAX2.

The one or more genes the expression of which is characteristic of mesodermal cells or derivatives thereof may be one or more genes the expression of which is characteristic of notochord, optionally wherein the one or more genes are selected from BRA, NOGGIN, NOTO1, and FOXA2.

The polarised three-dimensional cellular aggregate may comprise node-like cells, optionally wherein the node-like cells express one or more of CHORDIN, NODAL, NOGGIN, NOTO1, DAND5, BMP7 and FOXA2.

The polarised three-dimensional cellular aggregate may comprise a cluster of cells and wherein the cells of the cluster of cells express NODAL.

The one or more genes the expression of which is characteristic of mesodermal cells or derivatives thereof may be one or more genes the expression of which is characteristic of lateral plate mesoderm, optionally wherein the one or more genes are selected from FLK1/KDR, LEFTY 1, LEFTY2 and PITX2.

The polarised three-dimensional cellular aggregate may comprise a lateral plate mesoderm-like field of cells, optionally wherein the cells of the lateral plate mesoderm-like field of cells express one or more of FLK1/KDR, LEFTY 1, LEFTY2 and PITX2.

The one or more markers characteristic of ectodermal cells or derivatives thereof may be one or more genes the expression of which is characteristic of ectodermal cells of derivatives thereof. The one or more genes the expression of which is characteristic of ectodermal cells of derivatives thereof may be selected from OTX2, GBX2, SIX1, SIX3, SOX2, SOX3, DLX5, EYA2 and BARX1.

The one or more markers characteristic of ectodermal cells or derivatives thereof are one or more markers characteristic of neural cells. The one or more markers characteristic of neural cells may be one or more genes the expression of which is characteristic of neural cells, optionally wherein the one or more genes are selected from SOX1, SOX2, SOX3, POU3F1, POU3F2, PAX6, NKX1.2 and ZEB2.

The one or more markers characteristic of neural cells may be one or more markers characteristic of neural precursors. The one or more markers characteristic of neural cells may be one or more markers characteristic of differentiated neural precursor cells. The one or more markers characteristic of neural cells may be one or more markers characteristic of neural derivatives. The neural derivatives may be neurons and/or glial cells. The one or more markers characteristic of neural precursors may be one or more genes the expression of which is characteristic of neural precursors, optionally wherein the genes are selected from SOX2, POU3F1, POU3F2, OLIG2, PAX6, PAX7, NKX2.1, NKX2.5.

The polarised three-dimensional cellular aggregate may comprise neural crest-like cells, optionally wherein the neural crest-like cells express one or more of PAX3, SOX5, SOX9, and SOX10.

The polarised three-dimensional cellular aggregate may comprise neuroectoderm-like region of cells, optionally wherein the cells of the neuroectoderm-like region express one or more of SOX2, SOX3, OTX2, DLX5, EYA2, and BARX1.

The polarised three-dimensional cellular aggregate may comprise epithelial tracks, optionally wherein the cells of the epithelial tracks express PAX6, SOX1, SOX2, SOX3.

The polarised three-dimensional cellular aggregate may comprise epithelial tubes, optionally wherein the cells of the epithelial tubes express PAX6, SOX1, SOX2 and/or SOX3.

The neuroectoderm derivatives may comprise neural plate or neural tube cells.

The one or more markers characteristic of primordial germ cells may be one or more genes the expression of which is characteristic of primordial germ cells. The one or more markers characteristic of primordial germ cells may be one or more genes the expression of which is characteristic of primordial germ cells. The one or more genes the expression of which is characteristic of primordial germ cells may be selected from SOX17, PRDM1, PRDM14, DAZL, TFAP2C and NANOS3. The one or more markers characteristic of primordial germ cells may be one or more markers characteristic of primordial germ cell derivatives.

The polarised three-dimensional cellular aggregate may be elongate along the anterior-posterior axis. The anterior-posterior axis may be at least 5%, at least 10%, at least 15%, at least 20%, at least 25%, at least 30%, at least 35%, at least 40%, at least 45% or at least 50% longer than the dorso-ventral axis. Preferably, the anterior-posterior axis is at least at least 10% longer than the dorso-ventral axis.

The diameter of the polarised three-dimensional cellular aggregate at the anterior end may be greater than the diameter of the polarised three-dimensional cellular aggregate at the posterior end.

The polarised three-dimensional cellular aggregate may be elongated along the anterior-posterior axis, optionally wherein the cells of the anterior region express a lower level of BRA than the cells of the posterior region.

The polarised three-dimensional cellular aggregate may have undergone one or more morphological elongation, optionally wherein the morphological elongations are convergent-extension and proliferation.

The polarised three dimensional aggregate may comprise, within a BRA expressing region, an oval, polarized structure with differential adhesion between its cells that acts as a source of axial mesoderm.

The polarised three-dimensional cellular aggregate may comprise one or more of cavities, tubular structures, cysts pores, lumens, folds, plates, tracts, and segments.

The polarised three-dimensional cellular aggregate may have undergone one or more morphological shape changes, optionally wherein the morphological shape changes are one or more of elongation, cavitation, cyst formation and epithelialisation.

The polarised three-dimensional cellular aggregate may comprise a cavitated structure, optionally wherein the cells of the cavitated structure express GATA6.

The polarised three-dimensional cellular aggregate may have undergone bilaterally symmetrical budding at defined positions of the anteroposterior axis. The bilaterally symmetrical buds may be limb buds.

The polarised three-dimensional cellular aggregate may comprise an internal morphological structure at the posterior end. The morphological structure may be an epithelial rosette-like and/or lumen-like structure.

The polarised three-dimensional cellular aggregate may comprise one or more cells undergoing a Mesenchymal-to-epithelial transition.

The polarised three-dimensional cellular aggregate may comprise one or more cells undergoing an epithelial-to-mesenchymal transition The polarised three-dimensional cellular aggregate may release one or more cells from the posterior region.

The polarised three-dimensional cellular aggregate may comprise primordial germ cell-like cells (PGCs). The PGCs may express SOX17, PRDM1, PRDM14, DAZL, TFAP2C and/or NANOS3.

The polarised three-dimensional cellular aggregate may comprise clusters of cells expressing PRDM1 in the anterior region.

The polarised three-dimensional cellular aggregate may comprise one or more of axial mesodermal derivatives, paraxial mesodermal derivatives, intermediate mesodermal derivatives and the lateral plate mesodermal derivatives.

The paraxial mesodermal derivatives may comprise somite cells.

The intermediate mesodermal derivatives may comprise kidney cells and/or gonadal cells.

The lateral plate mesodermal derivatives may be selected from one or more of cardiac cells, haematopoietic cells and limb cells.

The polarised three-dimensional cellular aggregate may comprise at least 50 cells, at least 100 cells, at least 200 cells, at least 300 cells, at least 400 cells, at least 500 cells, at least 600 cells, at least 800 cells, at least 900 cells, at least 1000 cells, at least 1500 cells, at least 2000, at least 2500 cells, at least 5000 cells, at least 10,000 cells, at least 15,000 cells, at least 20,000 cells, at least 30,000 cells, at least 40,000 cells or at least 50,000 cells. Preferably, the polarised three-dimensional cellular aggregate comprises at least 20,000 cells. The polarised three-dimensional cellular aggregate may comprise 50-100,000 cells, 100-75,000 cells, 200-50,000 cells, 300-25,000 cells, 400-10,000 cells, 500-5,000 cells, 750-2,500 cells or 1000-2,000 cells. Preferably, the polarised three-dimensional cellular aggregate comprises 20,000-75,000 cells.

The polarised three-dimensional cellular aggregate may have a length of at least 0.05 mm, at least 0.1 mm, at least 0.2 mm, 0.3 mm, at least 0.4 mm, at least 0.5 mm, at least 0.6 mm, at least 0.7 mm, at least 0.8 mm, at least 0.9 mm, at least 1 mm or at least 1.5 mm. Preferably the polarised three-dimensional cellular aggregate has a length of at least 0.2 mm. The polarised three-dimensional cellular aggregate may have a length of 0.05-2 mm, 0.1-2 mm, 0.2-2 mm, 0.3-1.9 mm, 0.5-1.8 mm, 0.6-1.7 mm, 0.7-1.6 mm, 0.8-1.5 mm, 0.9-1.4 mm, 1.0-1.3 mm or 1.1-1.2 mm. Preferably, the polarised three-dimensional cellular aggregate has a length of 0.2-2 mm.

The polarised three-dimensional cellular aggregate may comprise one or more progenitor cells or derivatives thereof. As used herein the term “progenitors” or “progenitor cells” refer to both stem cells and progenitor cells.

The one or more progenitor cells or derivatives thereof may be:

a. haematopoietic progenitor cells and/or derivatives thereof;
b. cardiac progenitor cells and/or derivatives thereof;
c. paraxial mesoderm and/or derivatives thereof;
d. somites and/or derivatives thereof (e.g. dermatome, myotome and/or sclerotome cells);
e. neural crest and/or derivatives thereof;
f. neural ectoderm and/or derivatives thereof (e.g. neural plate/tube cells and/or neurons);
g. placodal ectoderm and/or derivatives thereof (e.g. otic and/or nasal primordia);
h. intermediate mesoderm progenitor cells and/or derivatives thereof (e.g. renal and/or gonadal primordia);
i. axial mesoderm progenitor cells;
j. neuromesodermal progenitor cells and/or derivatives thereof (e.g. spinal cord neural progenitors and/or derivatives thereof, and/or paraxial mesoderm and/or derivatives thereof);
k. lateral plate mesoderm and/or derivatives thereof;
l. primordial germ cells and/or derivatives thereof;
m. node cells and/or derivatives thereof; and/or
n. endoderm and/or derivatives thereof (e.g. primordia for the oesophagus, stomach, intestine, lungs, pancreas, liver, trachea, thymus and/or thyroid).

The polarised three-dimensional cellular aggregate may comprise haematopoietic progenitors and/or progenitors of the vascular system.

The haematopoietic progenitors may express one or more of FLK1, GATA2, and SCL1.

The progenitors of the vascular system may express one or more of FLK1, SCL, RUNX1, GATA2, CXCR4, CKIT, CD41, CD35 and VE-CDH.

The polarised three-dimensional cellular aggregate may comprise a vascularised system of cells.

The polarised three-dimensional cellular aggregate may comprise endothelial cells, optionally wherein the endothelial cells express one or more of VE-CDH, FLK1 and SCL.

The polarised three-dimensional aggregate may comprise cysts comprising clusters of endothelial cells expressing one or more of VE-CDH, CD41, CD43 and CD45.

The haematopoietic progenitors may express HB, optionally wherein the HB gene is fetal HB or adult HB. The haematopoietic progenitors may express genes characteristic of haemogloblin, optionally wherein the haemoglobin is fetal haemoglobin (HBf) or adult haemoglobin (HBa). The haematopoietic progenitors derived from the polarised three-dimensional cellular aggregate may be capable of generating differentiated blood cells in vitro (e.g. as measured by a Colony Forming Cell (CFC) assay), optionally wherein the differentiated blood cells are myeloid cells and/or lymphoid cells. The myeloid cells may be selected from one or more of monocytes, macrophages, neutrophils, basophils, eosinophils, erythrocytes, megakaryocytes and platelets. The lymphoid cells may be selected from one or more of T cells, B cells, and natural killer cells.

The three-dimensional cellular aggregate may comprise a cardiac structure. The cardiac structure may be located in the anterior region of the three-dimensional cellular aggregate, optionally wherein the cardiac structure is asymmetrically located in the anterior region of the three-dimensional cellular aggregate. The cardiac structure may comprise components of a vascular system, optionally wherein the cardiac structure comprises one or more blood vessels. The cardiac structure may comprise one or more cavities. The cardiac structure may comprise one or more tubular structures. The cardiac structure may beat or contract spontaneously. The cardiac structure may beat or contract at 10-250 beats per minute, 20-200 beats per minute, 30-175 beats per minute, 40-150 beats per minute, 50-125 beats per minute, or 60-100 beats per minute. The cells of the cardiac structure may express at any point in their development one or more cardiac specific genes. The cells of the cardiac structure may express one or more cardiac specific genes. The one or more cardiac specific genes may be selected from GATA4, GATA6, HAND1, CTNT, NKX2.5 and TBX1. The cardiac structure may be located in the anterior region of the polarised three dimensional cellular aggregate. The cardiac-like region of cells may be located asymmetrically in the anterior region of the polarised three dimensional cellular aggregate.

The polarised three-dimensional cellular aggregate may be generated in vitro from one or more human embryonic stem cells (ESCs). The human ESCs may be naïve human ESCs.

The polarised three-dimensional cellular aggregate may be generated in vitro from one or more human induced pluripotent stem cells (iPSCs).

The polarised three-dimensional cellular aggregate may be generated in vitro from a single pluripotent stem cell. The polarised three-dimensional cellular aggregate may be generated in vitro from a single colony derived from a single pluripotent stem cell.

The polarised three-dimensional cellular aggregate may be generated in vitro from one or more blastomeres derived from a pre-implantation epiblast.

The invention provides a method for obtaining a polarised three-dimensional cellular aggregate, the method comprising:

(a) generating a cell suspension from one or more human pluripotent stem cells, wherein the cell suspension comprises one or more disassociated human pluripotent stem cells;

(b) culturing the cell suspension under conditions that promote the transformation of at least one of the disassociated human pluripotent stem cells into a three-dimensional cellular aggregate; and (c) culturing the three-dimensional cellular aggregate under conditions that promote the transformation of the three-dimensional cellular aggregate into a polarised three-dimensional cellular aggregate;

wherein the polarised three-dimensional cellular aggregate is a polarised three-dimensional cellular aggregate as defined herein.

The invention provides a method for obtaining a polarised three-dimensional cellular aggregate, the method comprising:

(a) pre-treating one or more human pluripotent stem cells, wherein the step of pre-treating comprises culturing the human pluripotent stem cells in a medium comprising an activator of Wnt signalling;

(b) generating a cell suspension from the pre-treated human pluripotent stem cells, wherein the cell suspension comprises one or more disassociated human pluripotent stem cells;

(c) culturing the cell suspension under conditions that promote the transformation of at least one of the disassociated human pluripotent stem cells into a three-dimensional cellular aggregate; and (d) culturing the three-dimensional cellular aggregate under conditions that promote the transformation of the three-dimensional cellular aggregate into a polarised three-dimensional cellular aggregate.

Step (c) may comprise sorting the cell suspension (e.g. by flow cytometry) until the three-dimensional cellular aggregate is formed.

The method may further comprise culturing the polarised three-dimensional cellular aggregate under conditions that promote the differentiation of one or more cells of the polarised-three dimensional cellular aggregate into progenitor cells or derivatives thereof. The progenitor cells or derivatives thereof may be progenitor cells or derivatives of any of the tissues or organs described herein.

In the methods, the polarised three-dimensional cellular aggregate may be cultured in the absence of extra-embryonic cells or tissue including primitive endoderm, amnion and/or trophoblast.

In the methods, the polarised three-dimensional cellular aggregate may be cultured in the presence of extra-embryonic cells or tissue including primitive endoderm, amnion and/or trophoblast.

A "cell suspension" as used herein refers to a suspension comprising single disassociated pluripotent stem cells i.e. a single cell suspension, and/or to a suspension comprising disassociated colonies comprising pluripotent stem cells i.e. a colony suspension, and/or to a suspension comprising a disassociated colony comprising pluripotent stem cells wherein the colony is derived from a single pluripotent stem cell i.e. a clonal suspension.

The invention provides a method for obtaining one or more progenitor cells or derivatives thereof, the method comprising:

(a) generating a cell suspension from one or more human pluripotent stem cells, wherein the cell suspension comprises one or more disassociated human pluripotent stem cells;

(b) culturing the cell suspension under conditions that promote the transformation of at least one of the disassociated pluripotent stem cells into a three-dimensional cellular aggregate;

(c) culturing the three-dimensional cellular aggregate under conditions that promote the transformation of the three-dimensional cellular aggregate into a polarised three-dimensional cellular aggregate, wherein the polarised three-dimensional cellular aggregate is as defined herein; and (d) culturing the polarised three-dimensional cellular aggregate under conditions that promote the differentiation of one or more cells of the polarised-three dimensional cellular aggregate into progenitor cells or derivatives thereof.

The invention provides a method for obtaining one or more progenitor cells or derivatives thereof, the method comprising:

(a) pre-treating one or more human pluripotent stem cells, wherein the step of pre-treating comprises culturing the human pluripotent stem cells in a medium comprising an activator of Wnt signalling (b) generating a cell suspension from the pre-treated human pluripotent stem cells, wherein the cell suspension comprises one or more disassociated human pluripotent stem cells;

(c) culturing the cell suspension under conditions that promote the transformation of at least one of the disassociated pluripotent stem cells into a three-dimensional cellular aggregate;

(d) culturing the three-dimensional cellular aggregate under conditions that promote the transformation of the three-dimensional cellular aggregate into a polarised three-dimensional cellular aggregate; and (e) culturing the polarised three-dimensional cellular aggregate under conditions that promote the differentiation of one or more cells of the polarised-three dimensional cellular aggregate into progenitor cells or derivatives thereof.

The one or more progenitor cells or derivatives thereof may be:

a. haematopoietic progenitor cells and/or derivatives thereof;
b. cardiac progenitor cells and/or derivatives thereof;
c. paraxial mesoderm and/or derivatives thereof;
d. somites and/or derivatives thereof (e.g. dermatome, myotome and/or sclerotome cells);
e. neural crest and/or derivatives thereof;
f. neural ectoderm and/or derivatives thereof (e.g. neural plate/tube cells and/or neurons);
g. placodal ectoderm and/or derivatives thereof (e.g. otic and/or nasal primordia);
h. intermediate mesoderm progenitor cells and/or derivatives thereof (e.g. renal and/or gonadal primordia);
i. axial mesoderm progenitor cells;
j. neuromesodermal progenitor cells and/or derivatives thereof (e.g. spinal cord neural progenitors and/or derivatives thereof, and/or paraxial mesoderm and/or derivatives thereof);
k. lateral plate mesoderm and/or derivatives thereof;
l. primordial germ cells and/or derivatives thereof;
m. node cells and/or derivatives thereof; and/or
n. endoderm and/or derivatives thereof (e.g. primordia for the oesophagus, stomach, intestine, lungs, pancreas, liver, trachea, thymus and/or thyroid).

The polarised three-dimensional cellular aggregate may be a polarised three-dimensional cellular aggregate as defined herein.

The polarised three dimensional cellular aggregate may have an axial organisation.

The step of pre-treating may comprise culturing the human pluripotent stem cells in a pluripotency-promoting medium.

The step of pre-treating may comprise culturing the human pluripotent stem cells in a pluripotency-promoting medium, optionally comprising an activator of Wnt signalling The step of pre-treating may comprise culturing the human pluripotent stem cells on a solid substrate. The solid substrate may be a coated solid substrate. The solid substrate may be coated with vitronectin. The solid substrate may be coated with a basement membrane matrix (e.g. Geltrex™). The basement membrane matrix may comprise one or more of laminin, collagen (e.g. collagen IV), heparan sulphate proteoglycan and entactin. The gel may be formed from basement membrane extract, which may be isolated from a suitable basement membrane-secreting cell type, such as Engelbreth-Holm-Swarm (EHS) mouse sarcoma cells. Basement membrane extracts produced from EHS cells are commercially available under the trade names Matrigel (BD Biosciences, Franklin Lakes, N.J., USA), Cultrex (Trevigen Inc., Gaithersburg, Md., USA) and Geltrex (Invitrogen). Their major component is laminin, followed by collagen IV, heparan sulphate proteoglycan and entactin.

The solid substrate may be a coated with a gel and/or matrix. The gel or matrix may comprise at least one extracellular matrix protein or analogue thereof. The extracellular matrix protein may be one or more of collagen (e.g. collagen IV), laminin, fibronectin, vitronectin and/or gelatin. Preferably, the extracellular matrix protein is collagen (e.g. collagen IV) and/or laminin. The matrix may activate signalling through β-integrin receptors. The gel may be a hydrogel. The gel may comprise or consist substantially of basement membrane matrix. The basement membrane matrix may be as described herein. Alternatively, the gel may be a polyacrylamide gel, e.g. a gel comprising across-linked polymer matrix formed by polymerisation of acrylamide and bisacrylamide (e.g. N,N'-methylenebisacrylamide). Other suitable gel types may include alginate gels, polyethylene glycol (PEG) based gels and agarose gels.

The step of culturing the human pluripotent stem cells may comprise feeder-dependent culture e.g. feeder-dependent culture on mouse embryonic fibroblasts.

The step of pre-treating may comprise growing the human pluripotent stem cells to 60-85% confluency.

The step of pre-treating may comprise culturing the human pluripotent stem cells in a medium comprising an activator of Wnt signalling and an inhibitor of TGFβ, Nodal and/or Activin signalling.

The step of pre-treating may comprises culturing the human pluripotent stem cells in a medium comprising an activator of Wnt signalling and an activator of TGFβ, Nodal, Activin and/or signalling.

The step of pre-treating may comprise culturing the human pluripotent stem cells in a medium comprising an activator of Wnt signalling and an inhibitor of BMP signalling, The step of pre-treating may comprise culturing the human pluripotent stem cells in a medium comprising an activator of Wnt signalling and an activator of BMP signalling.

The step of pre-treating may comprise culturing the human pluripotent stem cells in a medium comprising an activator of Wnt signalling and an inhibitor of TGFβ, Nodal and/or Activin signalling. The inhibitor of TGFβ, Nodal and/or Activin signalling may be an ALK4, 5, 7 inhibitor. The ALK4, 5, 7 inhibitor may be SB-431542 or SB-5051214.

The step of pre-treating may comprise culturing the human pluripotent stem cells with one or more organogenesis promoting factors. The organogenesis promoting factors may be selected from:

a. One or more activators of Wnt signalling e.g. to promote the generation of derivatives of the three germ layers and PGCs;
b. One or more activators of Wnt signalling and an inhibitor of TGFβ, Nodal and/or Activin signalling e.g. to promote the generation of proneural ectoderm and neuromesodermal progenitors;
c. One or more activators of Wnt signalling and one of more activators of TGFβ, Nodal and/or Activin e.g. to promote the generation of endoderm and derivatives thereof and mesodermal derivatives (e.g. paraxial and/or axial mesoderm); and d. One or more activators of Wnt signalling and one or more activators of BMP signalling e.g. to promote the generation of lateral and intermediate mesoderm and/or derivatives thereof.

The step of culturing the cell suspension comprises centrifugation of the one or more disassociated human pluripotent stem cells, optionally wherein centrifugation of the one or more disassociated pluripotent stem cells initiates the formation of the three-dimensional cellular aggregate.

The step of culturing the cell suspension may comprise culturing the cell suspension in a basal differentiation medium. The step of culturing the cell suspension may comprise culturing the cell suspension in a medium comprising an activator of Wnt signalling. The step of culturing the cell suspension may comprise culturing the cell suspension in a medium comprising an activator of Wnt signalling and a Rock inhibitor. The step of culturing the cell suspension may comprise culturing on a low adherence plate.

The step of culturing the three-dimensional cellular aggregate may comprise culturing the three-dimensional cellular aggregate in a basal differentiation medium. The step of culturing the three-dimensional cellular aggregate may comprise culturing the three-dimensional cellular aggregate in a medium comprising an activator of Wnt signalling. The step of culturing the three-dimensional cellular aggregate may comprise culturing the three-dimensional cellular aggregate in a medium comprising an activator of Wnt signalling and a Rock inhibitor.

The step of culturing the three-dimensional cellular aggregate may comprise culturing the three-dimensional cellular aggregate in a medium comprising an inhibitor of TGFβ, Nodal and/or Activin signalling. The step of culturing the three-dimensional cellular aggregate may comprise culturing the three-dimensional cellular aggregate in a medium comprising an inhibitor of TGFβ, Nodal and/or Activin signalling and a Rock inhibitor.

The step of culturing the three-dimensional cellular aggregate may comprise culturing the three-dimensional cellular aggregate in a medium comprising an activator of TGFβ, Nodal and/or Activin signalling. The step of culturing the three-dimensional cellular aggregate may comprise culturing the three-dimensional cellular aggregate in a medium comprising an inhibitor of TGFβ, Nodal and/or Activin signalling, an activator of Wnt signalling and a Rock inhibitor.

The activator of Wnt signalling may be any agent or molecule that activates the Wnt signalling pathway including the downstream signalling network. The activator of Wnt signalling may be an activator of Wnt/β-catenin signalling. The activator of Wnt signalling may be a soluble protein. The activator of Wnt signalling may be a GSK inhibitor, optionally wherein the GSK3 inhibitor is CHI99021 (Chi or Chiron). The activator of Wnt signalling may be selected from one or more of WNT3, WNT3a, WNT5, WNT8 and WNT11.

The activator of Nodal signalling may be soluble Nodal. The activator of Activin signalling may be soluble Activin.

The inhibitor of TGFβ, Nodal and/or Activin signalling may be an ALK4, 5, 7 inhibitor. The ALK4, 5, 7 inhibitor may be SB-431542 or SB-5051214.

The step of culturing the three-dimensional cellular aggregate may comprise culturing on a low adherence plate.

The one or more human pluripotent stem cells are one or more human embryonic stem cells (ESCs).

The one or more human pluripotent stem cells may be one or more human induced pluripotent stem cells (iPSCs).

The one or more disassociated human pluripotent stem cells may be a single pluripotent stem cell.

The one or more disassociated human pluripotent stem cells may be a colony from a single human pluripotent stem cell.

The one or more disassociated human pluripotent stem cells may be one or more blastomeres from a pre-implantation epiblast.

The one or more of steps of the method may be performed with the human pluripotent stem cells in suspension, three-dimensional cellular aggregates in suspension and/or polarised three-dimensional cellular aggregates in suspension. One or more of steps of the method may be performed with the three-dimensional cellular aggregates and/or polarised three-dimensional cellular aggregates not embedded in a gel (e.g. a hydrogel). Preferably, none of steps (b)-(e) are performed with the three-dimensional cellular aggregates and/or polarised three-dimensional cellular aggregates embedded in a gel (e.g. a hydrogel).

The cell suspension may comprise $1\times10^3$-$1\times10^5$ cells/ml, $5\times10^3$-$5\times10^4$ cells/ml or $7.5\times10^3$-$2.5\times10^4$ cells/ml.

The step of pre-treating may comprise culturing the human pluripotent stem cells in a medium comprising an activator of Wnt signalling is performed for 1-48 hours, 6-42 hours, 12-36 hours, 18-30 hours or 24 hours.

The step of culturing the cell suspension may be performed for at least 10 minutes, at least 15 minutes, at least 30 minutes, at least 1 hour, at least 6 hours, at least 12 hours, or at least 24 hours.

The step of culturing the cell suspension may be performed for 10 minutes-48 hours, 15 minutes-42 hours, 20 minutes-36 hours, 25 minutes-30 hours, 30 minutes-24 hours, 35 minutes-18 hours, 40 minutes-12 hours, 45 minutes-12 hours, 50 minutes-6 hours, 55 minutes-1 hour.

The steps of culturing the three-dimensional cellular aggregate and culturing the polarised three-dimensional cellular aggregated may be performed for a total of at least 72 hours, at least 96 hours, at least 120 hours, at least 130 hours, at least 140 hours, at least 150 hours, at least 160 hours, at least 170 hours, at least 180 hours, at least 190 hours, at least 200 hours, at least 210 hours, at least 220 hours, at least 230 hours, at least 240 hours or at least 250 hours.

The step of culturing the three-dimensional cellular aggregate may comprise shaking the three-dimensional cellular aggregate.

The step of culturing the polarised three-dimensional cellular aggregate may comprise shaking the polarised three-dimensional cellular aggregate.

The step of culturing the cell suspension may comprise transferring one or more of the disassociated human pluripotent stem cells into a well of a plate. The well may be a round-bottomed well. The number of disassociated human pluripotent stem cells transferred into a well of the plate may be 50-1000 disassociated human pluripotent stem cells, 200-800 disassociated human pluripotent stem cells, 300-800 disassociated human pluripotent stem cells, or 400-600 disassociated human pluripotent stem cells.

The invention provides a polarised three-dimensional cellular aggregate (i.e. a polarised human three-dimensional cellular aggregate) obtainable by any one of the methods defined herein.

The invention provides a progenitor cell or derivative thereof (i.e. a human progenitor cell or derivative thereof) obtainable by any one of the methods defined herein. The invention further provides an organ and/or tissue comprising one or more progenitor cell or derivative thereof. The progenitor cell or derivative thereof may be any one of more of the progenitor cells or derivatives thereof described herein. The organ or tissue may be blood, vascular tissue, kidney, heart, lungs, somites, dermatome, myotome, sclerotome, neural crest, neural tube, neurons, sensory placode, gonad, notochord, neural-mesodermal progenitors, primordial germ cells, node, oesophagus, stomach, intestine, pancreas, liver, trachea, thymus and/or thyroid.

The polarised three-dimensional cellular aggregate may not comprise extra-embryonic cells or tissue including primitive endoderm, amnion and/or trophoblast. The polarised three-dimensional cellular aggregate may not be associated with extra-embryonic cells or tissue including primitive endoderm, amnion and/or trophoblast. The polarised three-dimensional cellular aggregate may not be associated with extra-embryonic cells or tissue including primitive endoderm, amnion and/or trophoblast. The polarised three-dimensional cellular aggregate may be unable to form yolk sac or placenta. The polarised three-dimensional cellular aggregate may not comprise yolk sac or placenta. The polarised three-dimensional cellular aggregate may lack any anterior neural derivatives. The polarised three-dimensional cellular aggregate may be unable to form brain tissue. The polarised three-dimensional cellular aggregate may not comprise brain tissue. The polarised three-dimensional cellular aggregate does not have the inherent capacity of developing into a human being.

BRIEF DESCRIPTION OF THE DRAWINGS

The present disclosure will now be described, by way of example only, with reference to the accompanying drawings in which:

FIG. 16: Spatial transcriptomics by tomo-seq identifies clusters of gene expression. a, Quantification of number of genes (left) and number of unique transcripts (right) detectable in each section along the anterior-posterior (AP) axis of Chiron pre-treated human gastruloids made from 72 h RUES2-GLR gastruloids. Sections above the threshold and used for downstream gastruloid tomo-seq analysis are marked in blue, while sections below the threshold are coloured dark grey. Two replicates are shown. b, Hierarchical clustering of reproducible tomo-seq gene expression patterns along the length of the AP axis (which has been normalised between 0 at the most anterior and 1 at the most posterior). Ribbon indicates standard deviation for the set of genes within each cluster. c, Selection of gene traces along the AP axis for both gastruloids, indicating the degree of reproducibility for individual genes.

EXAMPLES

The inventors have shown that human pluripotent stem cells (hPSCs) can be used to generate polarised three-dimensional cellular aggregates (or human gastruloids). These 3-dimensional aggregates undergo morphological rearrangements, differentiate into all three germ layers and display organised gene expression patterns that are similar to those observed in the developing mammalian embryo. Using this system, the inventors have shown that aggregates of hPSCs are able to spontaneously break symmetry without additional extra-embryonic tissues. They also polarise expression of genes including GATA6, BRA and SOX2 and undergo dynamic morphological changes including elongation. Using TOMO-sequencing to spatially map transcriptional profiles along an anterior-posterior axis, the inventors have shown that the human gastruloids recapitulate many of the transcriptional features observed in early mammalian embryos, including elements of the tailbud, mesodermal derivatives, somitogenesis network, cardiovascular system, placodal ectoderm, cardiopharyngeal mesoderm, spinal cord. As an experimentally tractable system, the human gastruloids could prove to be invaluable in revealing human-specific regulatory processes that occur during early development and in enhancing our understanding of human embryonic development and disease.

Example 1—Culture of Human Embryonic Stem Cells Using Conditions Previously Used to Generate Mouse Gastruloids Using two human embryonic stem cell (hESC) lines, H9 (T/Bra:GFP) and MasterShef 7, and subjecting them to equivalent conditions that generate mouse gastruloids (Baillie-Johnson, P., et al., 2015) revealed that, while in some instances cell aggregation was achieved, we never observed signs of growth, polarization of BRA expression or tissue elongation.

Figure 5:
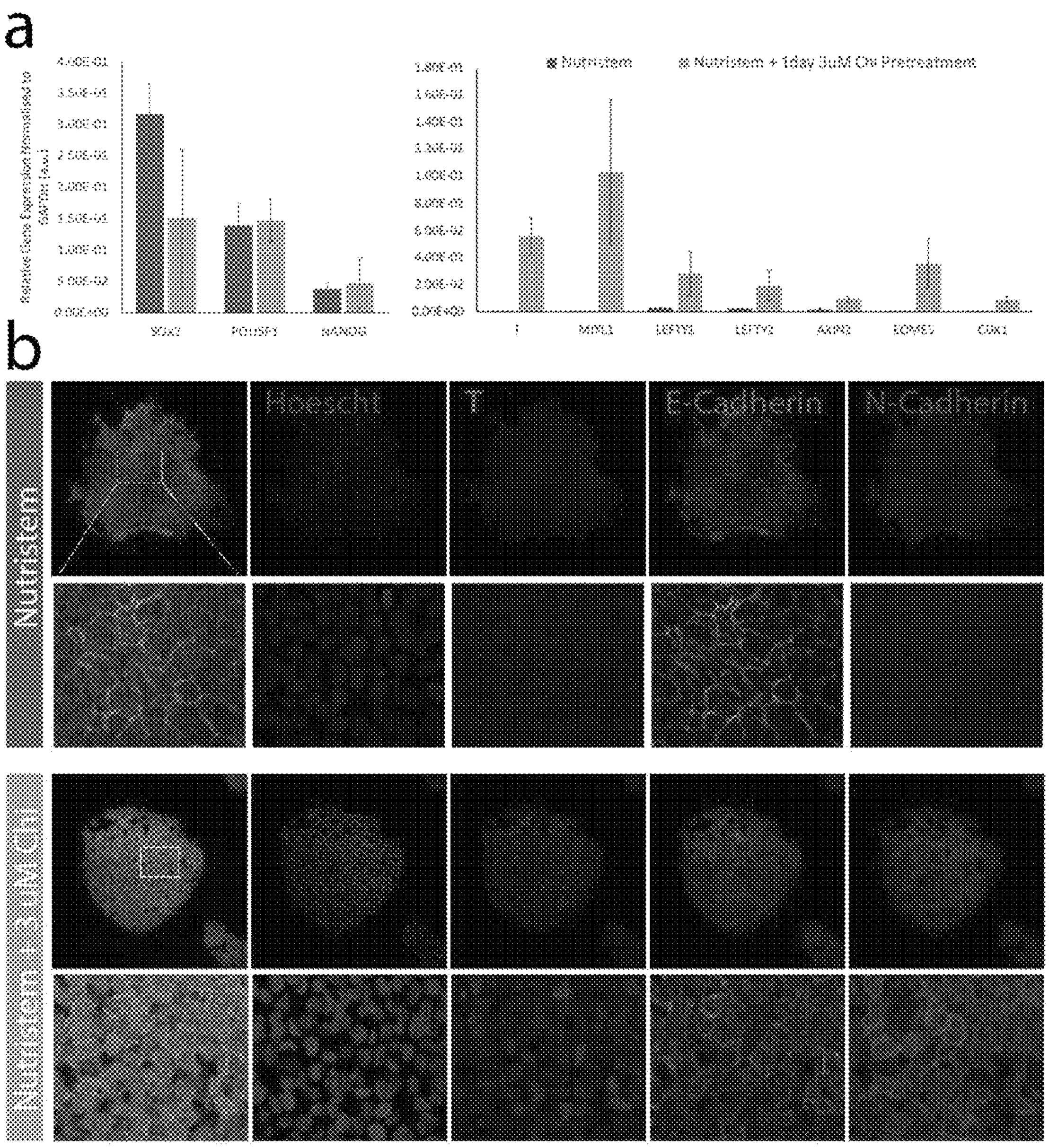
FIG. 5: Pretreatment with Chiron promotes human gastruloid formation. (a) RT-qPCR analysis revealed that, compared to hESCs maintained in pluripotency medium (Nutristem) those pre-treated with Chiron show similar expression of pluripotency factors, but significantly increased expression of mesendodermal markers. Average of two independent experiments with two cell lines (RUES2-GLR and MasterShef7) done in technical triplicate. Error bars reveal standard deviation between the two cell line averages. (b) Immunofluorescence of two-dimensional adherent cells maintained in Nutristem (top) or pretreated with Chiron (bottom), which show increased levels of BRA and the localization of N-cadherin (CDH2) at the membrane.

Example 2—Culture of Human Embryonic Stem Cells and Human Induced Pluripotent Stem Cells Using Methods of the Invention We pre-treated hESCs for 1 day in pluripotency medium supplemented with 3-3.5 μM of the Wnt signalling agonist, CHIR99021 (hereafter referred to as Chiron) before aggregation; effectively shifting the Chiron pulse to before the aggregation rather than 48 h after aggregation as is the case in mouse gastruloids (Baillie-Johnson, P., et al., 2015). These Chiron pre-treated hESCs were found to still express pluripotency markers at levels equivalent to cells maintained in pluripotency medium alone (FIG. 5*a*). However, the pre-treated cells displayed slightly reduced levels of SOX2 and increased expression of mesendodermal marker genes including Bra (denoted “T”), MIXL1, LEFTY1, LEFTY2, AXIN2, EOMES, CDX1 suggesting that they had been primed towards primitive streak-like fates. This was accompanied by a switch in the expression and membrane localisation of CDH1 (E-cadherin) towards CDH2 (N-cadherin; FIG. 5*b*).

Figure 1:
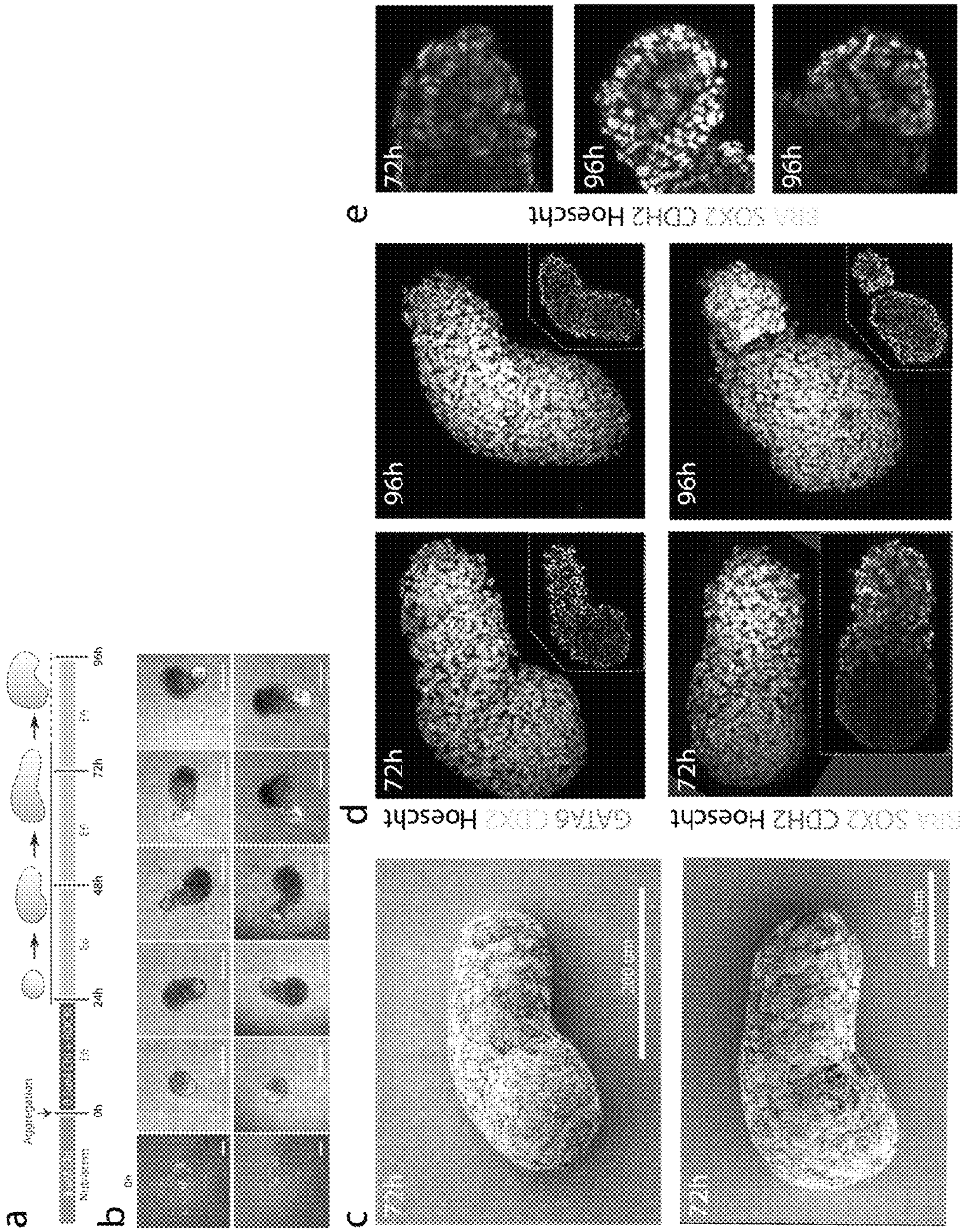
FIG. 1 illustrates the structure and morphology of human gastruloids. (a) Schematic diagram of the protocol used to generate human gastruloids. (b) The temporal dynamics of human gastruloid formation and development, from individual cells (0 h) to a spherical aggregate (<24 h) and finally an elongated gastruloid (72-96 h) before the elongation retracts (96 h). Shown are two representative examples from the RUES2-GLR cell line. (c) Scanning Electron Micrograph (SEM) of human gastruloids at 72 h. Shown are two representative examples. (d) 3D projections of immunofluorescently labelled gastruloids at 72 h (left) and 96 h (right), showing anterior-posterior localization of GATA6 and CDX2 respectively (top) and the co-localised domains of SOX2 and BRA with CDH2 (N-cadherin) at 72 h which resolves to spatially distinct domains of SOX2 and BRA at 96 h (bottom). Insets show individual planes of the respective gastruloid (bounded by dashed lines). (e) Lumenised, rosette-like structures at the posterior-most end of gastruloids, which show CDH2 localisation at the membranes, with domains of SOX2 and BRA expression.

Following Chiron pre-treatment, the human ESCs were dissociated and 300-500 cells were placed into individual wells of round-bottomed 96 well plates, in basal differentiation medium supplemented with 0.5 μM Chiron and ROCKi to aid aggregation. Following a 24 hour period in this condition, the medium was supplemented with fresh E6 and the medium was replaced daily (FIG. 1*a*). Within 24 hours of plating, the individual cells form compact, spherical aggregates, which then progressively polarise morphologically and form long elongated structures within 48 hours (FIG. 1*b*). This elongation phase is maximal at around 72 hours after aggregation, after which the elongated structures tend to retract or curl round on themselves (FIG. 1*c*).

Figure 6:
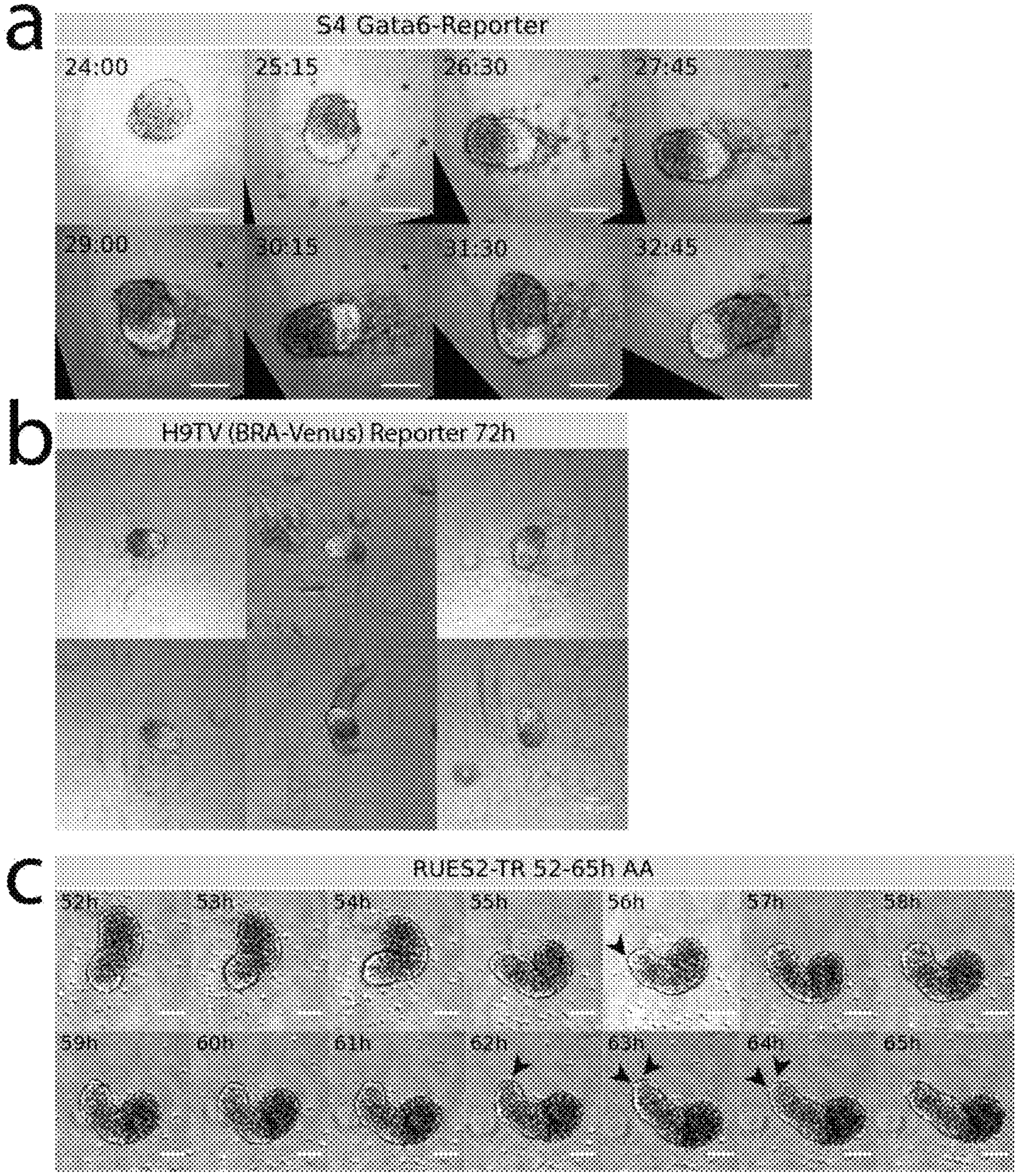
FIG. 6: Reporter-lines and Live imaging of human gastruloids. (a) Live imaging analysis of the GATA6-GFP line from 24-35 hours after aggregation, following Chiron pretreatment, showing anterior localisation of GATA6-GFP. (b) Six representative examples of human gastruloids at 72 hours made with the H9TV which expreses BRA-Venus reporter. (c) Live imaging of the RUES2-GLR line showing cells extruding from the elongating tip of the gastruloid (black arrowheads) between 55 and 62 hours after aggregation (AA).

These elongated structures bear a remarkable resemblance to mouse embryonic stem cell-derived gastruloids which, as well as displaying an elongated morphological structure, exhibit expression of differentiation genes patterned along defined axes. In order to test whether these elongated structures are similar in this respect to mouse gastruloids, we stained 72 h elongated aggregates for differentiation markers, and noticed a clear anterior-posterior distinction between the two ends: at the BRA expressing end, we observe an overlap of expression with CDX2 and, at the other end, there is a domain expressing GATA6 (FIG. 1*f*); the polarisation of GATA6 to the anterior end was also confirmed using a reporter system (FIG. 6*a*). The BRA/CDX2 expressing cells are located at the tip of the elongating structure and, as in the embryo this combination identifies the caudal-most region of the embryo, which we believe that it is the same in the gastruloid and was also observed using a fluorescent reporter line (Allison et al., 2018) (FIG. 6*b*). This polarised region of BRA was also positive for CDH2 (N-cadherin) and overlapped with a SOX2 positive region at 72 hours, but gradually resolved to distinct BRA and SOX2 expression domains (FIG. 1*f*). These frequently appeared to be arranged such that the BRA and SOX2 domains were separated along an axis that was roughly orthogonal to the AP axis, suggesting the presence of at least 2 axes. In a proportion of aggregates, we also observed internal morphological structures that appeared to show epithelial rosette-like or lumen-like structures at the most posterior end (FIG. 1*g*), and the extrusion of single cells from the posterior-most tip of the gastruloid (FIG. 6*c*). Because of the elongated morphology, polarised BRA expression and similarity to mouse gastruloids that is initiated from a human ESC population, we have termed these structures human gastruloids.

Figure 2:
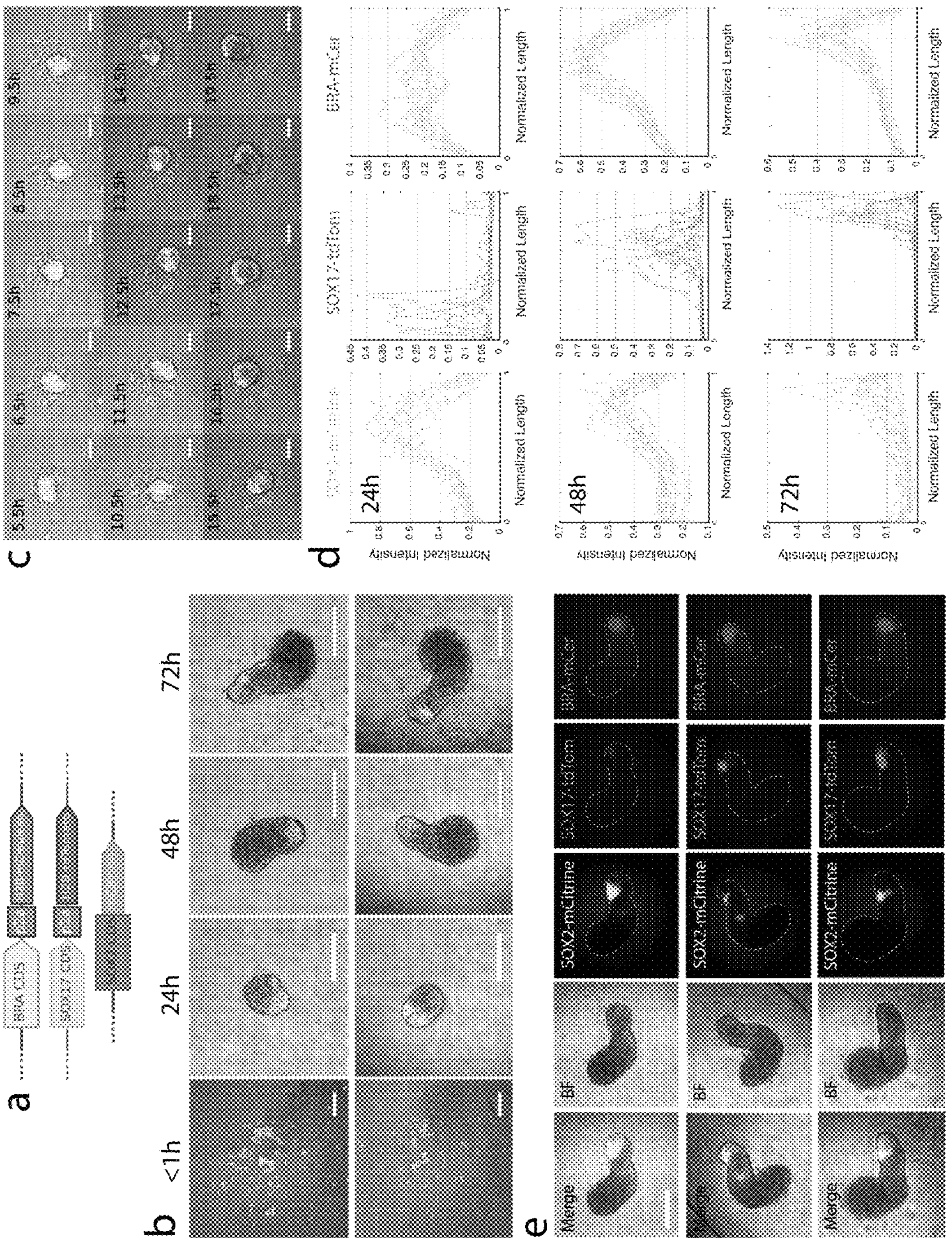
FIG. 2: Dynamic polarization of three germ layers in human gastruloids. (a) Schematic diagram of the RUES2-GLR cell line used to generate human gastruloids as a germ layer reporter. (b) The temporal dynamics of human gastruloid formation and development, from individual cells (Oh) to a spherical aggregate (<24 h) and finally an elongated gastruloid (72 h). Shown are two representative examples. (c) Live imaging of the dynamics of symmetry breaking between 5.5 h and 19.5 h after aggregation, showing the initial polarization of SOX2-mCitrine, and the appearance of SOX17-tdTomato positive cells at the alternative end. (d) Quantification of the dynamics of SOX2-mCitrine, SOX17-tdTomato and BRA-mCerulean along the anterior-posterior axis of the elongating gastruloid. Thin lines represent individual gastruloids. (e) Final localization of the three germ layer markers at 72 h after aggregation, with BRA at the most posterior of the human gastruloid, and with SOX2 and SOX17 domains located more anteriorly. Shown are 3 representative examples. CDS, Coding Sequence; tdTom, tdTomato; mCer, mCerulean.

However, in order to ascertain whether these human gastruloids are indeed capable of generating organised derivatives of the three germ layers, as occurs during gastrulation, we made use of a germ layer reporter line (RUES2-GLR; Martyn et al., 2018). This hESC line utilises fluorescent reporters of the BRA (mesoderm), SOX17 (endoderm and primordial germ cells) and SOX2 (neuroectoderm) marker genes, which allows dynamic assessment of germ layer generation and organisation (FIG. 2*a*). Human gastruloids made with this cell line initially express SOX2 due to their pluripotent status before aggregation (FIG. 2*b*).

They then rapidly polarise the expression of SOX2 to one coherent domain at the end of the aggregate, with individual SOX17 expressing cells appearing throughout the remaining portion of the aggregate (FIG. 2*c*). Between 24 and 48 hours after aggregation, the aggregate undergoes an elongation, as BRA becomes localised to the SOX2 positive region of the gastruloid (FIG. 2*d*). By 72 hours after aggregation, the elongated gastruloid expresses BRA at the posterior-most portion of the elongation, with neighbouring SOX17 and SOX2 expressing domains adjacently (FIG. 2*e*).

Altogether these observations suggest that the hESC derived gastruloids develop a structure similar to that of mouse gastruloids and exhibit an outline of axial organization. To explore further the complexity and organization of these gastruloids, we decided to analyse the transcriptional profile of human gastruloids using TOMO-sequencing (TOMO-seq), a technique that allows to sample the spatial organization of transcription at the whole genome level (Junker et al., 2014 and Kruse et al., 2016). Gastruloids at 72 hours after aggregation were fixed, embedded for sectioning along their AP axis and subjected to RNAseq analysis (FIG. 3*a*).

Figure 3:
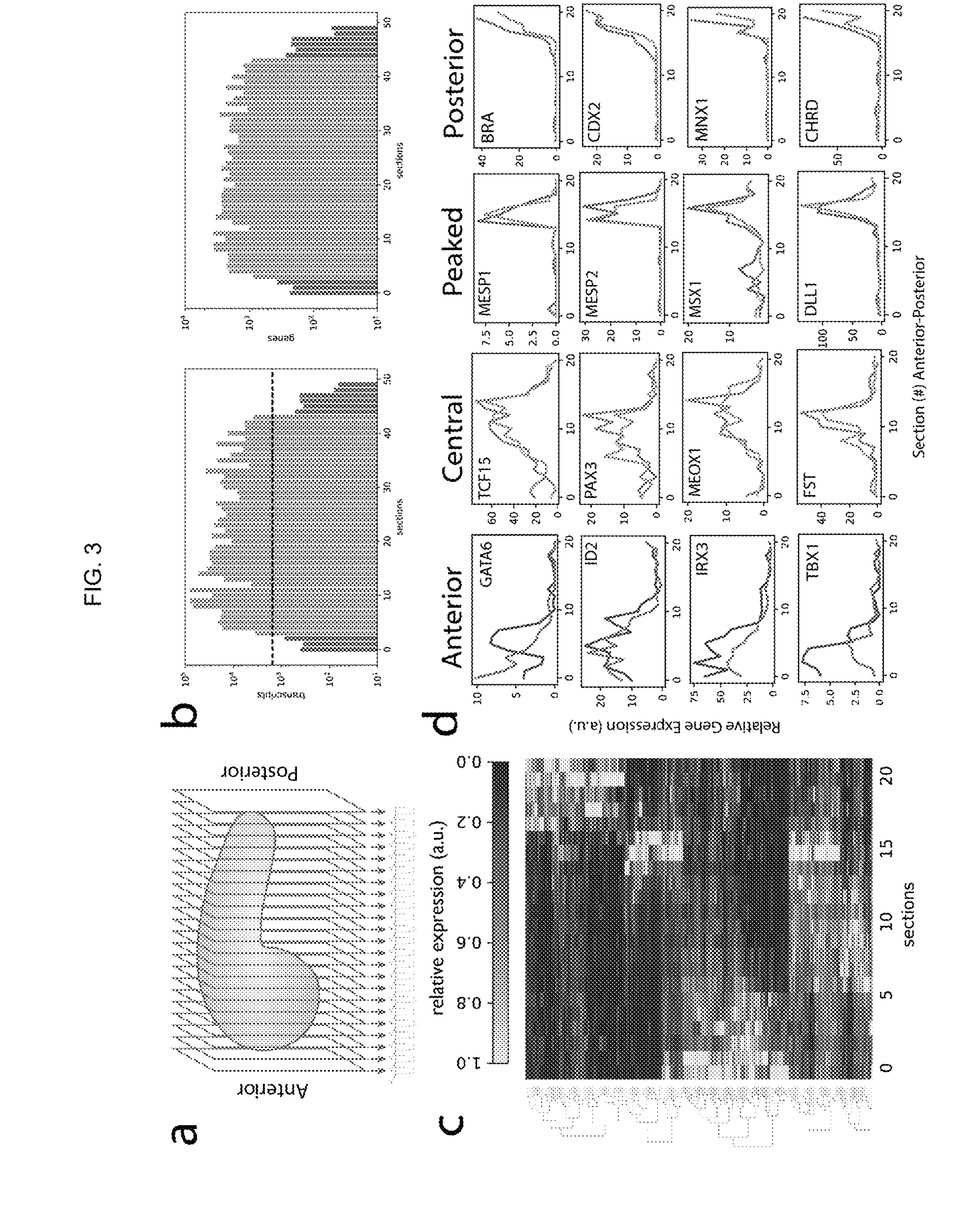
FIG. 3: Presence of anterior-posterior axis in human gastruloids. (a) Schematic representation of gastruloid analysis by TOMO-sequencing, involving sectioning of embedded gastruloid in anterior-to-posterior direction and RNA-sequencing of each section. (b) Number of transcripts (left) and genes (right) mapped to during TOMO-sequencing of each section. Blue bar represent background, while orange bars represent gastruloid sequencing. (c) Heatmap of selected variably-expressed genes, showing hierarchical clustering of genes found to be particularly localised to the anterior (red dendrogram), central region (orange dendrogram), central-posterior peaked (blue dendrogram) or posterior (green dendrogram). (d) Selected examples of genes showing anterior localisation (pink lines), central localisation (orange lines), peaked central-posterior localisation (blue lines) and posterior localisation (green).
Figure 4:
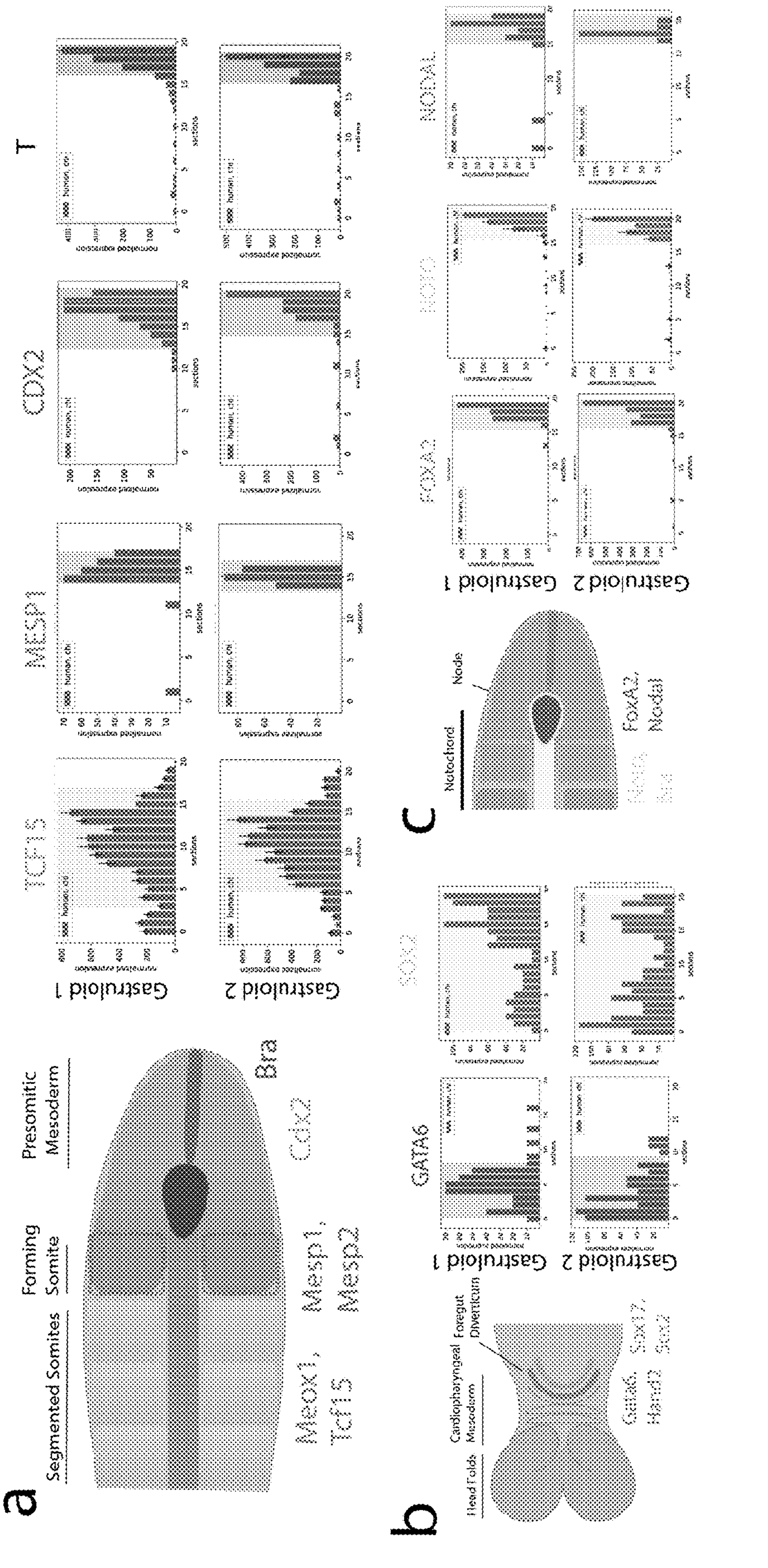
FIG. 4: Similarity of human gastruloids to elements of the mouse embryo. (a) Comparison between schematic of somitogenesis in the mouse embryo (left) with gene expression patterns in the human gastruloid (right). Similar comparisons can be drawn for elements including the cardiopharyngeal mesoderm and foregut anteriorly (b) and for the node (c).

When all genes were assessed for spatial localisation along the AP axis, we found 4 main classes of gene expression (FIG. 3*c*). These corresponded to (1) anterior-most expressed genes, including GATA6, HAND2, PRDM1, TBX1 and BMP2, (2) posterior-most expressed genes, including BRA (T), WNT3A, CDX2, BMP7, CHRDN, CYP26A1, MIXL1, DAND5, NOTO and FOXA2 (3) mid-gastruloid expressed genes, including MEOX1, TCF15, PAX3, SIX1, HOXA2 and HOXB1, and (4) genes which peak just anteriorly to the most posterior ones, representing either a node-like or somite-like structures, including DLL1, MESP1, MESP2 and NODAL.

Figure 7:
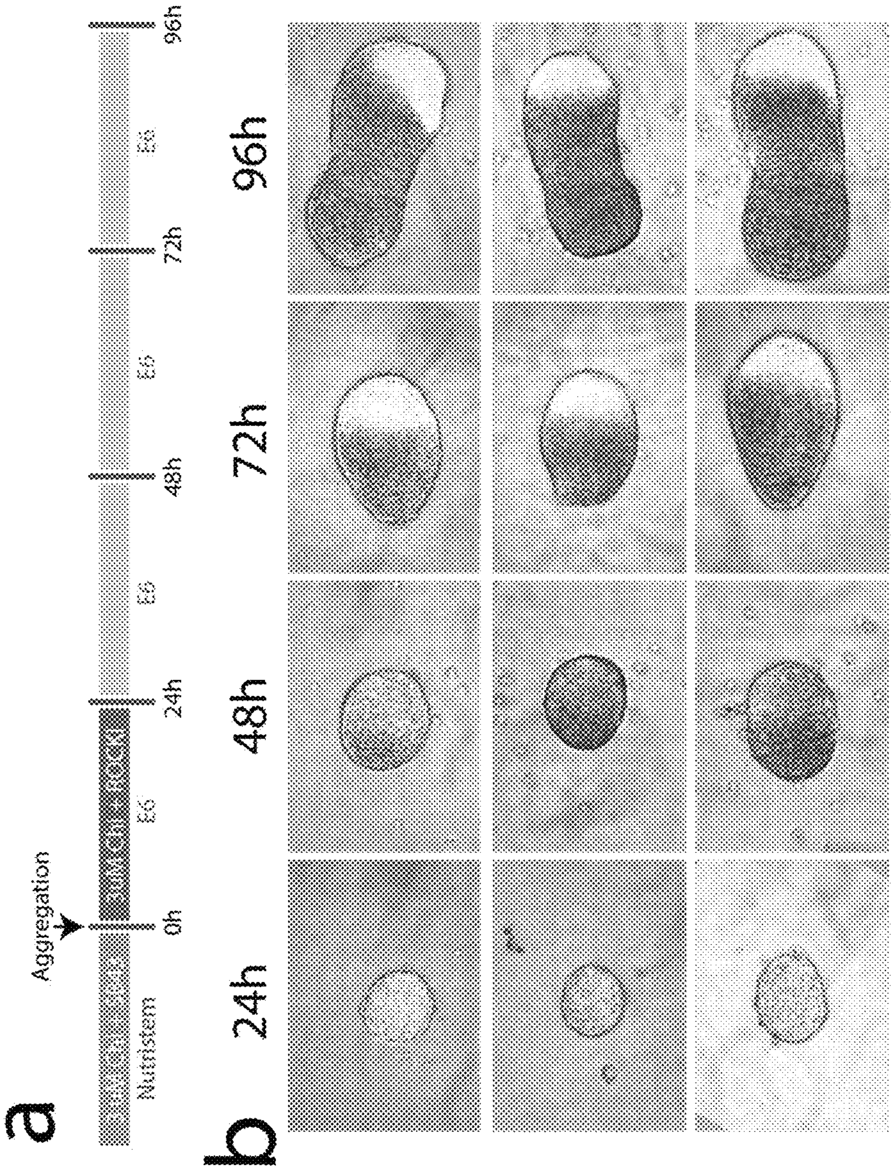
FIG. 7: Effect of SB431542 on 'dorsalisation' of human gastruloids. (a) Schematic of human gastruloid protocol with SB431542 pre-treatment. (b) Temporal progression of SB431542-pretreated human gastruloids made from the RUES2-GLR line, showing altered dynamics and expression patterns compared to the Chiron-only pretreated human gastruloids (see FIG. 2*b* for comparison). Panel shows 3 representative examples (c) TOMO-sequencing analysis reveals that expression of posterior markers including BRA and CYP26A1 are comparable between the Chiron-only pre-treatment and the Chiron+SB431542 pre-treated human gastruloids. (d) However, some of the genes expressed in the central region of the Chiron-only pre-treated human gastruloids, are shifted more to the anterior with additional SB431542 pre-treatment. (e) Increased expression of neuroectodermal genes including SOX2 and SOX3 suggest that the SB431542 pre-treated human gastruloids might be more 'dorsalised'.
Figure 7:
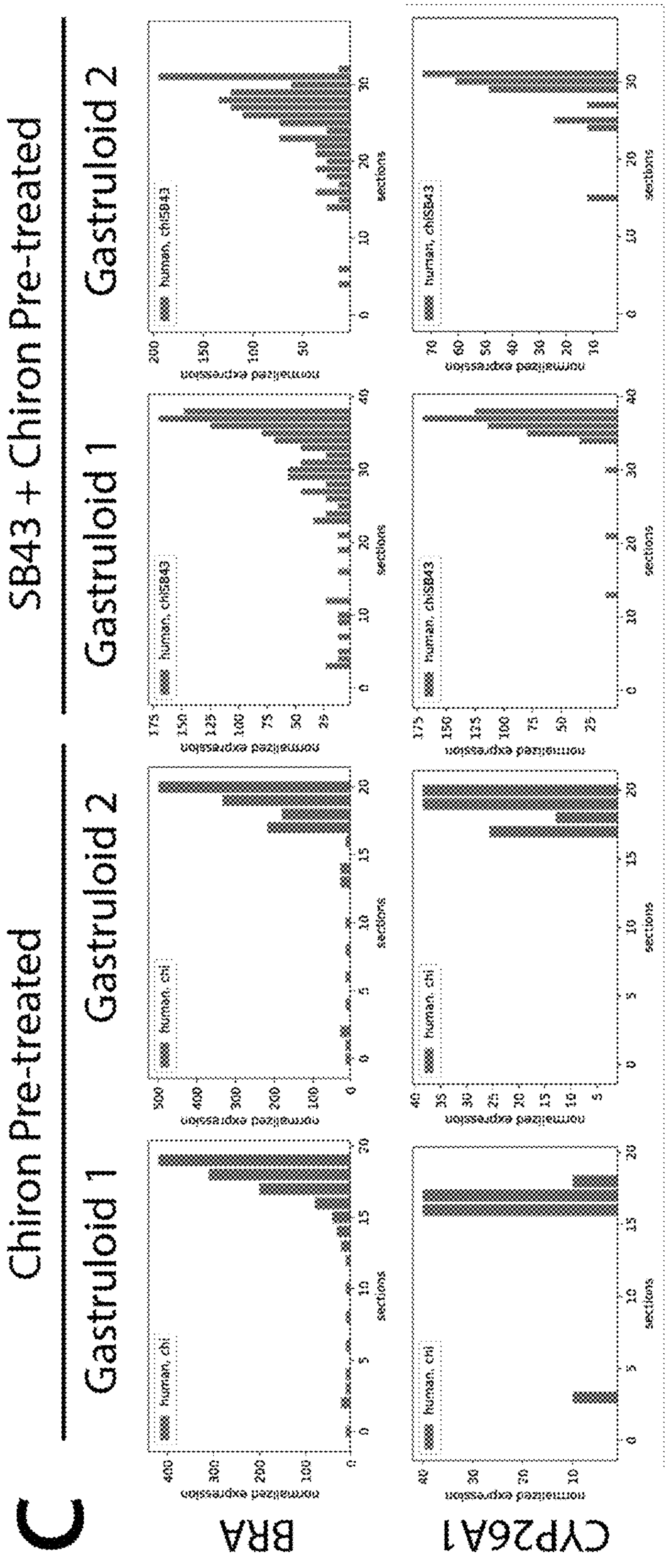
Figure 7:
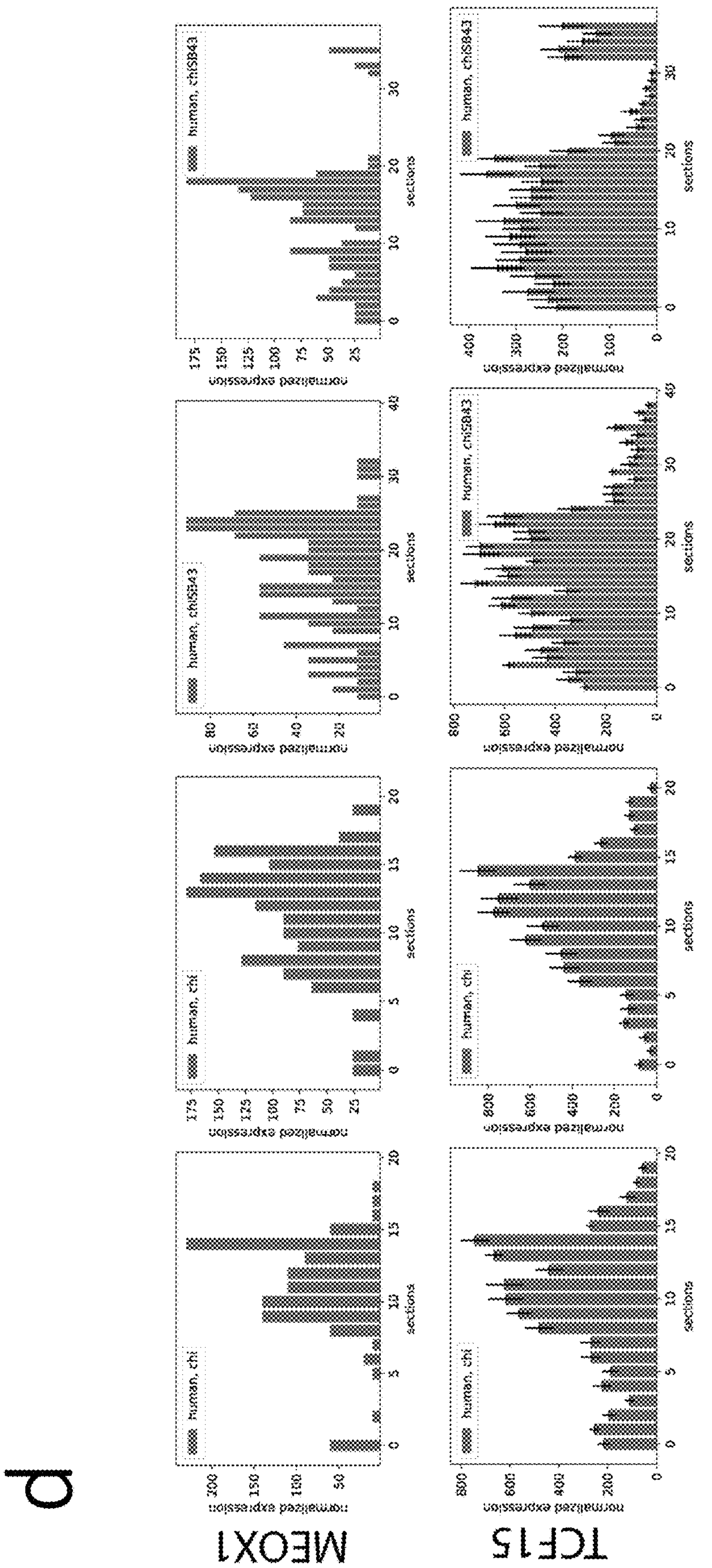
Figure 7:
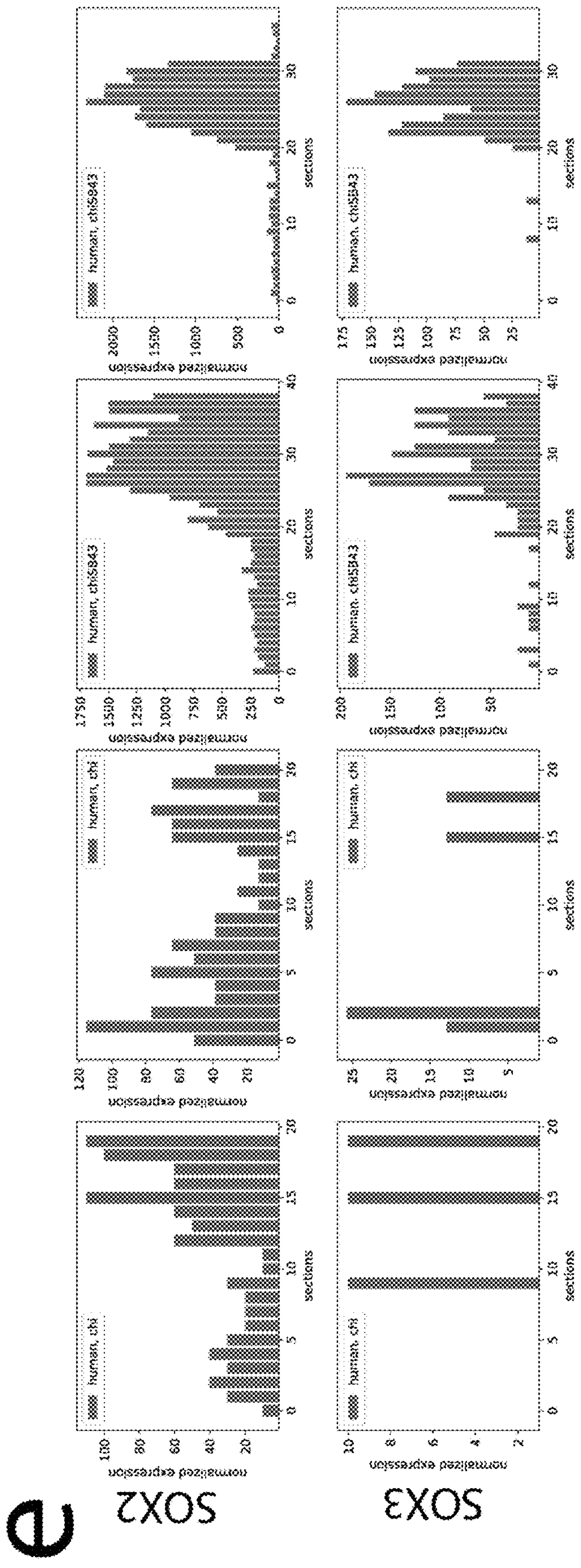

Interestingly, we saw little evidence of anterior neural tissues such as forebrain, midbrain or hindbrain in a manner that is similar to our results with mouse gastruloids (Turner et al., 2017[1]; Turner et al., 2017[2]; and van den Brink et al., 2014). In order to attempt to reveal these alternative elements of the structure, we sought to 'dorsalize' the starting population of cells using the Nodal inhibitor SB431542 (herein known as SB431542; FIG. 7*a*). Together with Chiron, SB431542 has been shown to promote the expression of multipotent caudal neural progenitor markers in hESCs and nodal inhibition is utilised in mouse and human PSCs to reduce mesoderm specification and promote neural development. Indeed, our gastruloids from this condition show distinctly larger domains of SOX2 expression which overlap with Bra expression, and exhibit fewer, if any, SOX17 expressing cells (FIG. 7*b*). They do however, continue to express BRA, CYP26A1, and WNT3A in the posterior domain, in a manner than is comparable to the Chiron pre-treated human gastruloids (FIG. 7*c*). However, in contrast to the Chiron-pre-treated gastruloids, the SB431542 pre-treated gastruloids show no markers of a Node-like population of cells with no detectable expression of NODAL, NOTO, PITX2 or DAND5 and very little expression of FOXA2, as expected following Nodal signalling inhibition. We also see little or no expression of the asymmetry markers LEFTY1 and LEFTY2, or the more anterior cardiac mesoderm markers GATA4, GATA6 or HAND2. We also observe a shift of somitogenesis-like genes, typically expressed in a central region in Chrion pre-treated gastruloids, which become anteriorly localised in SB431542 pre-treated gastruloids, including MEOX and TCF15 (FIG. 7*d*). Additionally, we observe an increase in the domain-size and level of expression of SOX2 and SOX3 (FIG. 7*e*) suggesting an increase in neuroectodermal-like tissue. These observations lead us to believe that the SB431542 pre-treated human gastruloids might be biased towards a more 'dorsalised' fate, with more neuroectodermal and fewer endodermal markers expressed.

The Chiron pre-treated gastruloid structures therefore show a particularly high degree of organisation along the AP axis, ranging from a posterior-most expression of BRA, which in the mouse embryo is located in the primitive streak and tailbud region, through to an anterior GATA6 positive domain, which in the mouse is found in the cardiac crescent. This suggested to us that the human gastruloids might follow the spatial transcriptional regulatory principles of the developing embryo, and we sought to examine whether the spatial localisation of transcriptional markers of particular cell types are equivalently located in the gastruloids as in the mammalian embryo. Indeed, we observed that certain elements of the developing embryo are mirrored in the gastruloid system, including a tail bud-like posterior domain (expressing BRA, CDX2, WNT3A, FGF8 and CYP26A1), and anterior-localised elements of the cardiac primordia and cranial mesoderm (GATA4, GATA6, HAND1 and TBX1). Within the elongating region we observe expression of neural progenitor genes (SOX2) and low but detectable expression of neural differentiating cells (PAX6, SOX1, ZEB2) and, importantly, signs of organized somitogenesis arranged along the AP axis in a sequence (from posterior to anterior: BRA, TBX6, MEOX1, MESP2, TCF15,). Importantly, between the tail bud and the start of TBX6 expression we observe localized expression of CHRD, NOTO1, NODAL and LEFTY1,2 which suggests the existence of a node-like structure in the gastruloids. In addition, at the anterior end we also observe expression of FLK1/KDR and GATA2 which presages the appearance of endothelium and components of the hematopoietic system. An axial organization is supported by the spatially organized expression of members of the 4 HOX clusters along the AP axis. Altogether these results show that human gastruloids develop a body plan with all the hallmarks of the mammalian embryo.

Figure 8:
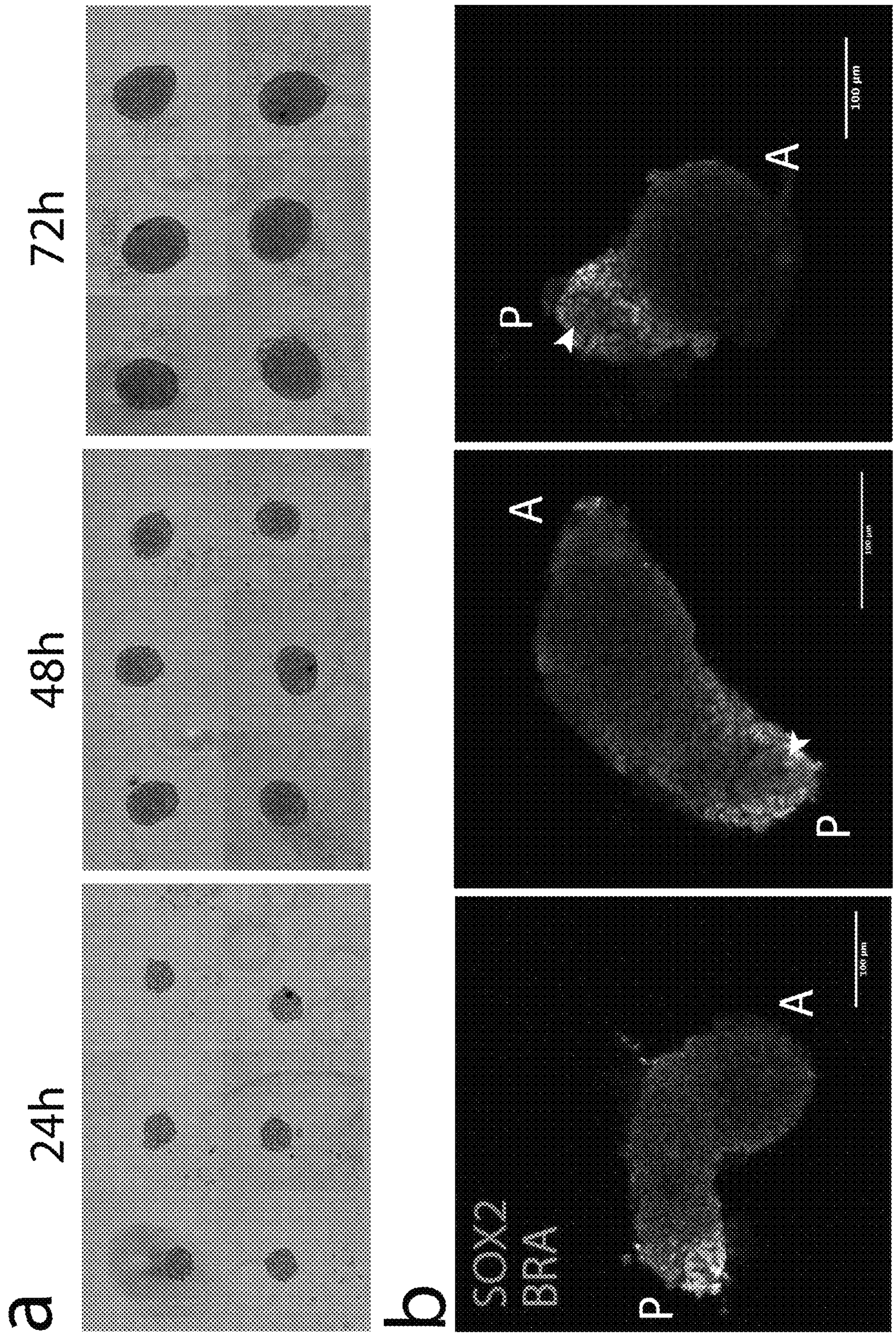
FIG. 8: Human gastruloids made from induced pluripotent stem cells. (a) Using the HYS01030 human induced pluripotent stem cell (iPSC) line pretreated with 3.5 uM Chiron 1 day before aggregation, and aggregating in Chiron and ROCK inhibitor led to the formation of spherical aggregates at 24 hours, which gradually became ovoid at 48 hours and polarised in their morphology at 72 hours after aggregation (a). 6 representative examples are show. (b) At 96 hours after aggregation, the human iPSC-derived gastruloids showed BRA and SOX2 clearly located at the posterior tip of the elongating gastruloid (marked 'P'; the anterior region is marked 'A'), in a manner that shows an anterior-posterior gradient. There is also some sign of a rosette-like or lumenised structure that expresses SOX2 in the posterior tip (arrowhead). 3 representative examples are shown.

Interestingly, we also found that similarly polarised and partially elongated structures could be derived from induced pluripotent stem cells (iPSCs) treated in the same manner as hESCs, suggesting that the human gastruloid system can be used with both pluripotent cell types (FIG. 8*a-b*).

Our results suggest that at 72 hrs after aggregation, human gastruloids are at a stage concordant with that of embryos undergoing gastrulation. The observation that 72 hrs AA human gastruloids appear to be undergoing somitogenesis does provide an anchor for the staging with reference to embryos in the Carnegie and Kyoto collections. In human embryos gastrulation begins at day 13 (Carnegie Stage 6, CS6) and continues for about five days. By day 17 (CS9) embryos show signs of somitogenesis, which are not present at CS8 as well as a node like structure. We have used the ratio of presomitic and somatic mesoderm in gastruloids (expression of, for example, Tbx6 and Uncx4.1) and in embryos (somites and distance from node to first somite) as an approximation to match both. Comparison suggests that human gastruloids 72 hrs AA are in a state approximately equivalent to CS9.

Our results show that hPSCs can organize into gastruloids that exhibit an axial organization reminiscent of the mammalian body plan at mid gastrulation and that they provide a useful experimental system to explore the early stages of human development in vitro from hESCs.

Figure 9:
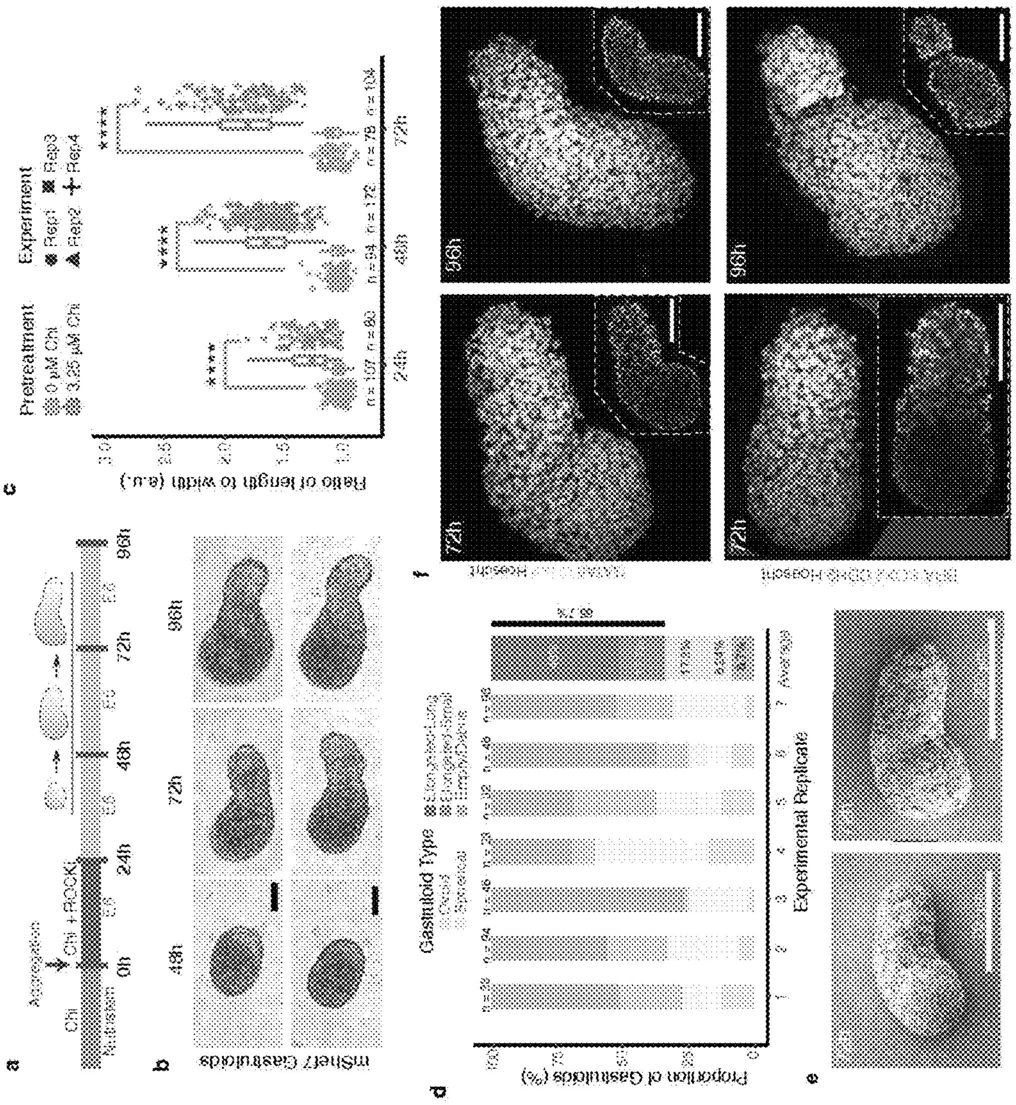
FIG. 9: Illustrates the structure and morphology of human gastruloids. a, Schematic diagram of the protocol used to generate human gastruloids. Chi, CHIR99021 or 'Chiron'; ROCKi, ROCK inhibitor; E6, Essential 6 medium. b, Temporal dynamics of human gastruloid development, from 48 hours after aggregation (h), to 96 h. Shown are two representative examples from the MasterShef7 (mShef7) cell line. Scalebar, 200 μm. c, Elongation of RUES2-GLR gastruloid elongation from 24-72 h, with and without Chiron (Chi) pre-treatment, plotted as jitter and boxplots (center line, median; box limits, upper and lower quartiles; whiskers, interquartile range). Shown are data from 2-4 independent biological replicates (Rep). Significance assessed by Welch two-sample t-test, $p<2.2e-16$ for all comparisons (****; two-sided testing; 24 h, $t=-12.673$, degrees of freedom (d.f.)=95.579; 48 h, $t=-32.156$, d.f.=226.52; 72 h, $t=-23.797$, d.f.=121.45). Text below each plot represents the number of gastruloids assayed per condition. d, Proportion of elongated gastruloids at 72 h, made from the RUES2-GLR line. Shown are 7 independent biological replicates (left), and the average proportions of gastruloid shapes observed at 72 hours (right). Text above each stacked bar indicates the number of gastruloids in each experimental replicate. e, Scanning Electron Micrograph (SEM) of human gastruloids made from the RUES2-GLR line at 72 h. Shown are two representative examples. Scale bars; 200 μm. f, Projections of 3D immunofluorescence-labelled RUES2-GLR human gastruloids at 72 h (left) and 96 h (right). Insets show individual section planes of the respective gastruloid (bounded by dashed lines). Scale bars; 100 μm.
Figure 13:
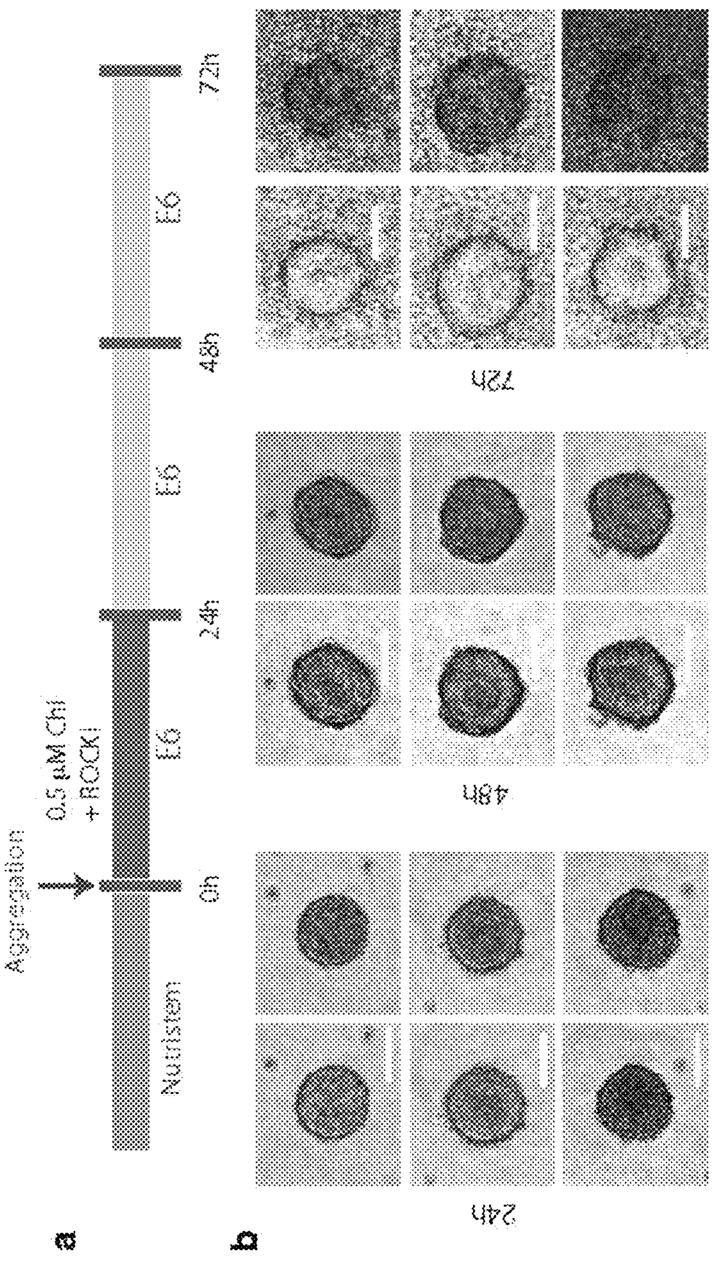
FIG. 13: Chiron pre-treatment optimisation and Morphological variability. a, Schematic of protocol without Chiron pre-treatment, but with aggregation in Chiron (Chi) and ROCK inhibitor (ROCKi) medium. b, Gastruloids made from the RUES2-GLR line without Chiron pre-treatment at 24, 48 and 72 h after aggregation. Shown are 3 representative examples for each timepoint, with all three fluorescent reporters (SOX2-mCitrine, SOX17-tdTomato and BRA-mCerulean; left) and without SOX2-mCitrine (right). Scalebar; 100 μm. c, Examples of reporter patterning in differential morphology classes, as assessed by automated segmentation providing gastruloid outline boundaries (yellow line indicates boundary used for quantifications). Three representative gastruloids per category are shown. Scale bar, 100 μm. d, Cell line-dependent optimisation of Chiron conditions. Shown are MasterShef7 cell-derived human gastruloids (left), with various Chiron pre-treatment (PT) and aggregation concentrations, showing variability of morphology. For each condition, two representative examples are shown. Scalebar; 100 μm. By comparison, RUES2-GLR derived human gastruloids (right) are shown following various Chiron pre-treatment (PT) and aggregation concentrations, showing variability of morphology. For each condition, three representative examples are shown. Scalebar; 100 μm. Red bounding boxes indicate concentrations at which gastruloids were deemed to be optimally elongated, and resultant conditions for subsequent gastruloid derivation.
Figure 13:
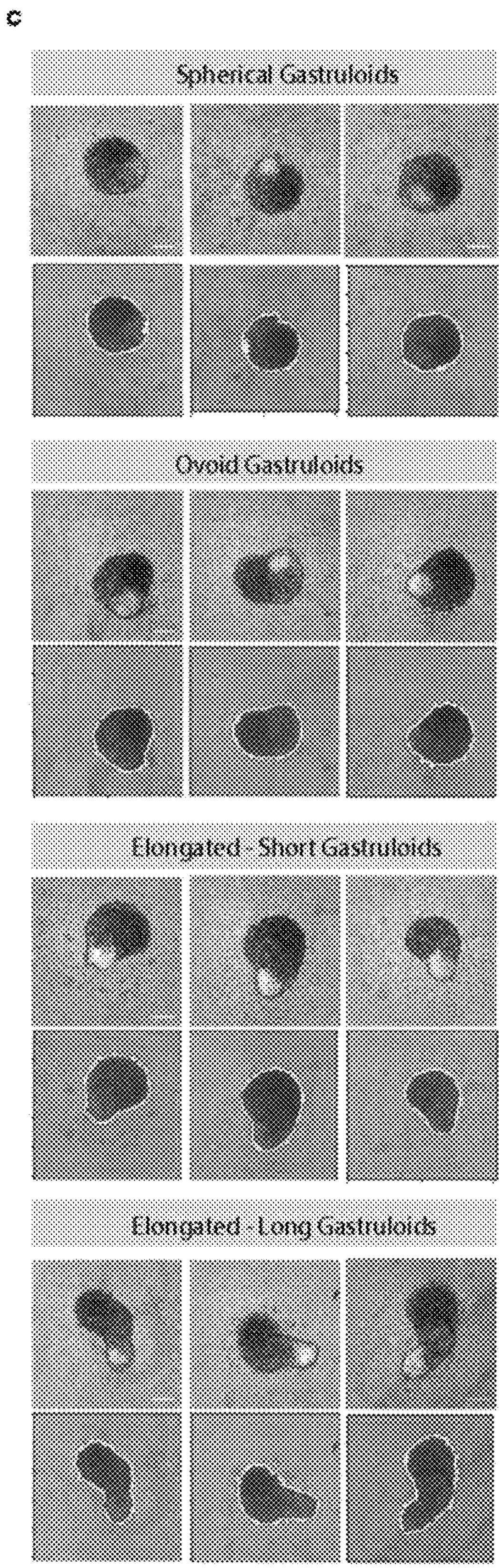
Figure 13:
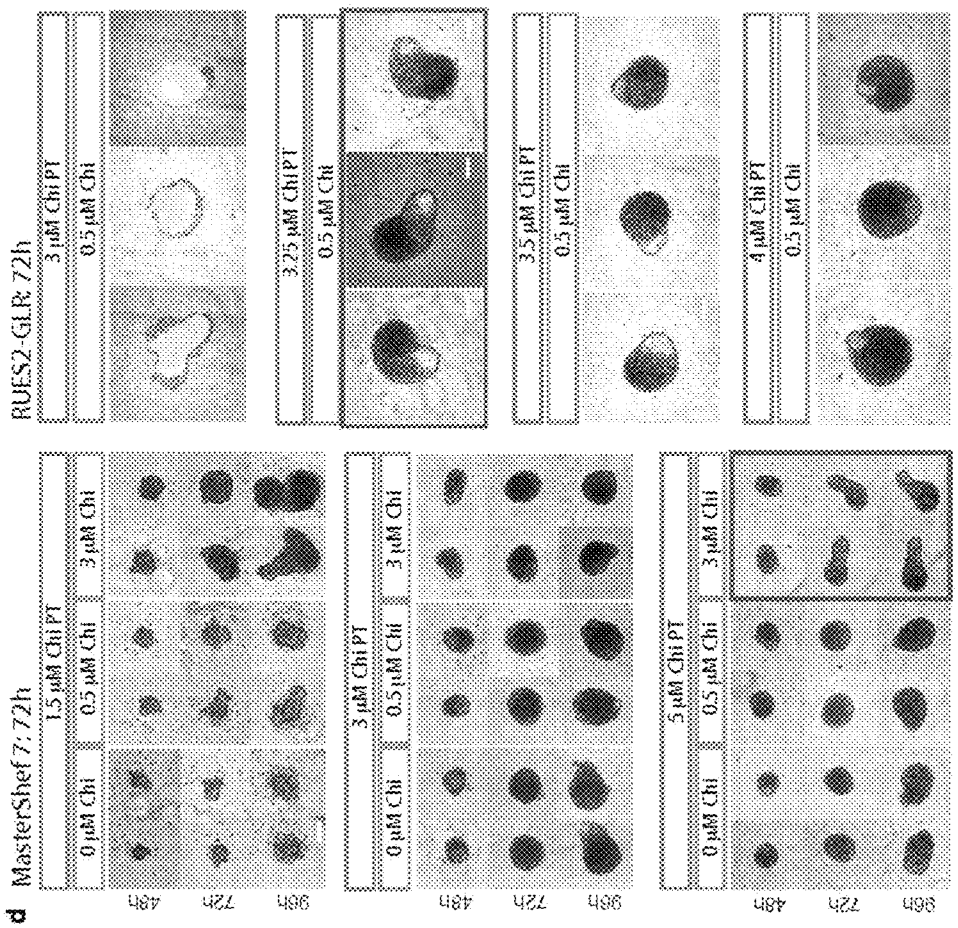
Figure 14:
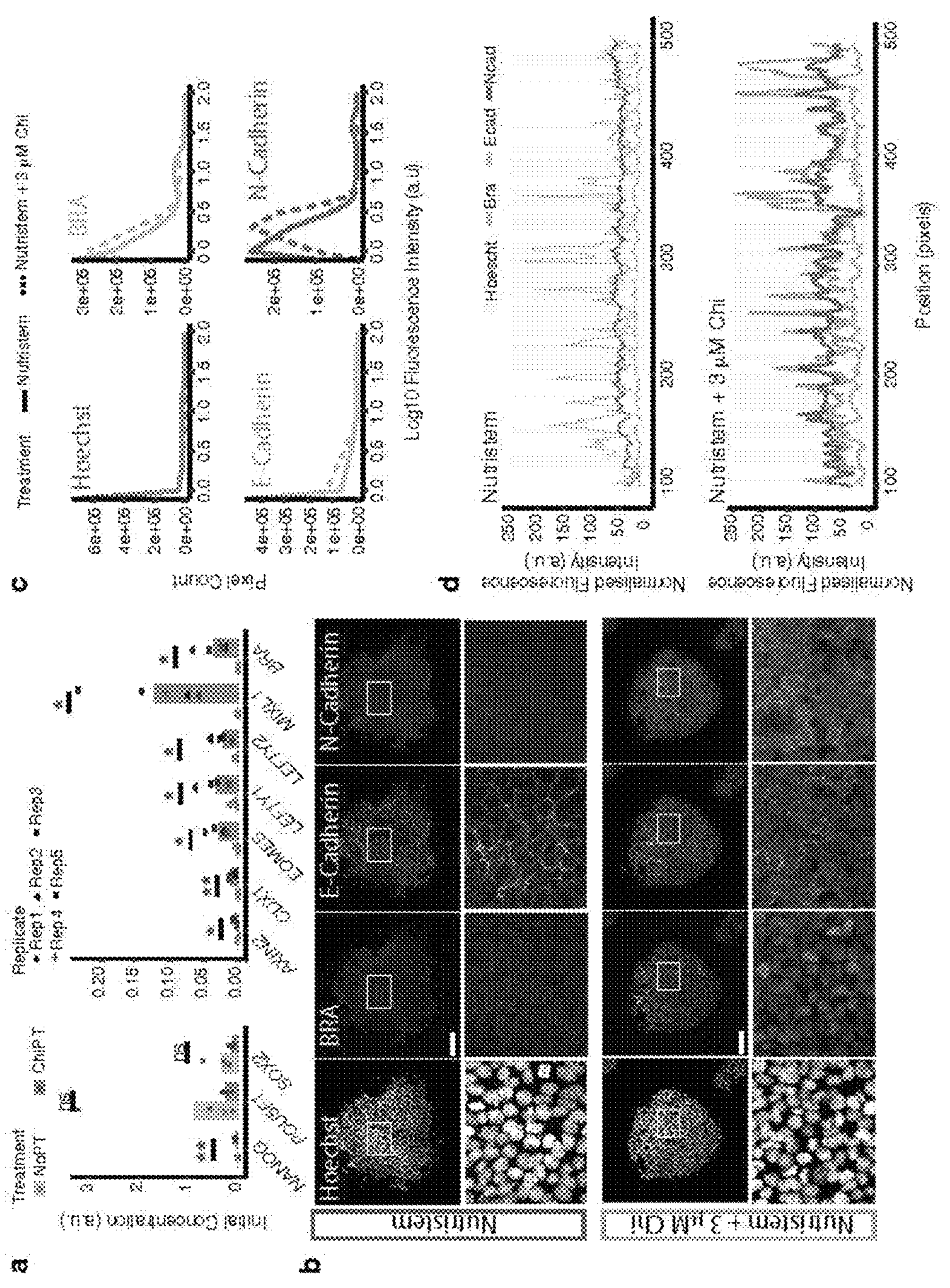
FIG. 14: Effect of Chiron pre-treatment on human embryonic stem cells. a, Gene expression following 24 hours of Chiron pre-treatment in adherent RUES2-GLR cells compared to non-pretreated cells in Nutristem alone, as assessed by RT-qPCR. Shown are averages from 5 biological replicates, bars show the mean average while points show technical averages for each experimental replicate. Significance (ns, $p>0.05$, *, $p<0.05$; , $p<0.01$; *, $p<0.001$) assessed by Welch two-sided t-Test (NANOG, $p=0.005904$, $t=-3.7774$, 7.6264 degrees of freedom, d.f.; POU5F1, $p=0.3309$, $t=1.1047$, d.f.=4.025; SOX2, $p=0.07455$, $t=2.3451$, d.f.=4.2888; AXIN, $p=0.02146$, $t=-3.4691$, d.f.=4.4642; CDX1, $p=0.00639$, $t=-5.2284$, d.f.=4.0001; EOMES, $p=0.01171$, $t=-4.3383$, d.f.=4.0864; LEFTY1, $p=0.03737$, $t=-2.9402$, d.f.=4.4306; LEFTY2, $p=0.02911$, $t=-3.2499$, d.f.=4.212; MIXL1, $p=0.01783$, $t=-3.8804$, d.f.=4.0003; BRA, $p=0.01735$, $t=3.9131$, d.f.=4). b, Immunostaining of adherent colonies of RUES2-GLR cells for BRACHYURY, E-CADHERIN and N-CADHERIN (CDH1 and CDH2 respectively) in routine Nutristem medium (top) or following 24 h Chiron (Chi) pre-treatment (bottom). Scalebar; 100 μm. Dotted region on colony (top panels) shows position of enlarged region (bottom panels). c, Histogram quantifying expression from immunostaining of RUES2-GLR cells, as shown in panel b. The whole image was used to generate this data. d, Profiles of membrane localisation of E- and N-cadherin from immunostaining of RUES2-GLR cell colonies, as shown in panel b. A line region of interest was drawn across the centre of each colony, and resultant fluorescence intensity plotted. Nuclear regions were inferred by fluorescence intensity of Hoechst over an arbitrary threshold. Nuclear regions are demarcated by pale blue bars, and peaks of cadherin expression tend to occur and inter-nuclear regions indicating membrane localisation.

Example 3—Further Analysis Regarding the Culture of Human Embryonic Stem Cells and Human Induced Pluripotent Stem Cells Using Methods of the Invention When hESCs were treated with Chiron, a Wnt agonist, for one day before seeding defined numbers of cells in low adherent plates in the presence of 3-3.5 μM of the Wnt signalling agonist, CHIR99021 (hereafter referred to as Chiron), they formed compact, spherical aggregates within a few hours that progressively broke symmetry to become ovoid by 24 hours after aggregation (h), and formed elongated structures by 48 h (FIG. 9*a, b*). This elongation was maximal at 72-96 h and was strictly dependent on the Chiron pre-treatment (FIG. 9*b-c* and FIG. 13*a-b*). After 72 h only some of the structures remained elongated until 96 h, when the majority tended to curl or retract. We observed that this elongation was reproducible in that, on average, ~66% of aggregates from each experiment displayed an elongated morphology at 72 h (FIG. 9*d* and FIG. 13*c*) with a smooth surface of cells along the exterior of the aggregate (FIG. 9*e*). Different cell lines required different concentrations of Wnt signalling stimulation, suggesting line-specific requirements (FIG. 13*d*). Before aggregation, pre-treated hESCs were found to still express the pluripotency markers POU5F1 (also known as OCT4) and SOX2 at levels comparable to cells maintained in pluripotency medium alone (Welch Two-sided t-Test, p=0.33 and 0.075 respectively; FIG. 14*a*) but with increased expression of NANOG (p=0.0059) and mesendodermal marker genes including BRA, MIXL1, LEFTY1, LEFTY2, AXIN2, EOMES, CDX1 (p=0.017, 0.018, 0.037, 0.029, 0.021, 0.012 and 0.0064 respectively; FIG. 14*a*). They also underwent an increase in the expression of membrane localised CDH2 (N-cadherin) from CDH1-based (E-cadherin) expression (FIG. 14*b-d*). These results suggest that following Chiron pre-treatment, hES cells become partially primed towards a primitive streak-like state and so, are in agreement with observations that Wnt signalling induces mesodermal differentiation of hESCs.

Figure 15:
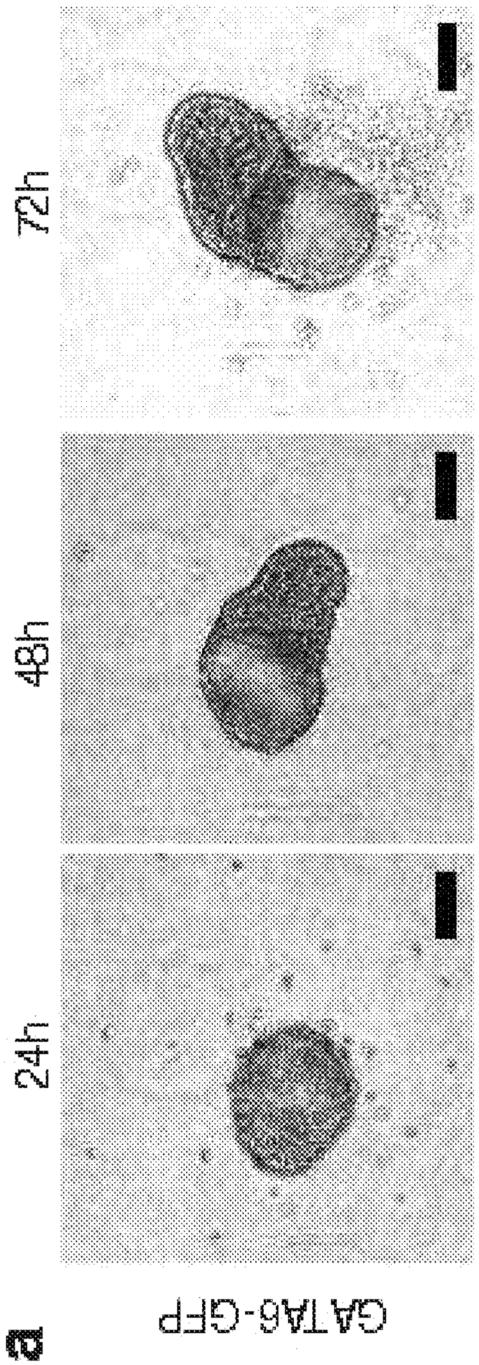
FIG. 15: Establishing and disrupting axial patterning in human gastruloids. a, Progressive polarisation and restriction of GATA6-GFP fluorescence to the anterior pole of human gastruloids made from the S4-GATA6-GFP cell line. Scalebar; 100 μm. b, Immunofluorescence imaging of RUES2-GLR human gastruloids, stained for BRA and SOX2 expression, showing polarised expression as early as 24 h. Shown are confocal sections (top) and mean projection (bottom) of the gastruloids. Scalebar; 100 μm. c, Human gastruloids made from MasterShef7 cell line at 72 hours after aggregation, showing BRA, SOX2 and N-Cadherin (CDH2) localisation. Shown are 3 representative examples. Scalebar; 100 μm. d, Pre-treatment with Wnt3a instead of Chiron for 24 h in RUES2-GLR cells is insufficient to promote elongation or BRA expression. Dark green bounding box indicates the pre-treatment condition in Nutristem, and teal box indicates the aggregation medium composition in E6 and ROCK inhibitor. Shown are 2 representative examples from each condition. Scalebar; 100 μm. e, Pre-treatment with BMP4 instead of Chiron for 24 h in RUES2-GLR cells is insufficient to promote elongation or BRA expression. Shown are 2 representative examples from each condition. Dark green bounding box indicates the pre-treatment condition in Nutristem, and teal box indicates the aggregation medium composition in E6 and ROCK inhibitor. Scalebar; 100 μm. f, Application of a BMP inhibitor, LDN193189 (LDN; left) or Tankyrase inhibitor, XAV-939 (XAV; right) during 24 h pre-treatment of RUES2-GLR cells. Shown are 2 representative examples from each condition. Dark green bounding box indicates the pre-treatment condition in Nutristem, and teal box indicates the aggregation medium composition in E6 and ROCK inhibitor. Scalebar; 100 μm. g, Application of a Nodal signalling inhibitor, SB43 (SB43) during 24 h pre-treatment of RUES2-GLR cells. Shown are 2 representative examples from each condition. Dark green bounding box indicates the pre-treatment condition in Nutristem, and teal box indicates the aggregation medium composition in E6 and ROCK inhibitor. Scalebar; 100 μm.
Figure 15:
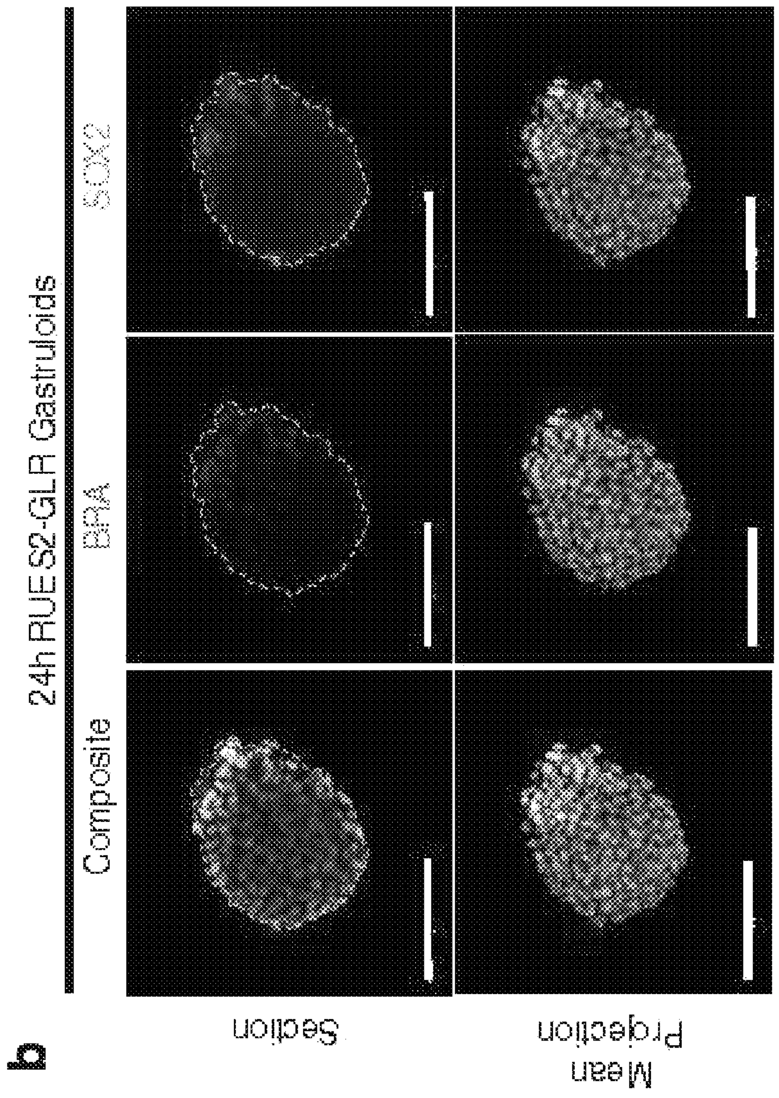
Figure 15:
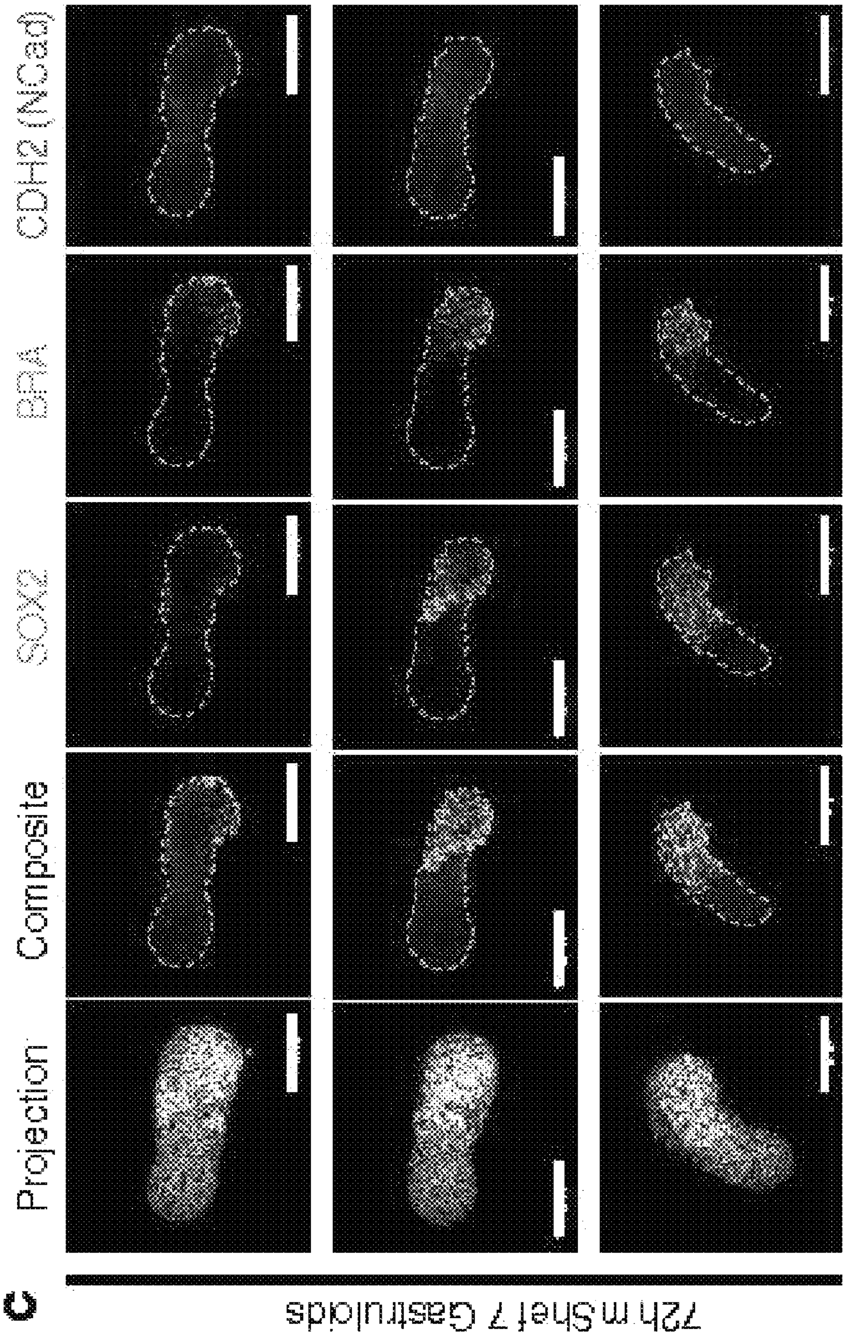
Figure 15:
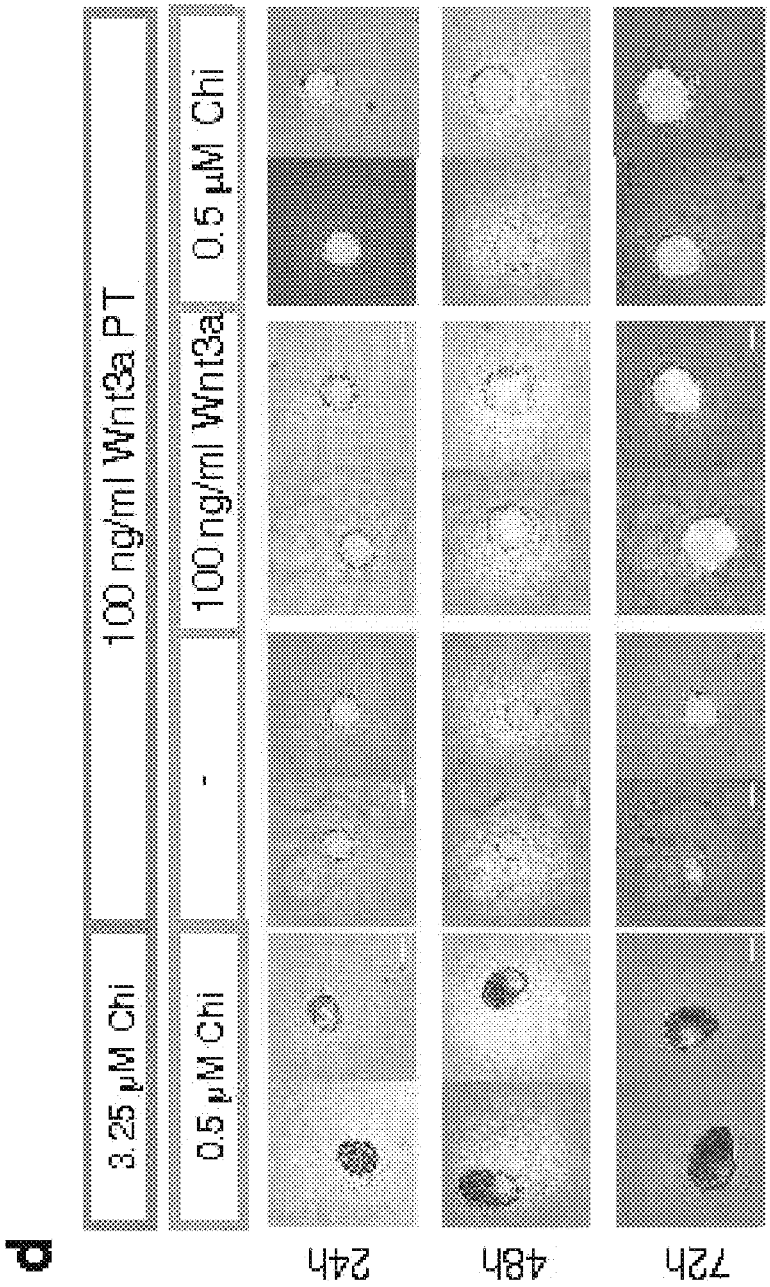
Figure 15:
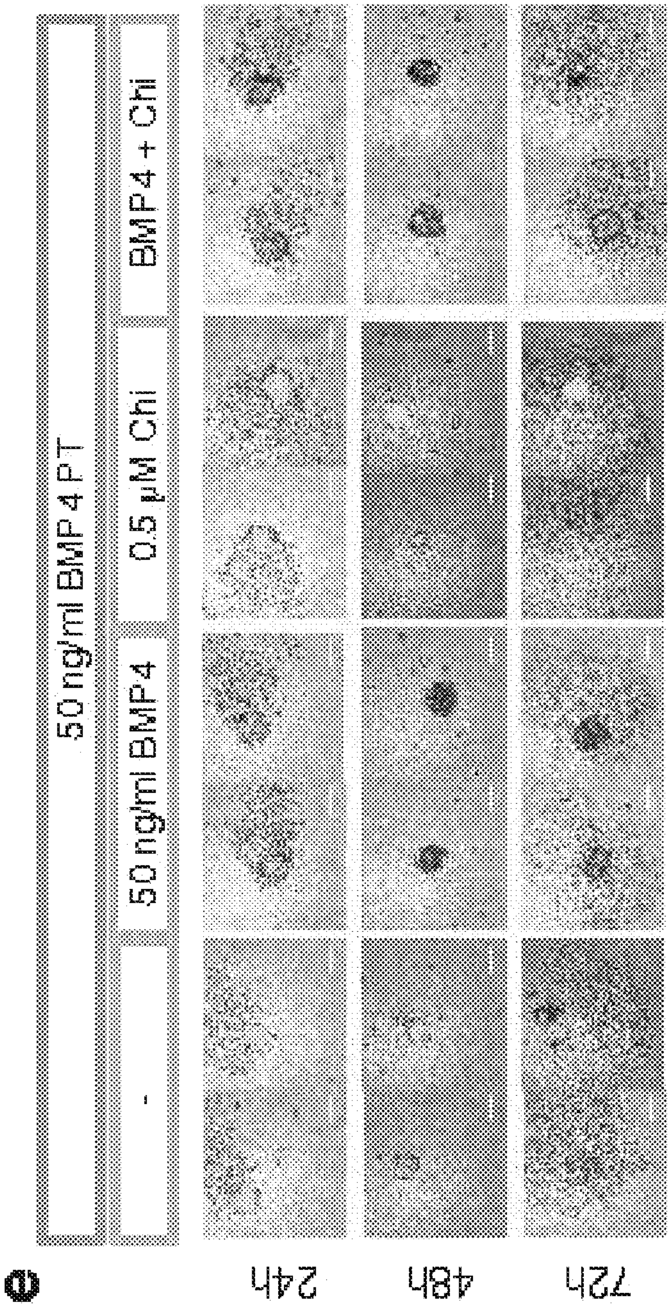
Figure 15:
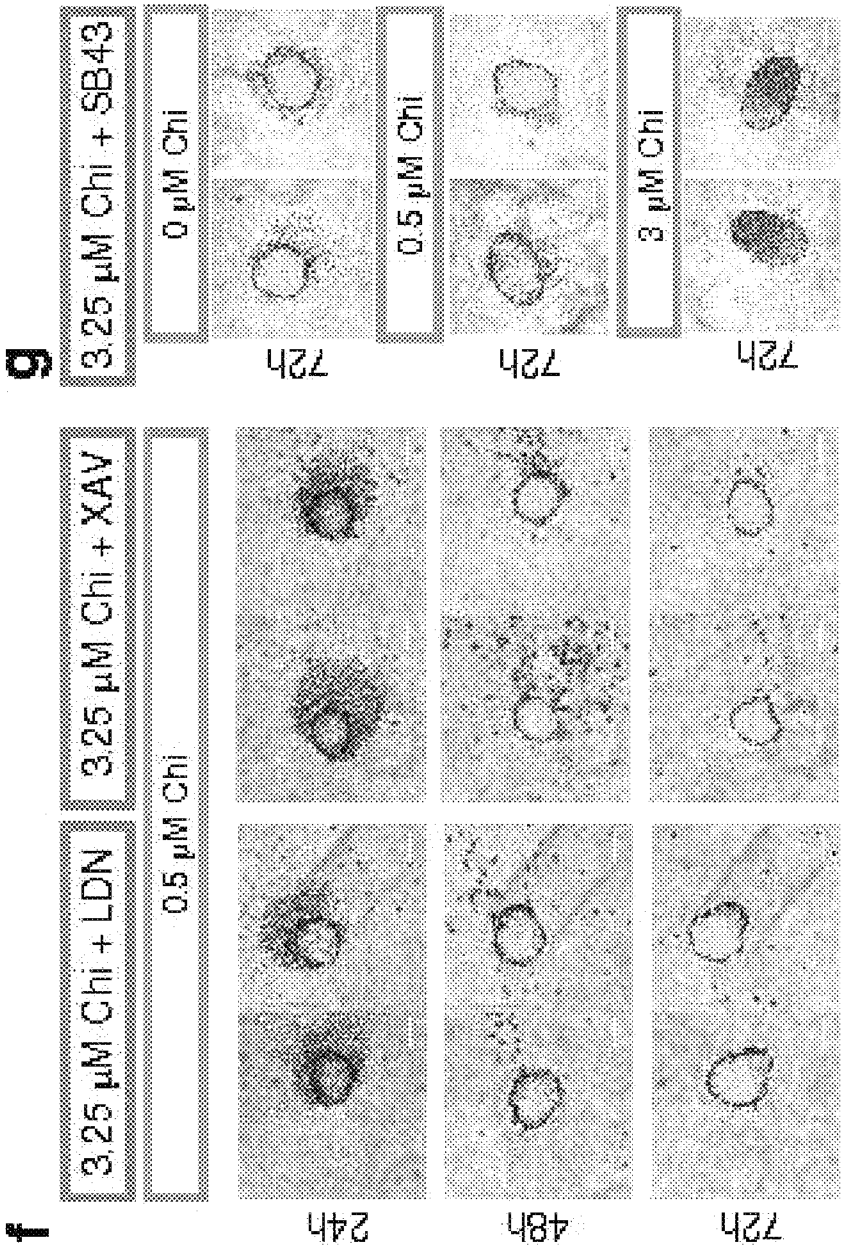

These elongated structures bear a remarkable resemblance to mouse embryonic stem cell-derived gastruloids which, as well as displaying an elongated morphological structure, exhibit expression of differentiation genes patterned along defined axes. In order to test whether these elongated structures are similar in this respect to mouse gastruloids, we stained 72 h elongated aggregates for differentiation markers, and noticed a clear anterior-posterior distinction between the two ends: at the BRA expressing end, we observe an overlap of expression with CDX2 and, at the other end, there is a domain expressing GATA6 (FIG. 9*f*); the polarisation of GATA6 to the anterior end was also confirmed using a reporter system (FIG. 15*a*). The BRA/CDX2 expressing cells are located at the tip of the elongating structure and, as in the embryo this combination identifies the caudal-most region of the embryo, which we believe that it is the same in the gastruloid. This polarised region of BRA was also positive for CDH2 (N-cadherin) and overlapped with a SOX2 positive region at 72 hours, but gradually resolved to distinct BRA and SOX2 expression domains (FIG. 9*f*). These frequently appeared to be arranged such that the BRA and SOX2 domains were separated along an axis that was roughly orthogonal to the AP axis, suggesting the presence of at least 2 axes. In a proportion of aggregates, we also observed internal morphological structures that appeared to show epithelial rosette-like or lumen-like structures at the most posterior end (FIG. 9*g*). Because of the elongated morphology, polarised BRA expression and similarity to mouse gastruloids that is initiated from a human ESC population, we have termed these structures human gastruloids.

However, in order to ascertain whether these human gastruloids are indeed capable of generating organised derivatives of the three germ layers, as occurs during gastrulation, we made use of a germ layer reporter line (RUES2-GLR; Martyn et al., 2018). This hESC line utilises fluorescent reporters of the BRA (mesoderm), SOX17 (endoderm and primordial germ cells) and SOX2 (neuroectoderm) marker genes, which allows dynamic assessment of germ layer generation and organisation (FIG. 2*a*). Human gastruloids made with this cell line initially express SOX2 due to their pluripotent status before aggregation (FIG. 2*b*). They then rapidly polarise the expression of SOX2 to one coherent domain at the end of the aggregate, with individual SOX17 expressing cells appearing throughout the remaining portion of the aggregate (FIG. 2*c*). Between 24 and 48 hours after aggregation, the aggregate undergoes an elongation, as BRA becomes localised to the SOX2 positive region of the gastruloid (FIG. 2*d*). By 72 hours after aggregation, the elongated gastruloid expresses BRA at the posterior-most portion of the elongation, with neighbouring SOX17 and SOX2 expressing domains adjacently (FIG. 2*e*).

Altogether these observations suggest that the hESC derived gastruloids develop a structure similar to that of mouse gastruloids and exhibit an outline of axial organization. To explore further the complexity and organization of these gastruloids, we decided to analyse the transcriptional profile of human gastruloids using TOMO-sequencing (TOMO-seq), a technique that allows to sample the spatial organization of transcription at the whole genome level (Junker et al., 2014 and Kruse et al., 2016). Gastruloids at 72 hours after aggregation were fixed, embedded for sectioning along their AP axis and subjected to RNAseq analysis (FIG. 10*a*-*b*).

Figure 10:
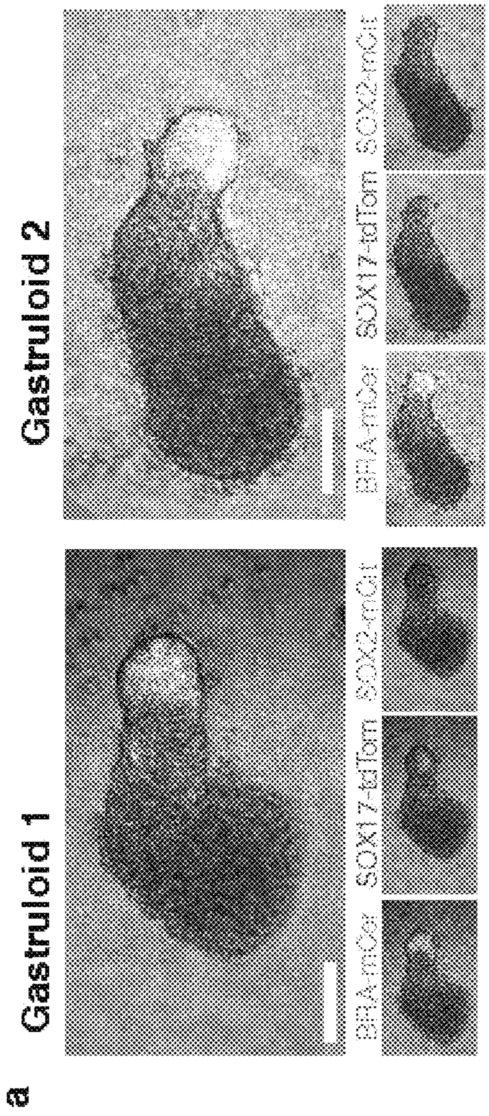
FIG. 10: Transcriptomic Anterior-Posterior organization of human gastruloids. Widefield imaging of the two 72 h RUES2-GLR derived Chiron pre-treated human gastruloids used for tomo-sequencing. Scale bars; 100 μm. mCer, mCerulean; tdTom, tdTomato; mCit, mCitrine. b, Detection of the mRNA of the fluorescent reporter transgenes integrated into the RUES2-GLR line by normalized expression. c, Transcriptomic analysis of 1,023 significantly reproducible genes plotted along the anterior-posterior (AP) axis of two 72 h RUES2-GLR derived Chiron pre-treated human gastruloids. Coloured panels (left) show the hierarchical clustering of gene expression behavior along the AP axis for the two gastruloids. The two replicates are shown. d, Examples of the AP gradients of selected clusters, and some of their enriched Gene Ontology (GO) terms. Overlaid number in each panel corresponds to the number of genes observed within that cluster. Shaded ribbon corresponds to the standard deviation of the cluster profile across all genes within the cluster. e, Scaled gene expression along the AP axis using characteristic markers of all three germ layers. Selected genes are highlighted. Colour-scale equivalent to that of panel c. f, Localisation of HOX gene expression along the AP axis, by scaled z-score. White bars indicate lack of that paralogue in the genome, while the dark blue indicates levels below the limits of detection.
Figure 10:
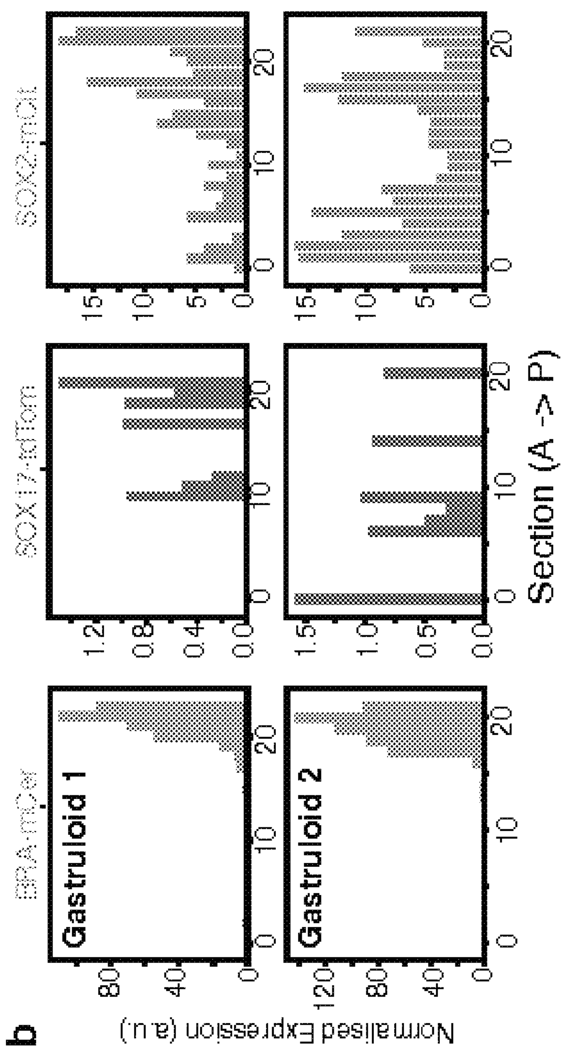
Figure 10:
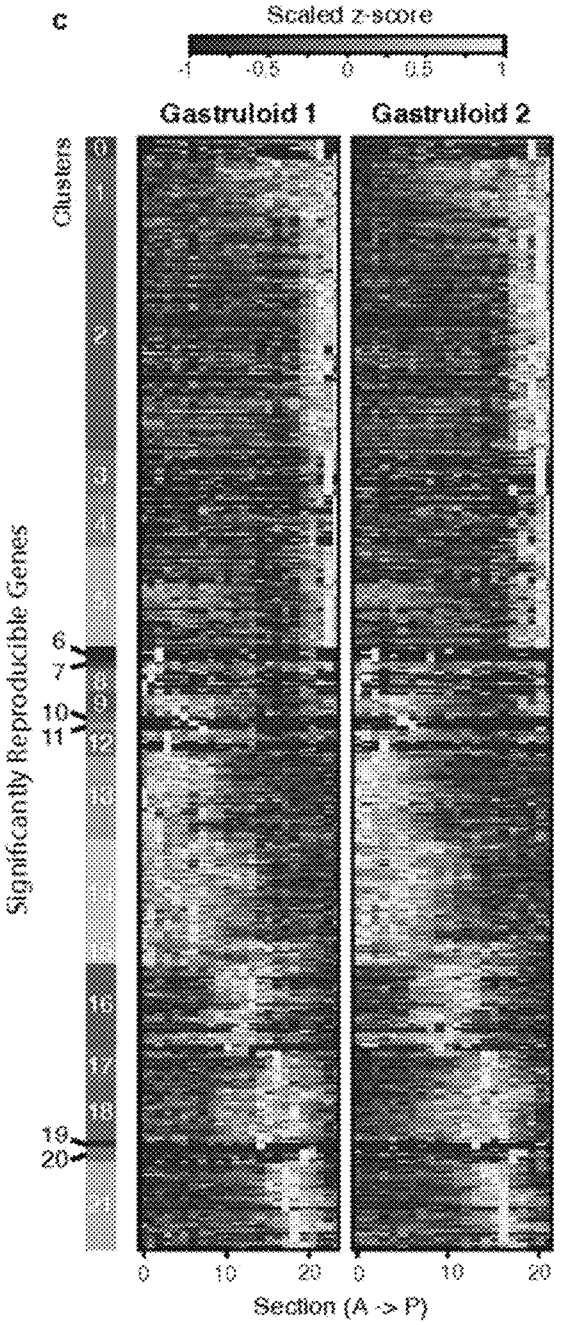
Figure 10:
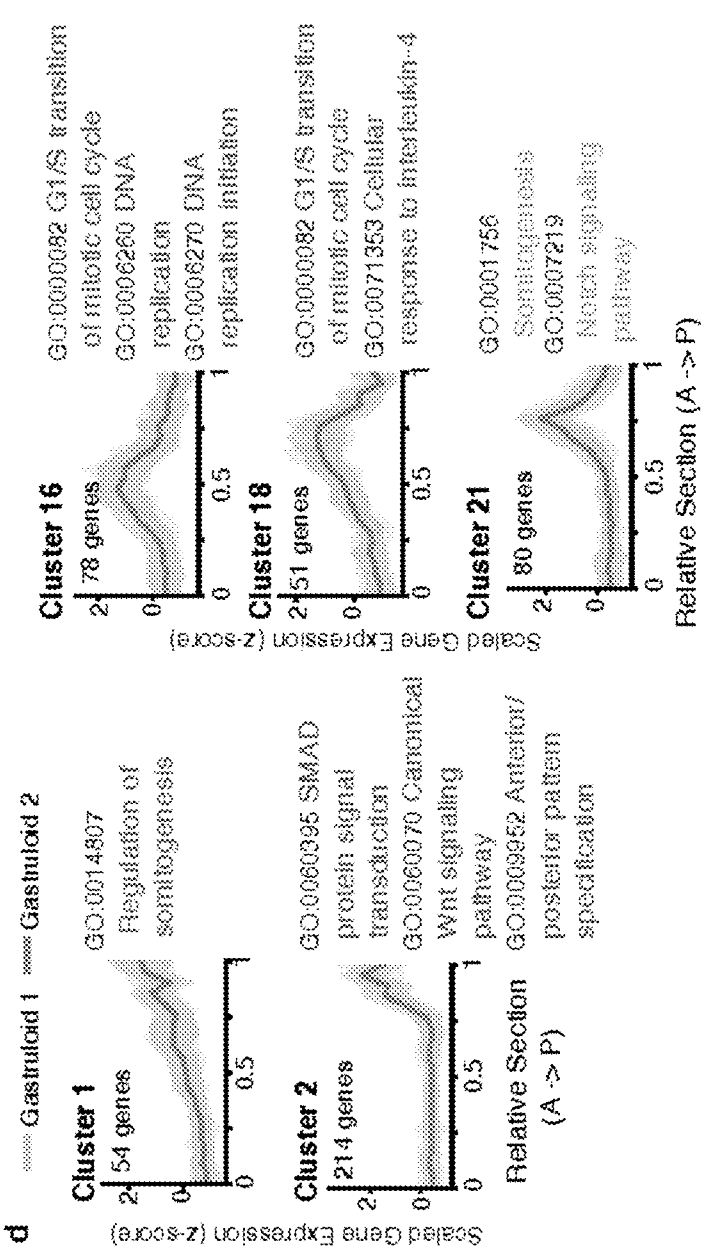
Figure 10:
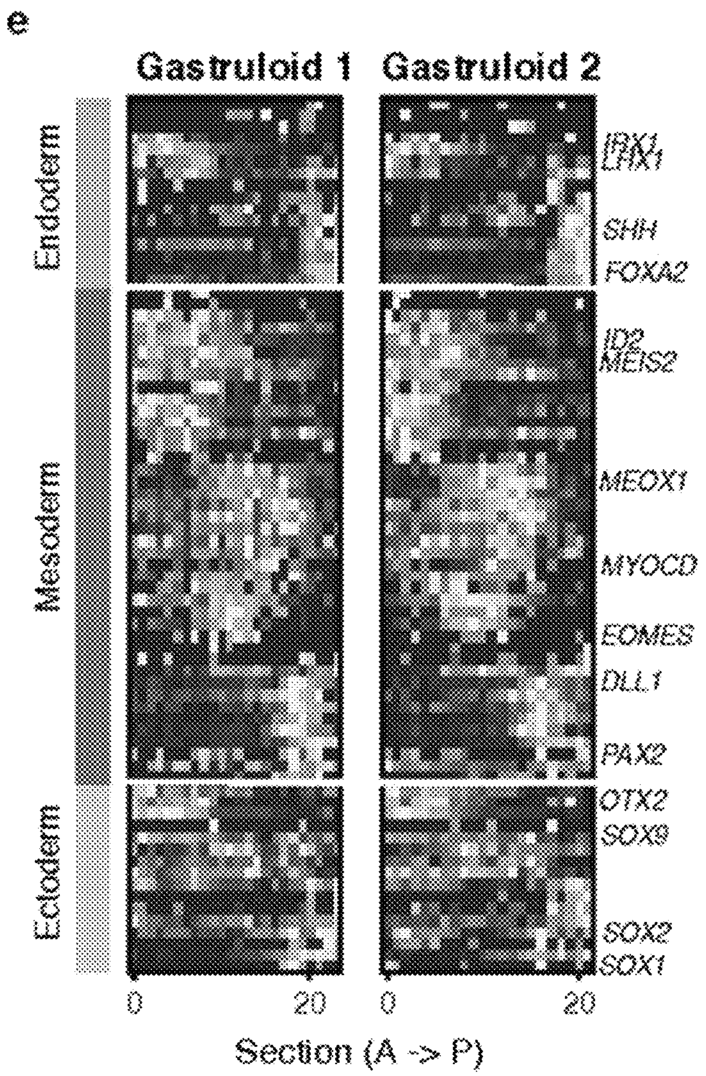
Figure 10:
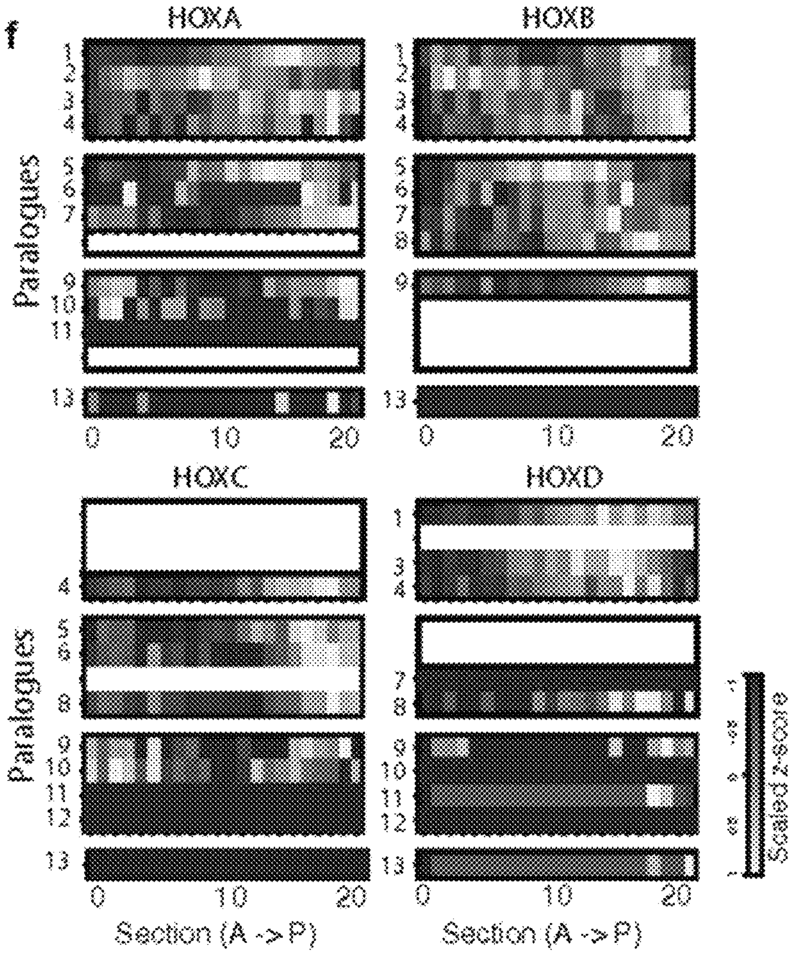

When all genes were assessed for spatial localisation along the AP axis, we found 22 classes of gene expression (FIG. 10*c*-*d* and FIG. 16). Six clusters (Clusters 0-5), that were localised to the posterior-most region of the gastruloid, contained genes that are localized to the tail bud in the mouse embryo, including BRA, CDX2, and CYP26A1. At the opposing end we observed 9 clusters (Clusters 6-14), containing genes including KDR, SOX4, MEIS1/2, PBX1, TWIST1, ISL1, IRX1/2/3, JARID2 and PRDM1 (FIG. 10*c, d*).

Additionally, we observed 7 further clusters of genes (Clusters 15-21) located at intermediate positions of the AP axis (FIG. 10*c, d*), containing genes including many expressed in the trunk region of mammalian embryos, such as PAX3, TCF15, DKK1, MEOX2 (Cluster 16), RALDH2 (ALDH1A2), ZIC2, MEOX1 Cluster 18), WNT5A, DLL3, CITED1, MESP1, RIPPLY2 and PTCH1 (Cluster 21; FIG. 10*c, d*). Cluster 21 was strongly enriched for genes involved in somitogenesis (GO:0001756, Benjamini-corrected p-value=0.0135) and the Notch signalling pathway (GO: 0007219, p-value=0.0375).

Figure 17:
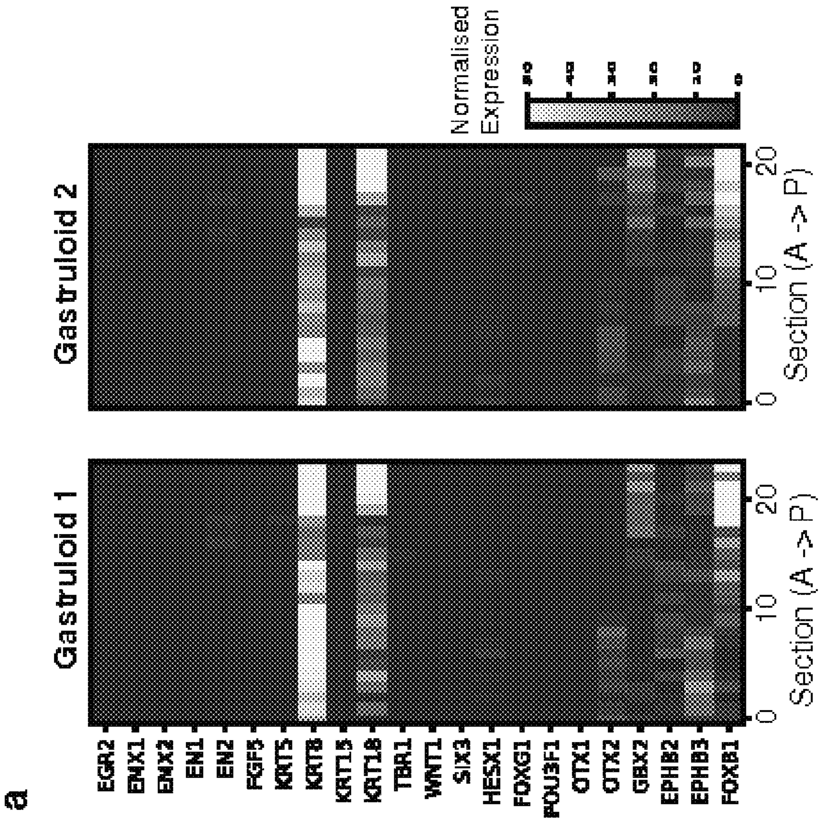
FIG. 17: Transcriptional profiles and anterio-posterior (AP) localisation in human gastruloids. a, Normalised expression of anterior neural genes in human gastruloids, show generally low levels of expression. Those with higher expression levels are likely because of cell types associated with epidermal fates (KRT8 and KRT18) and the tailbud region (GBX2, FOXB1). b, Total expression (log 10 transformed) of each HOX gene across all sections of Gastruloid 1 (upper) and Gastruloid 2 (lower), for all 4 clusters (HOXA, HOXB, HOXC and HOXD) and many of the 13 paralogues. White boxes indicate that a gene is not present in the human genome. c, Expression of ligands of the BMP (top) and WNT (bottom) signalling pathways. Red box indicates genes with particularly strong AP localisation bias. d, Widefield images of human gastruloids at 72 h made from the SMAD1-RFP; H2B-mCitrine cell line. Three representative examples are shown. Scalebar; 100 μm. e, Confocal images of live human gastruloids at 72 h made from the SMAD1-RFP; H2B-mCitrine cell line. Sections through the gastruloid (left) and maximum projections (Max Proj.; right) show that SMAD1-RFP cells can be observed throughout the gastruloids. Three representative examples are shown by maximum projection. Scalebar; 100 μm. f, Immunostaining of LEF1 and BRA expression in 96 h RUES2-GLR human gastruloids. LEF1 is localised in a gradient primarily in the posterior portion of the gastruloids. Shown are two representative examples. Scalebar; 100 μm. g, Immunostaining of WNT3A and BRA expression in 72 h RUES2-GLR human gastruloids, showing close-up of posterior end. Shown is one representative example. Scalebar; 50 μm. Max Proj; Maximum Projection. h, Localised expression of Nodal signalling-related genes towards the posterior of Chiron pre-treated human gastruloids by tomo-sequencing.
Figure 17:
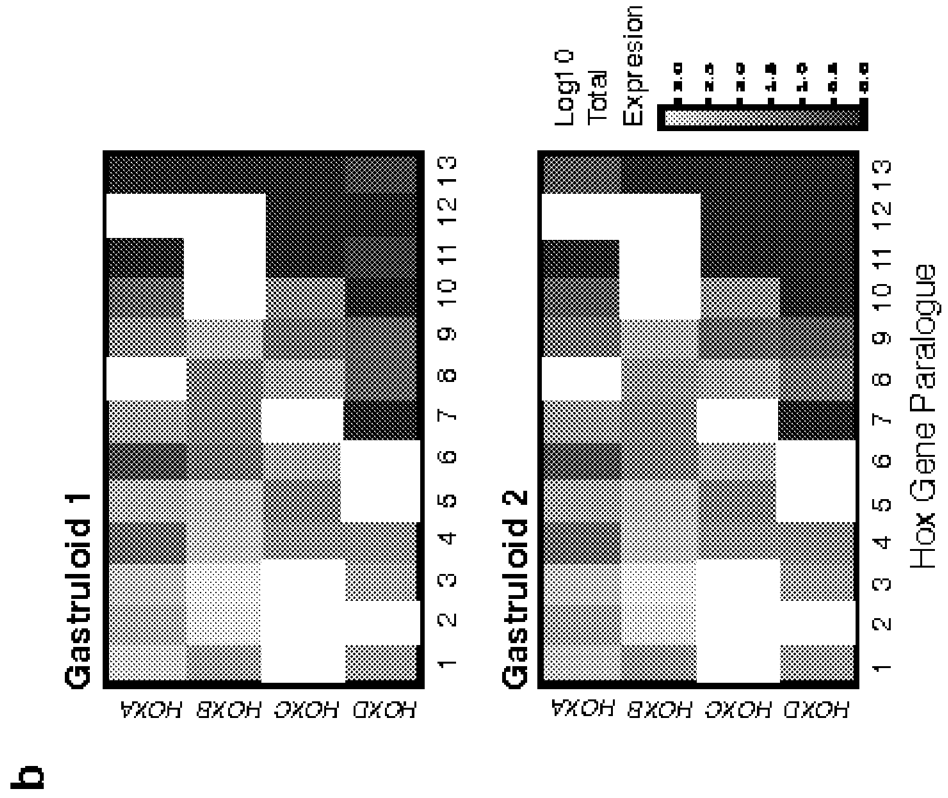
Figure 17:
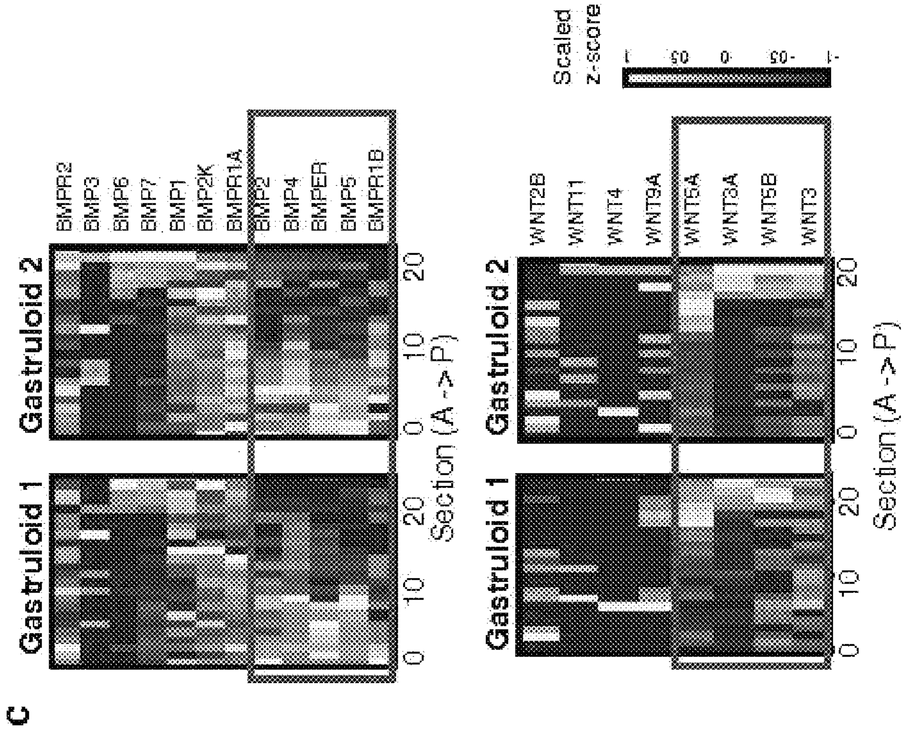
Figure 17:
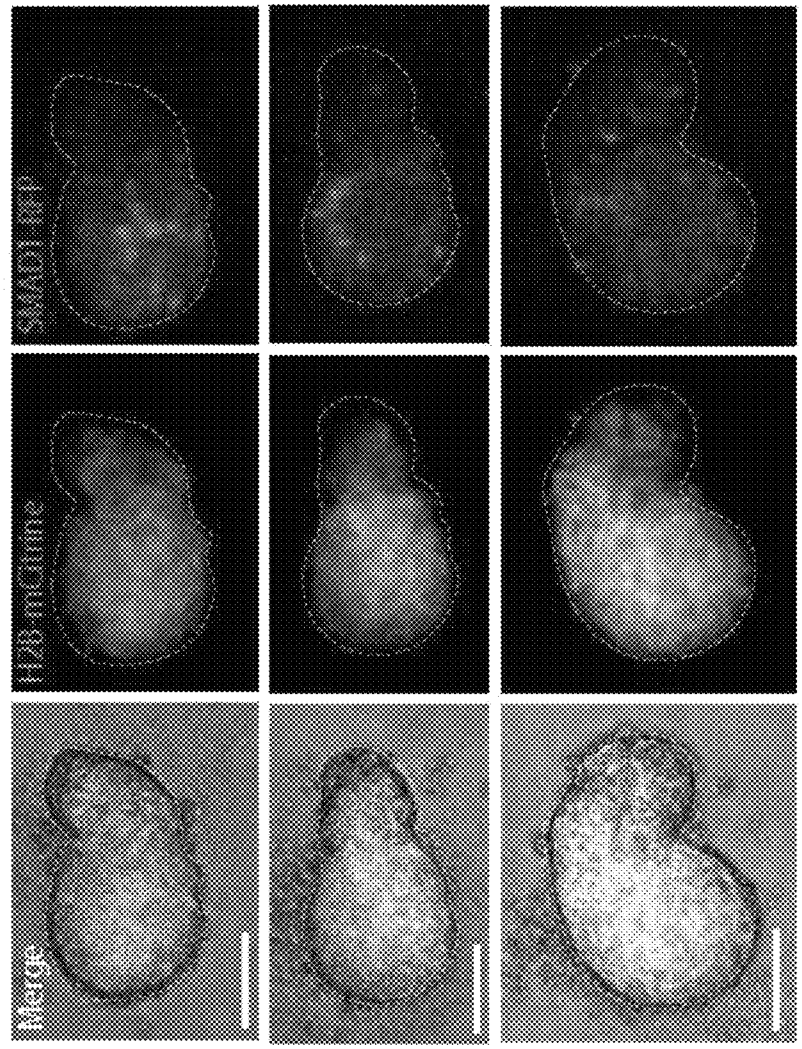
Figure 17:
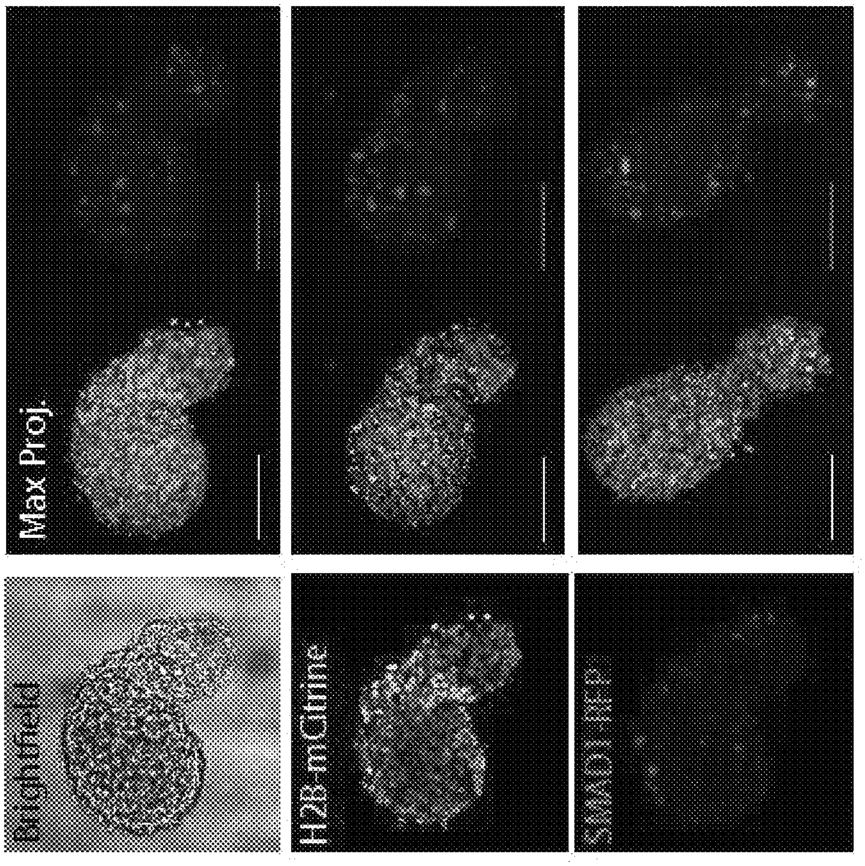
Figure 17:
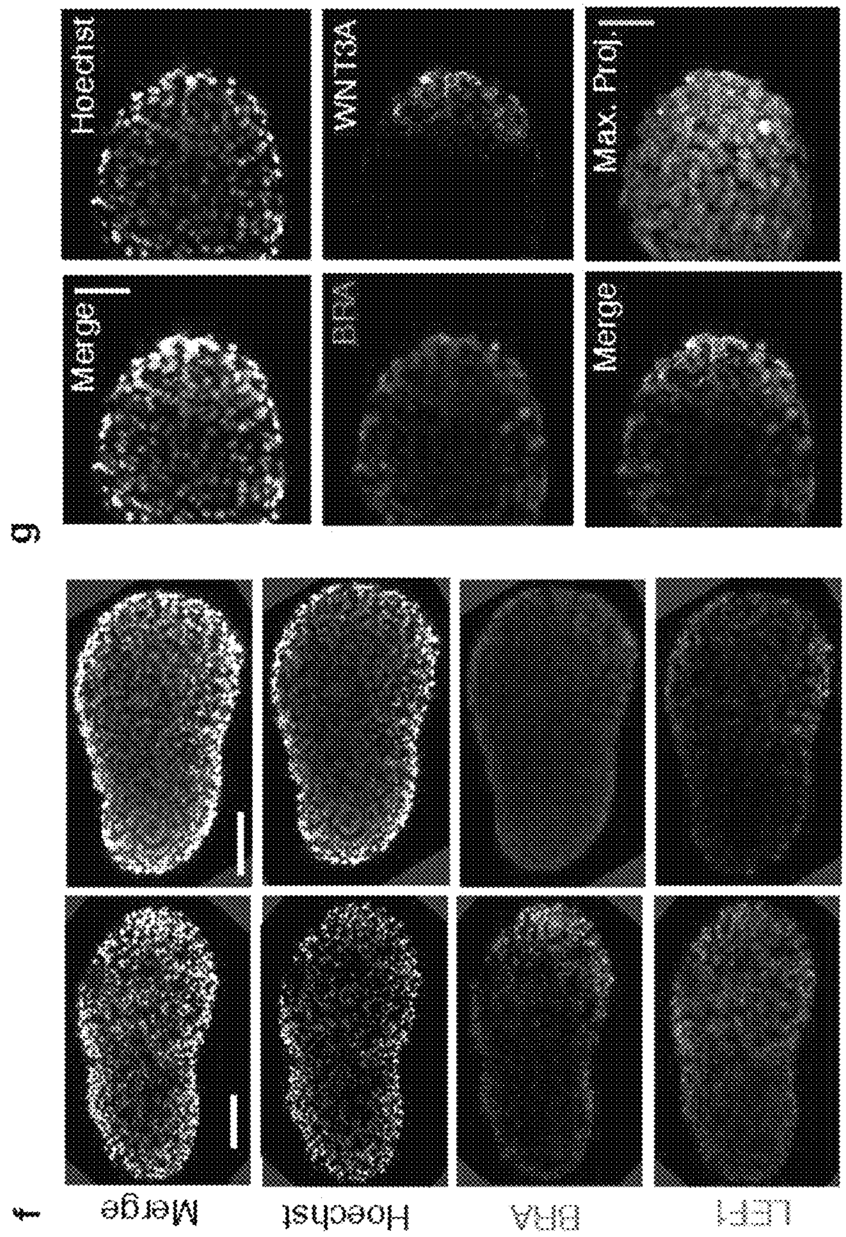
Figure 17:
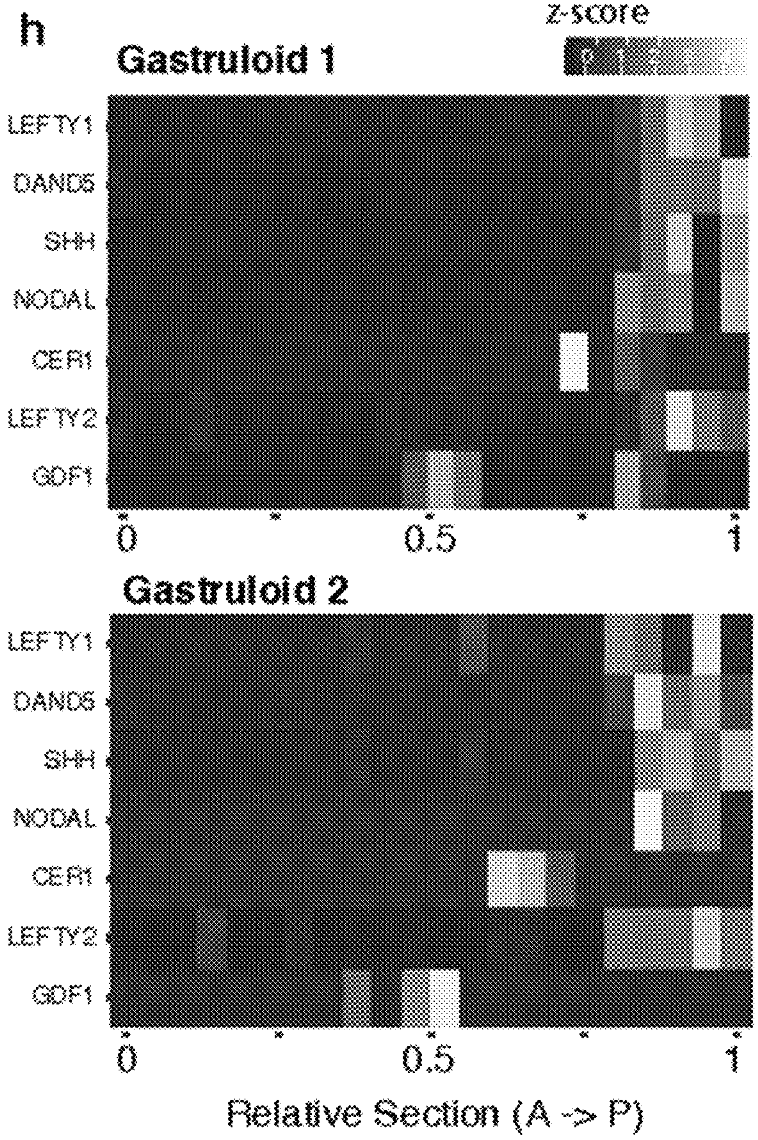

Throughout the AP axis we observed expression of genes associated with mesoderm, endoderm and ectoderm, indicating that cell types associated with all three germ layers are represented in the human gastruloids (FIG. 10*e*). We did not find evidence for the expression of genes associated with the development of anterior neural structures (FIG. 17*a*) but observed expression of many paralogues from the 4 HOX clusters (FIG. 17*b*). These HOX genes showed variable expression domains along the length of the gastruloid AP axis, including a broader domain of paralogues 1-5, and more posterior-biased distribution of later paralogues, including groups 5-8 and 9-13 (FIG. 10*f*). This pattern of HOX gene expression along the length of the AP axis indicates an ongoing, active process of axial extension.

We also observed a number of Wnt ligands expressed at the posterior-end (WNT5A, WNT3A, WNT5B and WNT3) and some BMP ligands anteriorly (BMP2, BMP4 and BMP5; FIG. 17*c*). These transcriptional patterns are reminiscent of the organization of signalling in mouse embryos and led us to examine whether the related signalling pathways were also active. In gastruloids made up from the BMP reporter line RUES2:SMAD1-RFP; H2B-mCitrine, SMAD1-RFP localised principally to the anterior domain, but with some positive cells scattered throughout their length, indicating activity of the BMP ligands (FIG. 17*d*-*e*). At the posterior end we observed expression of WNT3a in the peri-cellular space, indicating ligand secretion, and expression of LEF1 (a target of WNT/R-CATENIN signalling) within an adjacent domain, indicating Wnt signalling (FIG. 17*f*-*g*). Additionally, we observed a peak of Nodal signalling components and targets within the most posterior region of the gastruloids, including NODAL, LEFTY1/2 and CER1 (FIG. 17*h*). These results suggest that human gastruloids display inverted gradients of BMP and Wnt/Nodal signalling along their long axis.

Figure 11:
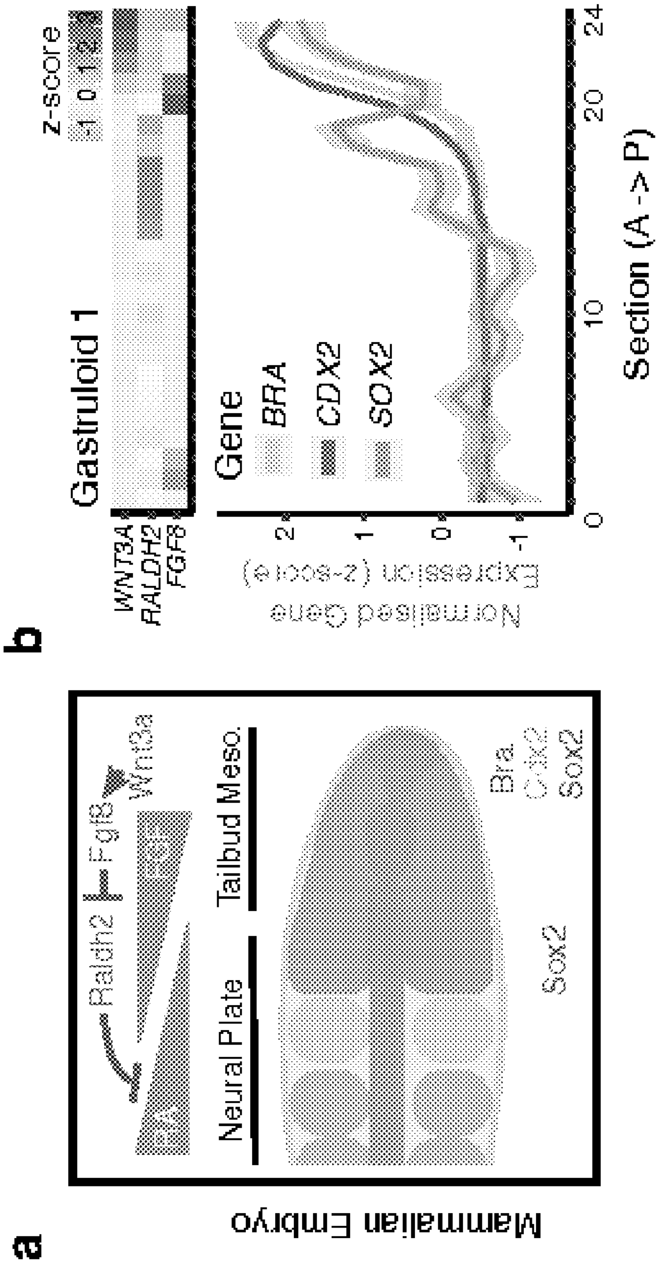
FIG. 11: Comparative elements of early embryogenesis using gastruloids as in vitro models. a, Schematic representation of the mammalian embryo morphology and gene expression for the tailbud. b, AP organization of tailbud-associated genes in human gastruloids. Heatmaps (upper) represent expression of signaling components and broad-domain transcription factors, while line graphs (lower) represent additional gene expression localisation. Line graphs are displayed as smoothened gene expression patterns (loess method) with 50% Confidence Interval indicated by a grey ribbon. Only one of the replicates of human gastruloids is displayed. c, Schematic representation of the mammalian embryo morphology and gene expression for the node region. d, AP organization of node region-associated genes in human gastruloids. Panel organized as in panel c. e, Immunostaining of 72 h Chiron pretreated human gastruloids from RUES2-GLR line, showing posterior localization of FOXA2 expression within a defined domain. Three representative examples are shown. Scale bars; 100 μm. f, Close-up of FOXA2-expressing domain, showing co-expression of FOXA2 and NOTCH1 Intercellular Domain (NICD; below). Two representative examples are shown. Scale bars; 10 μm. Dashed bounded lines indicate NOTCH1 NICD-expressing cells. g, Schematic representation of the mammalian cardiac mesoderm region. h, AP organization of cardiac mesoderm region-associated genes in human gastruloids. Panel organized as in panel c. i, In situ hybridisation of HOX gene paralogues in 72 h human gastruloids made from RUES2-GLR cells. Shown are representative examples for each gene. Scalebar; 200 μm.
Figure 11:
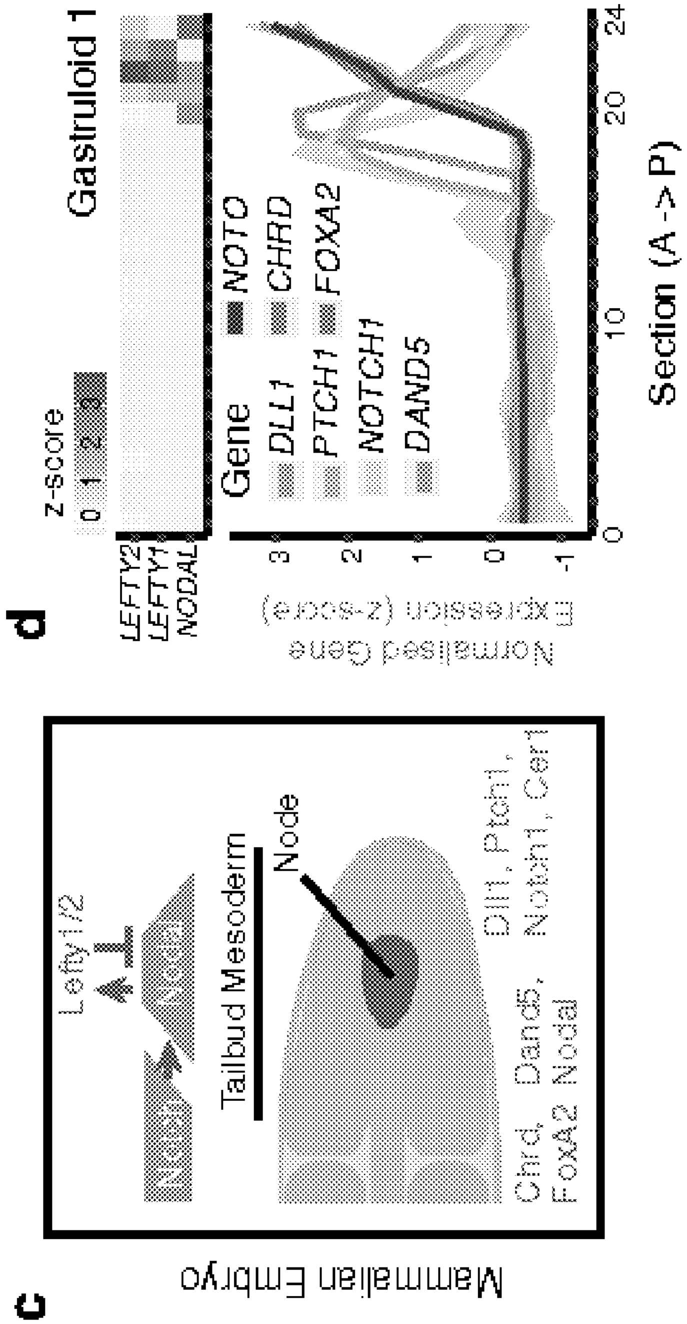
Figure 11:
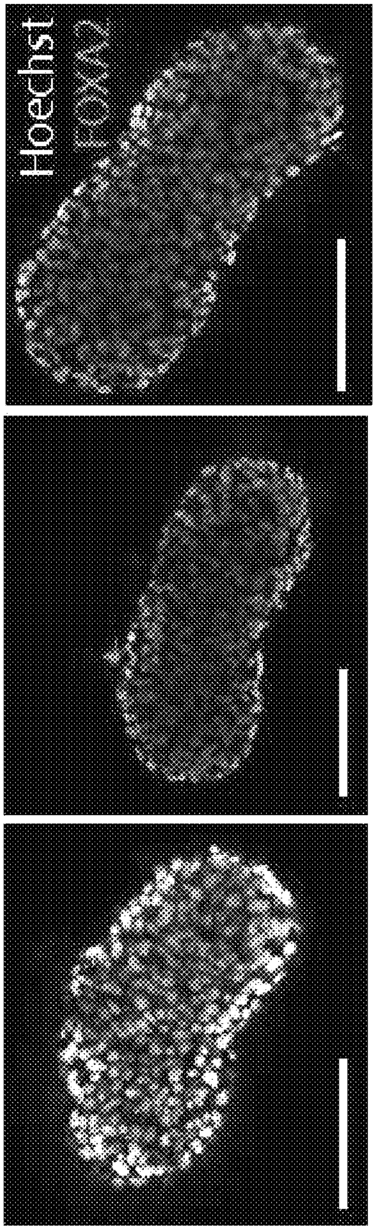
Figure 11:
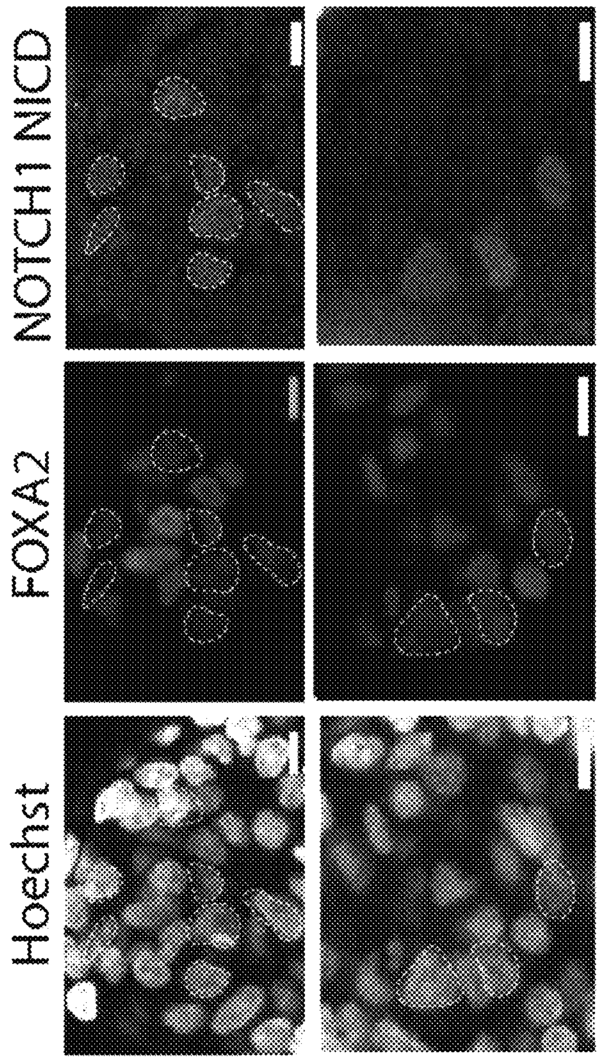
Figure 11:
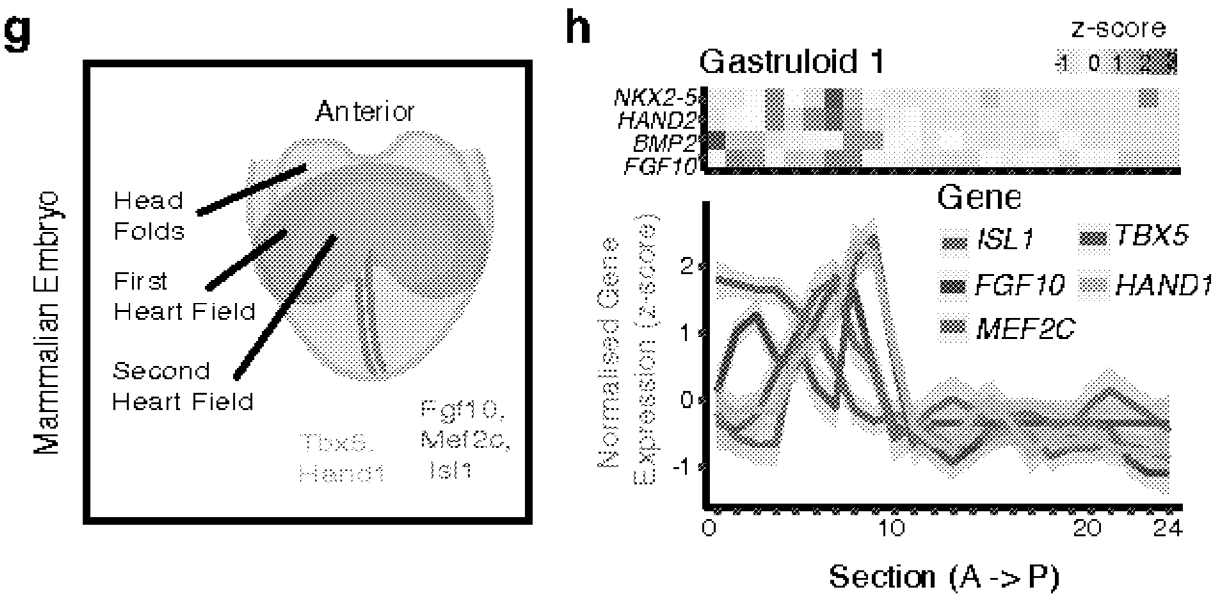
Figure 11:

The organization of the posterior domain of gene expression in the human gastruloids resembled the pattern in the tailbud region (FIG. 11*a*-*b*). Within this region, we observed a node-like transcriptional domain with overlapping expression of SHH, BMP7, CHRD, CELSR1 and DAND5, with neighbouring peaks of DLL1, NOTCH1 and PTCH1 (FIG. 11*c*-*d*), and a local domain of NOTCH signalling around FOXA2 expressing cells (FIG. 11*e*-*f*). At the opposite end, we observe a pattern associated with cardiac mesoderm development, as reflected in the coincident expression of BMP2 with peaks of FGF8 and FGF10, overlapped by domains TBX1/5, HAND1/2, NKX2.5, MEF2C and ISL1 expression (FIG. 11*g*-*h*). This is accompanied by the anterior-posterior expression of HOX genes, including HOXB3, HOXC8 and HOXB9 (FIG. 11*i*).

Figure 12:
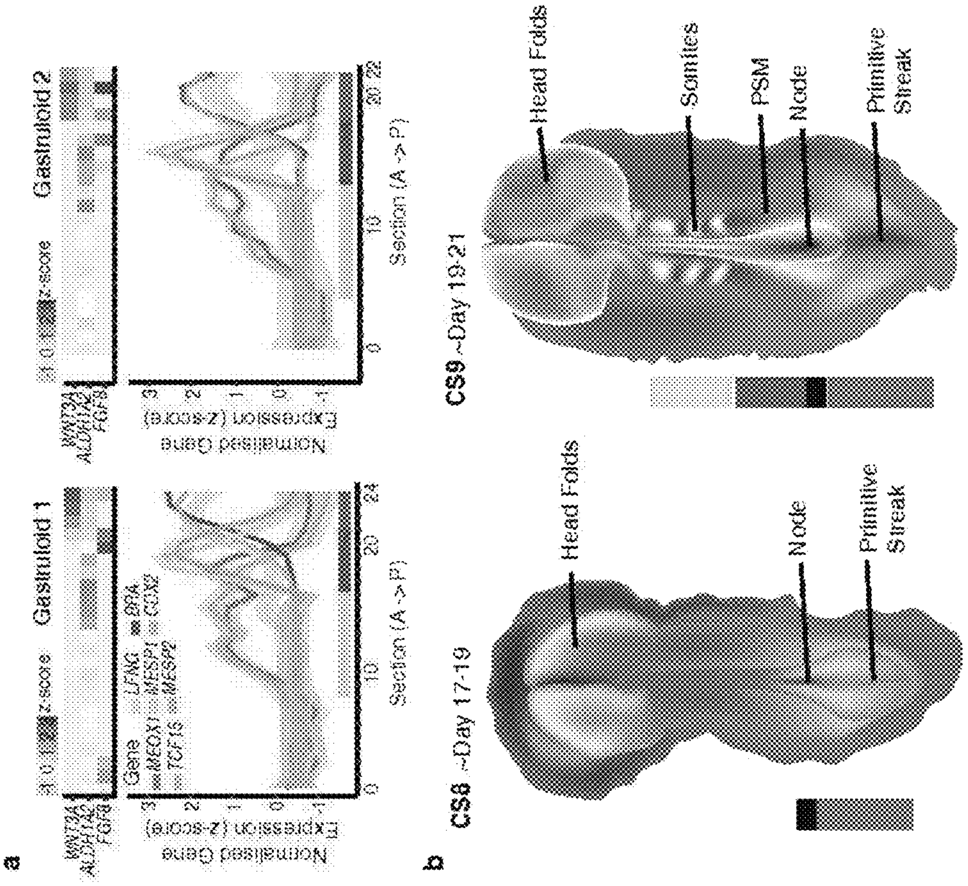
FIG. 12: Comparison to the mammalian embryo. a, Patterned organization of somitogenesis-related genes, including signaling gradients (upper) and downstream genes related to the tailbud and developing somitic tissue (lower) for two human gastruloids. b, Illustration of Carnegie Stage (CS) 8 and 9, showing gross anatomical features, including somite boundaries. Adapted from Ref32. In both panels, yellow bars correspond to somite-related features, magenta bars to developing somite-related and presomitic mesoderm features, and green bars to primitive streak and tailbud mesoderm-related features. Black bars relate to node-like features. c, Heatmap showing the AP expression pattern of 253 genes in mouse and human gastruloids (left, average human gastruloid with n=2; right, average mouse gastruloid, n=5), 20 μm tomo-seq data. Only genes that have orthologs between mouse and human, that significantly correlate between individual mouse gastruloid samples and that also significantly correlate between human gastruloids replicates were included in the analysis ($P<0.05$). Genes are clustered based on their AP expression pattern; numbered bars represent clusters. Red stars indicate clusters that deviate in their expression position between the two systems.
Figure 12:
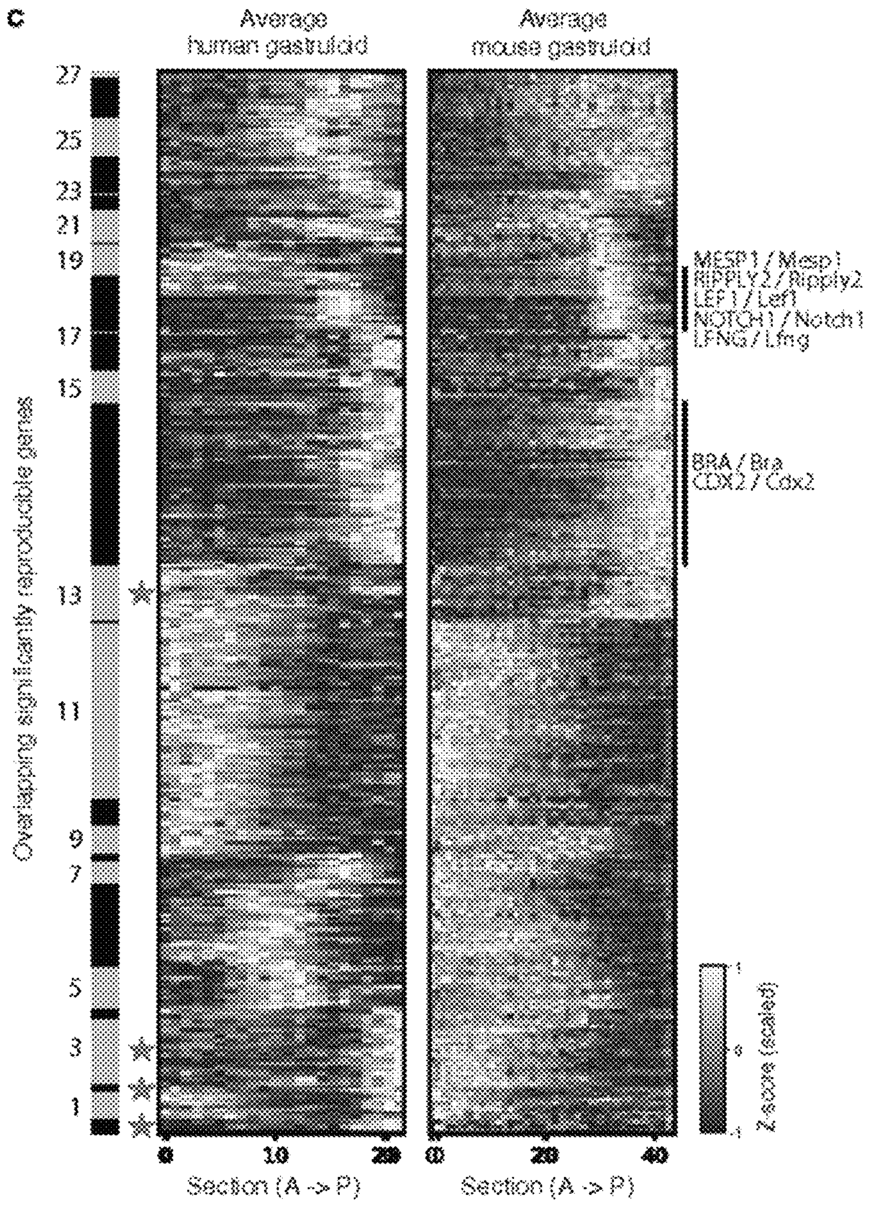

The tomo-seq data also revealed a small representation of neural gene expression, but a very clear signal of patterned mesodermal differentiation: a posterior-to-anterior signature for somitogenesis with expression of tailbud genes (BRA and CDX2) peaking most posteriorly, overlapping with LFNG which also peaked posteriorly, a short domain of MESP1 and MESP2, followed by a more anterior, broader domain of MEOX1 and TCF15 expression. This sequence of gene expression was overlaid by gradients of WNT3A posteriorly, followed by FGF8 and then RALDH2 (ALDH1A2) more anteriorly (FIG. 12*a*). This overall pattern of gene expression mirrors the organisation of paraxial mesoderm specification and differentiation in a mammalian embryo, as well as temporal sequences of somitogenesis in directed differentiation of hESCs and, together with the expression of the HOX genes, is suggestive of an active, axially polarized somitogenesis transcriptional program in human gastruloids. The results presented here suggest that human gastruloids display elements of a mammalian embryonic AP axis, including polarisation and organised arrangement of gene expression such as those involved in early somitogenesis.

The axial organization of the somitogenesis program of gene expression suggests a possibility of approximately staging gastruloids developmentally. Examination of images of extant collections of human embryos reveals a major transition in morphogenetic events between Carnegie Stages (CS) 8 and 9 (which correspond to days 17-19 and days 19-21 respectively), associated with the onset of somitogenesis (FIG. 12*b*). Images of CS9 embryos reveal the presence of 1 to 3 somite pairs that are absent in CS8, with a short domain between the last somite and a node like structure. In the gastruloids, the patterns of gene expression suggest the presence of a somitic domain anterior to a presomitic domain of a similar length, leads us to suggests that 72 h human gastruloids might serve as a model for some of the features of late CS8 or early CS9 of human development.

Materials & Methods for Examples 1-3

Cell Lines

We used a wild type hESC line (mSHEF7; REF) as well as two transgenic lines, the H9TV BRACHYURY-Venus reporter (Mendjan et al., 2014) and RUES2-GLR, the triple reporter for germ layer markers with BRACHYURY-H2B-mCerulean, SOX17-H2B-tdTomato and SOX2-mCitrine (Simunovic et al., 2018). We also used a human induced pluripotent stem cell line, known as HYS01030 (unpublished).

Cell Culture Conditions

Human ESCs were cultured in NutriStem hPSC XF medium (Biological Industries) on Vitronectin coated flat bottom 6-well plates (Costar, Corning Inc.). For coating of plates, 1 ml Dulbecco's Phosphate Buffered Saline without $MgCl_2$ and $CaCl_2$ (PBS−/−, Sigma-Aldrich) supplemented with Vitronectin (1:100) was used per well. Plates were then incubated for 1.5-4 h at room temperature or 1-7 days at 4° C. Immediately before use, plates were washed with PBS−/−. hESCs were passaged at 70-90% confluency (about every 3-5 days). After washing twice with 3 ml PBS−/− per well, 2 ml 0.5 mM EDTA (0.5M stock at pH 8.0, Invitrogen, Life technologies) in PBS−/− was applied per well and cells were incubated for 5 min at 37° C., 5% CO2 for detachment. Clumps of cells were then collected in a centrifuge tube and PBS −/− was added to dilute the EDTA, before centrifugation for 3 min at 1000 rpm. The supernatant was then discarded, and cells were gently resuspended in 1 ml Nutristem. Cells were split at a ratio of 1:5-1:10. Medium was exchanged daily.

Pre-Treatment Before Generating Human Gastruloids

Before aggregation, hESCs cultured in 6-well plates were typically pretreated with 3-3.5 μM CHIR99021 (Chiron) in Nutristem for 24 h, unless otherwise stated. The exact concentration of the Chiron pretreatment was observed to be cell-line specific, and each new cell line should be titrated for optimal gastruloid formation with between 1.5-5 μM Chiron.

For signal modulation experiments, RUES2-GLR cells were pre-treated for 1 day in Nutristem supplemented with 100 ng/ml recombinant human Wnt3a (5036-WN-010) or 50 ng/ml BMP4 (314-BP), and aggregated in E6 and ROCK inhibitor with additional supplementation as shown. Subsequent media changes were performed daily with E6 alone. To test the effect of signal modulation on gastruloid formation, RUES2-GLR cells were pre-treated in Nutristem supplemented with 3.25 μM Chiron and one of 1 μM LDN193189 (04-0074), 1 μM XAV-939 (04-0046), or 10 μM SB431542 (1614) before aggregation in E6 with 0.5 μM Chiron and ROCK inhibitor, unless otherwise stated. Subsequent media changes were performed daily with E6 alone.

An alternative, 'dorsalised' protocol used 3 μM Chiron, supplemented with 10 μM SB431542 Nodal inhibitor (SB431542) also in Nutristem for 24 h.

Generation of hESC Gastruloids

After pre-treatment, hESCs at 60-85% confluency were washed twice with PBS−/−. For detachment, 2 ml 0.5 mM EDTA in PBS−/− was applied per well and cells were incubated at 37° C., 5% CO2 for 6.5 min. The plate was then carefully tapped against a solid object to promote detachment and the suspension was pipetted up and down repeatedly (5-10−) with a P1000 to break remaining clumps into single cells.

The suspension was then transferred into a 15 ml centrifuge tube with 8 ml PBS−/− and centrifuged for 3-5 min at 1000 rpm. The supernatant was removed, cells were washed with PBS−/− and spun down again 3-5 min at 1000 rpm. Subsequently, depending on the pellet size, cells were resuspended in 500 μl to 2 ml Essential 6 (E6) medium (Gibco, life technologies) and counted using an automated cell counter (MoxiZ, Orflo). Optimal cell density should be around 1×10^6/ml. The specific number of cells optimized per cell line (400/well for RUES2-TR, 500/well for mSHEF7 and H9TV lines) were then added to E6 supplemented with 5 μM Rock Inhibitor and 3 μM Chiron. Using a multichannel pipette, cells in this suspension were plated in 40 μl per well of an ultra-low adhesion, round bottom 96-well plate (Costar, Corning Inc.). At 24 h after aggregation, 150 μl E6 were added into each well using a multichannel pipette. E6 (see Chen et al., 2011) was continuously exchanged every subsequent day by removing 150 μl per well and adding the same amount.

Immuofluorescent Imaging

For fixation, aggregates were extracted from 96-well plates using a P1000 pipette and pooled into a 30 mm Drosophila glass dissection well. After 3 washes with PBS−/−, 1 ml 4% paraformaldehyde (PFA) in PBS−/− was applied and samples were incubated for 2 h at 4° C. with gentle horizontal rotation. Gastruloids were then washed 3× with PBS−/− and transferred into small nets which were then placed in individual wells of a 24-well plate. Aggregates were washed 3× for 10 min with PBS−/− containing 10% foetal bovine serum (FBS) and 0.2% Triton X-100 (PBSFT) with gentle horizontal rotation. For blocking, samples were incubated for 1 h at 4° C. in PBSFT on an orbital shaker. Primary antibodies included: rabbit anti-Cdx2 (ThermoScientific, EPR2764Y), rabbit anti-Brachyury (abcam, EPR18113), goat anti-Sox2 (R&D Systems, AF2018) mouse anti-NCadherin (BD Biosciences, BD610920), chicken anti-GFP (invitrogen, ThermoScientific) and were diluted in PBSFT and applied overnight at 4° C. with gentle horizontal rotation.

The following day, aggregates were washed 9× at with PBSFT: 2× for 5 min, 3× for 15 min and 4× for 1 h. Samples were kept at 4° C. on an orbital shaker. Secondary antibodies and nuclear Hoechst (Hoechst 33342, invitrogen) were applied in PBSFT overnight. After 9 washing steps with PBSFT as described above, aggregates were washed 5× at room temperature with PBS−/− containing 0.2% foetal bovine serum (FBS) and 0.2% Triton X-100 (PBT): 2× for 5 min and 3× for 15 min. Subsequently, samples were incubated in the dark for 30 min with a 1:1 glycerol/PBT solution, followed by a 30 min incubation with a 7:3 glycerol/PBT solution which was then replaced with mounting medium (90% glycerol, 0.1M Tris-CI pH 8.0, 0.05 g n-propyl gallate). Individual aggregates were taken up in 3 μl droplets and mounted on glass slides with spacers.

Immunostaining

Human gastruloids were fixed and immunostained according to the existing methods for gastruloid staining' unless otherwise stated. The antibodies used were: 1:200 Rabbit anti-CDX2 (ThermoScientific, EPR2764Y); 1:200 Goat anti-GATA6 (R&D Systems, AF1700); 1:200 Rabbit anti-BRACHYURY (AbCam, ab209665); 1:200 Goat anti-SOX2 (R&D Systems, AF2018); 1:200 Mouse anti-CDH2 (BD Biosciences, BD10920); 1:200 Rat anti-CDH1 (Takara, M108), 1:100 Rabbit anti-Wnt3a (ab219412), 1:200 Rabbit anti-LEF1 (ab137872), 1:200 Rabbit anti-FOXA2 (ab108422), 1:200 mouse anti-NOTCH1 (552466). All secondary antibodies were all diluted 1:500, and included Alexa-Fluor-488, -568 and -647 conjugated antibodies (Invitrogen).

Adherent cell staining was done using 1:200 Mouse anti-CDH2 (BD Biosciences, BD10920), 1:200 Rat anti-CDH1 (Takara, M108) and 1:200 Rabbit anti-BRACHYURY (AbCam, ab209665) primary antibodies. Quantification was performed using Fiji software on the whole image (histograms) or using a line ROI through the colony (line graph).

In Situ Hybridisation

Human gastruloids were collected at 72 h or 96 h post aggregation. After rinsing them briefly in PBS, they were fixed in 4% PFA either overnight or 2 h at 4° C. and stored in 100% methanol at −20° C. until further used. In situ hybridization was performed on whole mount gastruloids as described [10] with minor modifications. Gastruloids were rehydrated by incubating them for 3-5 min in series of decreasing concentration of methanol (75%, 50%, 25% and 0% respectively) in TBST (20 mM Tris 137 mM NaCl, 2.7 mM KCl, 0.1% Tween, pH=7.4). After washing gastruloids in TBST, they were incubated in proteinase K (2.5 μg/ml) for 2 mins to make them permeable to probes and post-fixed in 4% PFA for 20 min at room temperature, before washing again in TBST. To block non-specific interactions, they were prehybridized at 68° C. for 4-5 h. Hybridization was performed by incubating them in 200 ng/ml of specific digoxigenin (DIG)-labelled RNA probes at 68° C. overnight. The probe sequences used can be found in Supplementary Table 2. The following day, after washing the gastruloids at 68° C., they were incubated in blocking solution for 1.5 h at solution at room temperature. Gastruloids were then incubated overnight in anti-DIG antibody coupled to alkaline phosphatase (Sigma) at 1:3,000 dilution in blocking buffer at 4° C. The next day, they were washed in MABT (100 mM maleic acid, 150 mM NaCl, 0.1% Tween, pH 7.5) overnight at 4° C. Gastruloids were then washed 3 times with TBST and 3 times in alkaline phosphatase buffer (0.1 M Tris pH 9.5, 100 mM NaCl, 0.1% Tween) and incubated in BM purple solution (Sigma) either at 4° C. or RT until the signal was fully developed. Gastruloids were washed in TBST and post fixed in 4% PFA for 20 min at RT. For imaging gastruloids were suspended in CUBIC-R1A tissue clearing reagent.

RT-qPCR

Gene expression was analysed from adherent cells using Trizol (Ambion LifeTechnologies) according to manufacturer's instructions. Total RNA was quantified using a NanoDrop 2000C (ThermoScientific) and 5 μg was added to a reverse transcription reaction with Superscript III (Invitrogen) according to manufacturer's instructions. Resultant cDNA was quantified by qPCR with SYBRGreen (Merck) using a liquid handling robot (Qiagility, Qiagen) and analysed on a RotorGeneQ thermocycler (Qiagen). Primer sequences can be found in Supplementary Table 1. Concentration of cDNA was estimated using an in-house MAK2 analysis method.

Widefield Imaging

Confocal imaging was performed using a LSM700 (Zeiss) on a Zeiss Axiovert 200 M using a 40 EC Plan-NeoFluar 1.3 NA DIC oil-immersion objective. Image capture was performed using Zen2010 v6 (Carl Zeiss Microscopy Ltd, Cambridge UK). All samples were fixed and immunostained prior to imaging, except for the SMAD1-RFP; H2B-mCitrine gastruloids which were imaged live. For gastruloids made from the RUES2-GLR reporter line, we never observed fluorescent signal of reporter proteins following our fixation protocol, and therefore used the same antibody design and microscope settings as described.

Wide-field imaging was performed using a 37° C. incubated chamber supplied with 5% $CO_2$, attached to a Zeiss AxioObserver.Z1 (Carl Zeiss, UK) as described in Turner et al., 2017. All images were analysed using Fiji software (Schindelin et al., 2012), and any adjustments are always consistent within a panel. Presented images have been rotated to align their AP axis horizontally where necessary, as indicated by a dark grey background.

Scanning Electron Microscopy

Human gastruloids, made from the RUES2-GLR line at 72 h after aggregation, were washed twice with HEPES buffer and fixed overnight in 3% Glutaraldehyde, 0.05 M sodium cacodylate buffer pH 7.4 at 4° C. Samples were washed several times in de-ionised water (DIW) at room temperature (RT) to remove fixative. Melinex coverslips at 12 mm diameter were covered with a large drop of poly-L-lysine solution (Sigma P4707) and incubated for 15 minutes at RT. Excess solution was drained off and the coverslips were allowed to air-dry at 37° C. The gastruloids were transferred to the poly-L-lysine coated coverslips in a drop of DIW and allowed to adhere for about 30 min at RT whilst ensuring that the gastruloids remained covered with DIW. Excess DIW was carefully drained off using a tissue paper and the samples were immediately plunge-frozen in liquid nitrogen-cooled ethane. After freeze-drying overnight in a liquid nitrogen-cooled turbo freeze drier (Quorum Emitech K775X), samples were mounted on aluminium SEM stubs using sticky carbon pads and sputter coated with 35 nm Au followed by 15 nm iridium. Samples were viewed in a FEI Verios 460 scanning electron microscope using an Everhart-Thornley detector in secondary electron mode at 2 keV accelerating voltage and 25 pA probe current.

Image Analysis

Human gastruloids made using the RUES2-GLR reporter line were specifically analysed for dynamic reporter expression. An in-house MATLAB script was developed to assess the dynamic fluorescent marker expression along the AP axis of human gastruloids. Widefield images of gastruloids were taken at 24 h, 48 h and 72 h and aligned along their anteroposterior axis with reference to fluorescent reporter expression. For each sample, a binary image was generated in the brightfield channel and used as a mask for all fluorescent channels and the major (length) axis was identified. Consequently, for every pixel along the length axis, the sum of intensity values of the respective channel along the width of the aggregate was divided by the width of the gastruloid at that specific point, yielding the normalized fluorescence intensity along the length of the sample. This process was then repeated for every acquired fluorescent channel. Gastruloids used for this analysis were a full set from one experimental batch, and images were only excluded from the analysis when anteroposterior alignment or binarization were unsuccessful.

In order to quantify the degree of elongation of human gastruloids, brightfield channel widefield images were imported into Fiji (Schindelin et al., 2012). The length of the longest axis was measured using the line tool, followed by the length of the perpendicular axis at the mid-point of the longest axis line. The ratio of these two values was calculated and plotted by time-point and condition, using R. Significance was assessed using the Welch's Two-Sample t-test.

The estimate of the proportions of gastruloid shapes (spherical, ovoid, elongated-short and elongated-long) was estimated for multiple independent biological replicates.

This was performed using an in-house method derived from that previously described (Turner 2017, doi: 10.1242/dev.150391). Briefly, images were converted into single-channel, 8-bit TIFF files using FIJI (Schindelin et al., 2012). These were then processed using Python 3.6 (Python Software Foundation, www.python.org/) and the Open-CV package (Bradski 2000) to apply a Gaussian blur before performing Otsu's thresholding and floodfilling with erosion to assign a mask around the shape of each gastruloid. Various quantitative features were then extracted from these contours, which were further processed using R. The categories of each shape descriptor were defined as follows: Spherical, Circularity less than or equal to 1.1 or Aspect Ratio (AR) greater than or equal to 0.95; Ovoid, Circularity less than or equal to 1.2 or AR greater than or equal to 0.9; Elongated—Short, Circularity greater than 1.2 and less than or equal to 1.4 and AR less than 0.9; Elongated—Long, Circularity less than 1.4 and AR greater than 0.9. Images were quality controlled for empty wells or those with debris that compromised shape descriptors, using quantification of area or circularity outliers and confirmed manually by examination of images.

Tomo-sequencing and Mapping

Tomo-sequencing was performed and analysed in an updated version of published methods (Junker et al., 2014; and Kruse et al., 2016). In short, gastruloids were sectioned along their AP axis, and the mRNA-content of each section was extracted using SORT-seq (Muraro et al., 2016). Paired end (75 bp) sequencing was performed on the resulting RNA-seq libraries using the Illumina Next-Seq sequencing platform. Read 1 contains the cell or section barcode and the unique molecular identifier (UMI). Read 2 contains the biological information. Reads 2 with a valid cell/section barcode were selected and mapped using STAR-2.5.3a with default parameters to the human GRCh38 genome (ENSEMBL version 93), and only reads mapping to gene bodies (exons or introns) were used for downstream analysis. Reads mapping simultaneously to an exon and to an intron were assigned to the exon. Mappabilities for the different samples range between 44% and 47%. For each cell or section, the number of transcripts was obtained as previously described (Bradski 2000). We refer to transcripts as unique molecules based on UMI correction.

After mapping, spike-ins, ribosomal, and mitochondrial genes were removed from downstream analysis, together with KCNQ1OT1, LARS2, and MALAT1, because these genes seem to be linked to mapping errors and have been shown to be erroneous in earlier studies. In each gastruloid, data was then normalized to the median number of unique transcripts per slice, and the z-score of each gene was extracted along sections.

Gene Expression Data Analysis

The reproducibility of AP expression pattern between different gastruloid replicates was scored for each gene using a random background model to calculate the Pearson correlation coefficient p-value. The p-value threshold to select reproducible genes was set at 0.001. These significantly reproducible genes were then clustered using a Self-Organising Map (SOM) method, followed by Hierarchical Clustering to determine general patterns of gene expression along the AP axis.

Average gastruloid profiles were generated using the mean of z-scores along the AP axis. When the number of sections between replicates was different, values were quadratically interpolated to fill spaces using the interp1d function from the package scipy.interpolate (Python 3.6).

Differential gene expression was performed by normalizing the transcripts in each section to 100,000 for all gastruloids; then pooling all sections of each gastruloid together; and finally assessing significant differentially expressed genes based on total expression using the Binomial test.

For smoothened line-graphs of gene expression, the distribution of gene expression along the sections was plotted using R, and smoothened using the geom_smooth( ) function (method=loess, span=0.3, level=0.5) to minimise background variability. For each gene expression distribution, the confidence interval is therefore shown (at 0.5 Confidence Interval) as a grey ribbon.

Gene Ontology (GO) term analysis for each hierarchical cluster of the Chiron pre-treated human gastruloids was performed using ENSEMBL IDs run with the DAVID Annotation tool [46] with the human genome as a background model, focussing on Biological Process terms. Statistical correction for multiple comparisons was achieved using Benjamini adjustment.

Gene Ontology for each hierarchical cluster of the human-to-mouse gastruloid comparison was performed using the python package goatools (Klopfenstein et al., 2018), setting the p-value at 0.05. Both the list of reproducible genes in each corresponding condition, or the full human transcriptome was set as a background model, focussing on Biological Process terms. Statistical correction for multiple comparisons was achieved using Bonferroni adjustment.

Example 4—Culture of Human Embryonic Stem Cells and Human Induced Pluripotent Stem Cells Using Methods of the Invention, Including Pretreatment With Signal Modulators

Materials & Methods—see Materials & Methods for Examples 1-3, Varied as Described Below.

An alternative, 'dorsalised' protocol used 3.25 μM Chiron, supplemented with 10 μM SB431542 Nodal inhibitor (SB431542) also in Nutristem for 24 h. They were then aggregated in E6 with 3 μM Chiron and ROCK inhibitor.

Results

Figure 18:
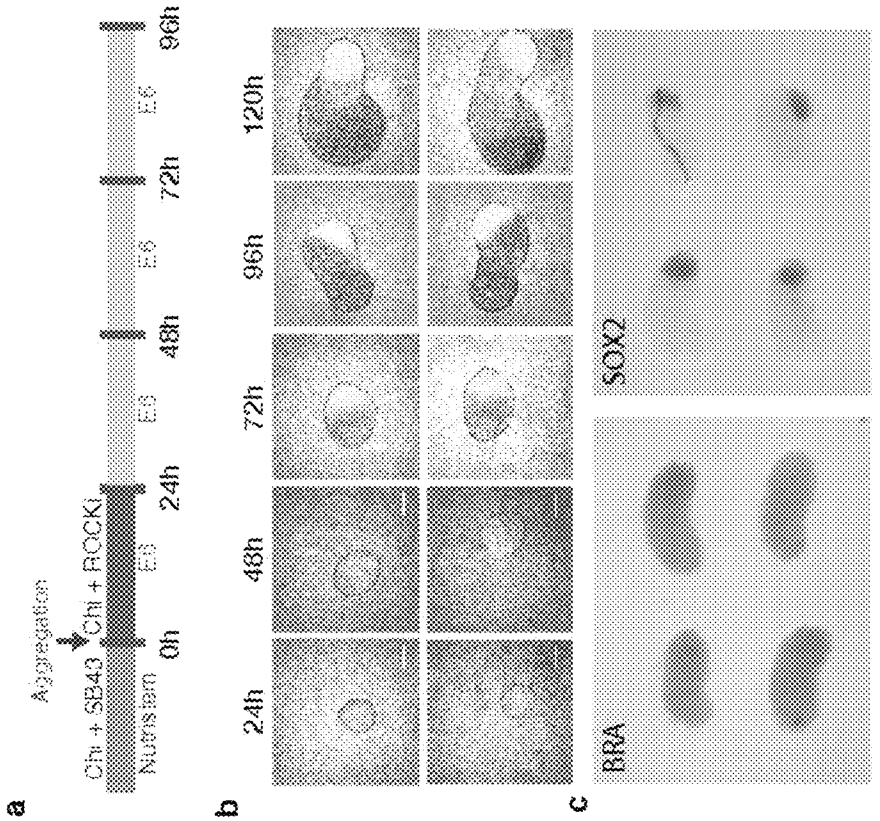
FIG. 18: Perturbation of Nodal signaling in human gastruloids. a, Schematic representation of the protocol used to generate Chiron (Chi) and SB431542 (SB43) pretreated human gastruloids (Chi+SB43). b, Representative examples of the dynamic development of Chi and SB43 (Chi+SB43) pre-treated gastruloids, made from the RUES2-GLR cell line. These show an ovoid morphology and polarization of gene expression at 48-72 hours after aggregation (h), and elongation at 96-120 h. Colours indicate reporter fluorescence as indicated in FIG. 2*a*. No SOX17-tdTomato reporter expression was observed. Scale bar, 100 μm. c, In situ hybridisation against BRA and SOX2 mRNA in 96 h Chi+SB43 gastruloids. Four representative examples are shown for each gene. d, Widefield imaging of the two 120 h RUES2-GLR derived Chi+SB43 pretreated human gastruloids used for tomo-sequencing. Scale bars; 100 μm. mCer, mCerulean; tdTom, tdTomato; mCit, mCitrine. e, Venn diagram of the number of reproducibly-localised genes in the Chiron pre-treated human gastruloids (Chi hGld; green) and in the Chiron and SB43 pre-treated human gastruloids (Chi+SB43 hGld; yellow). Numbers indicate counts of genes, while percentage values in brackets indicate proportion relative to the full figure. f, Differentially expressed genes from those that were reproducible in either, or both, Chi or Chi+SB43 pre-treated gastruloids. g, Transcriptomic comparison of the gene expressional localization between an averaged Chi pre-treated and averaged Chi+SB43 pre-treated gastruloid across their anterior (A) to posterior (P) axis. The genes displayed are those that were significantly reproducible in one or other of the conditions. Greyscale bands show the hierarchical clustering of gene expression behavior for the four gastruloids, and coloured bands indicate whether a particular gene is reproducible in one, or both the conditions (Red, Chi+SB43 only; Blue, Chi only; Grey; both). Dark red box indicates cluster for which expression is lost following SB43 pre-treatment (Cluster 4). White rows indicate lack of expression detected for that gene.
Figure 18:
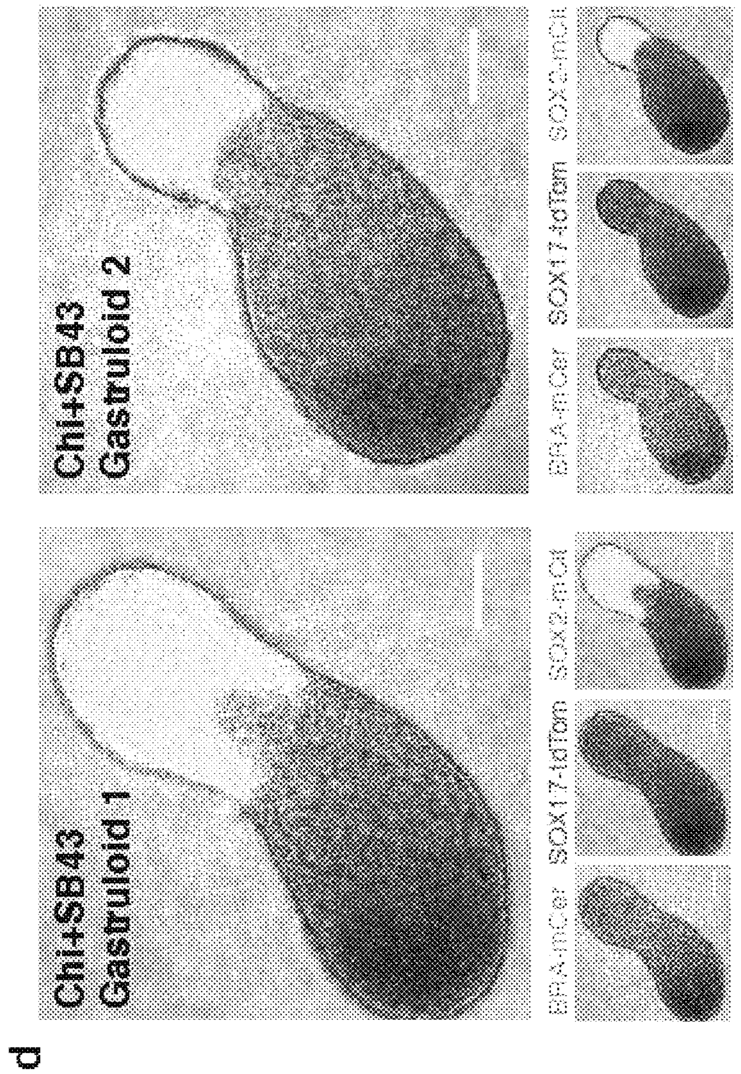
Figure 18:
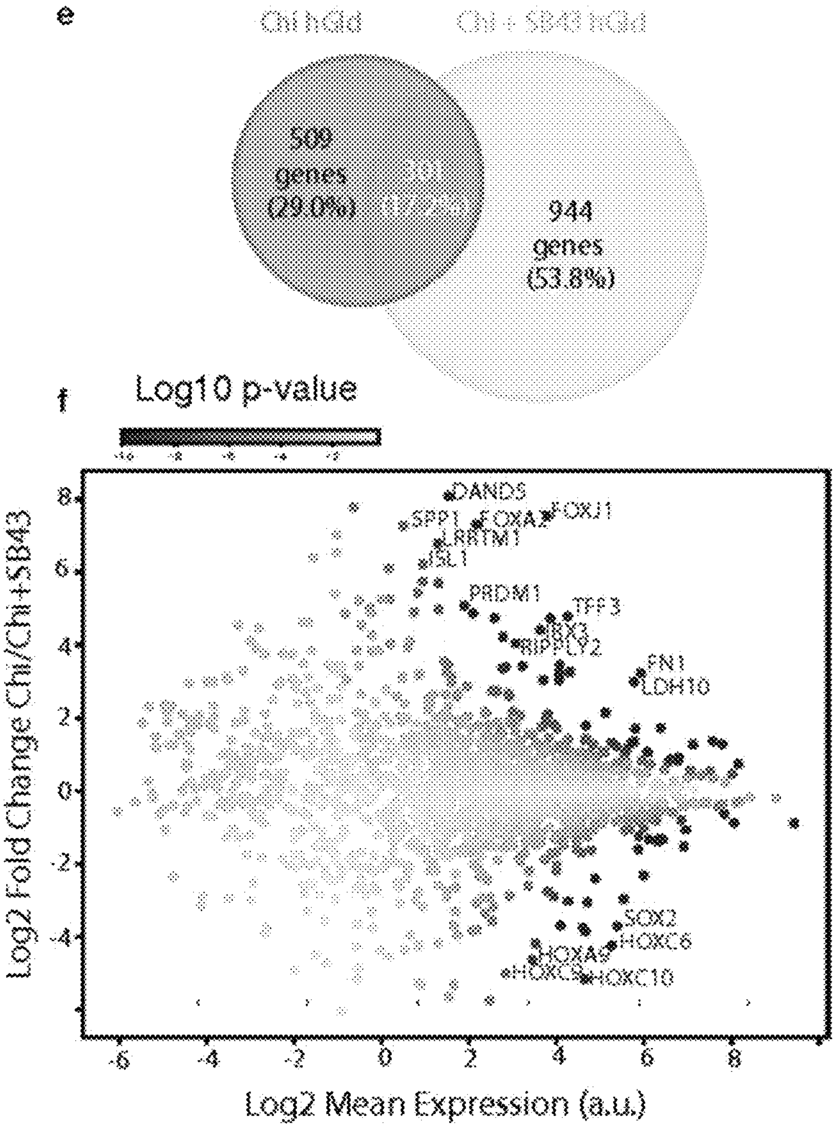
Figure 18:
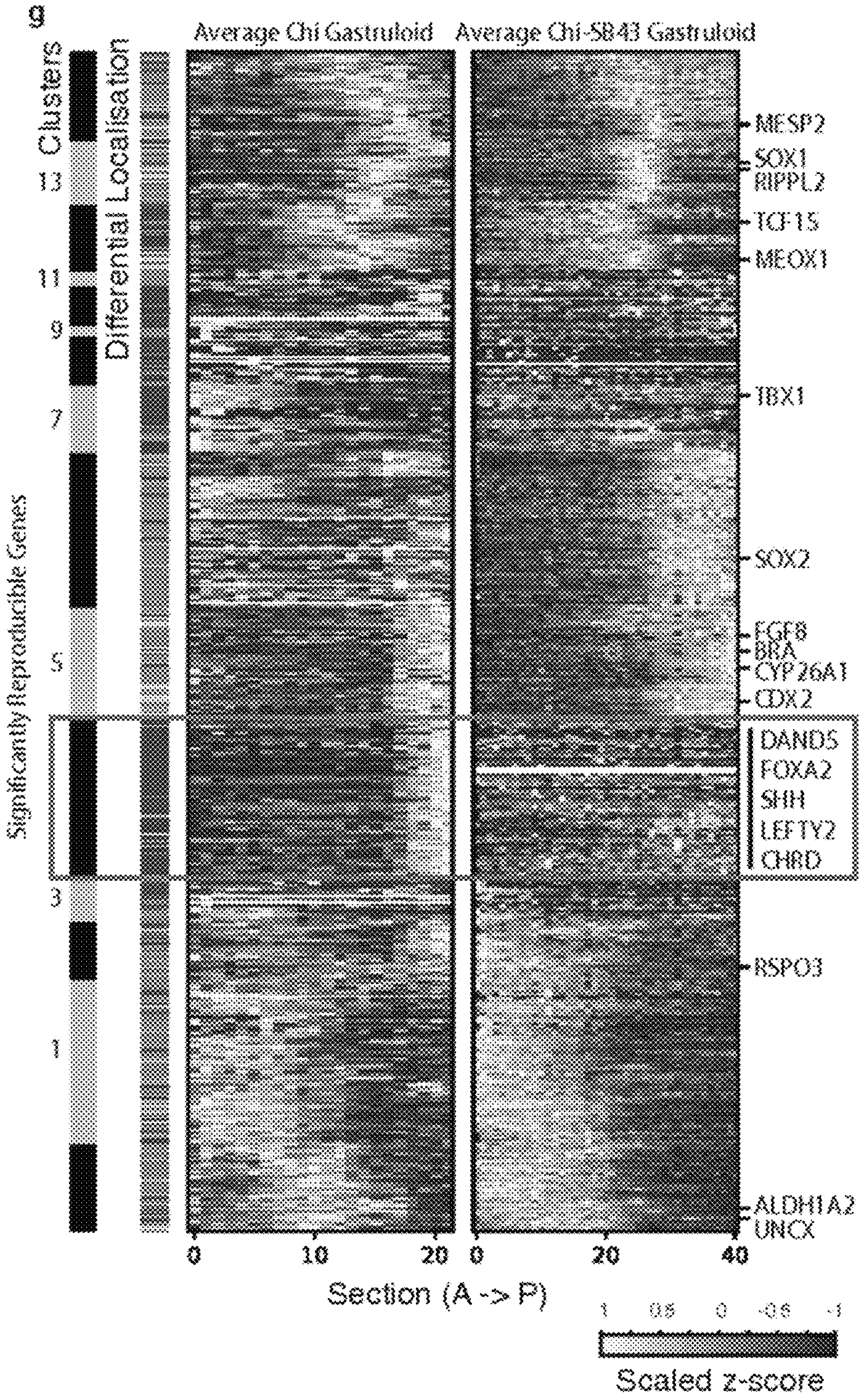

Chiron and SB-431542 (herein SB43) pre-treated cells, aggregated to make gastruloids, were able to elongate and polarise their gene expression in a manner similar to the original method (FIG. 18*a-b*). However, they also displayed a larger, well-defined SOX2 domain at their posterior end, diffuse expression of BRA that approximated a gradient from anterior to posterior, and an absence of detectable SOX17 expression (FIG. 18*b-d*). We analysed two 120 h SB43 treated gastruloids using tomo-sequencing and compared their transcriptional profile to those without Nodal-signalling inhibition during pre-treatment (FIG. 18*d, g* and FIG. 19*a-c*). Although 301 genes were reproducibly localised in both conditions, SB43 treatment led to the acquisition of 944 genes with novel spatial localisation, and the loss of reproducible localisation of 509 genes (FIG. 18*e*). One cluster of genes lost on SB43 pre-treatment (Cluster 4; FIG. 18*g*), was originally observed in the posterior-most region of the Chiron pre-treated gastruloids, and included genes known to be involved in Nodal signalling, such as DAND5, DACT2 and SHH as well as those typically expressed in or around the node in mammalian embryos including FOXA2, CHRD, PTCH2, LEFTY2 and MIXL1, consistent with a loss of Nodal activity.

Figure 19:
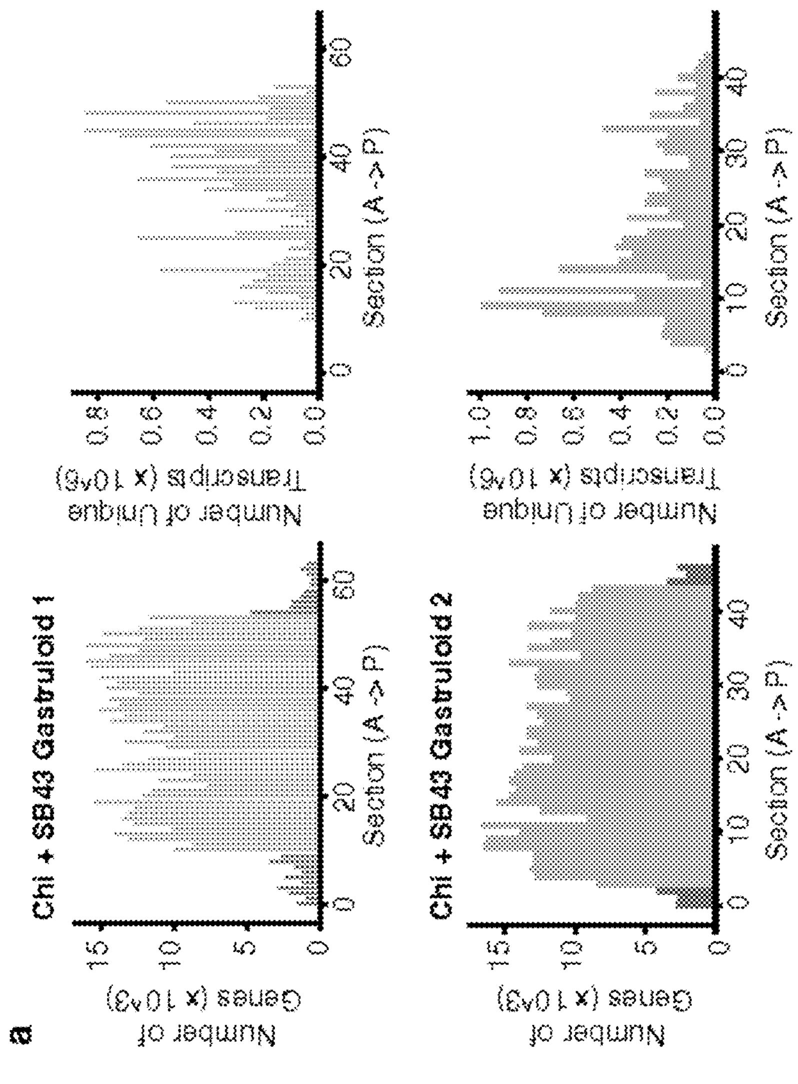
FIG. 19: Transcriptional profiles of gastruloids exposed to Nodal inhibition before aggregation. a, Quantification of number of genes (left) and number of unique transcripts (right) detectable in each section along the anterior-posterior (AP) axis of Chiron+SB43 pre-treated human gastruloids made from 120 h RUES2-GLR gastruloids. Sections above the threshold and used for downstream gastruloid tomo-seq analysis are marked in blue, while sections below the threshold are coloured dark grey. Two replicates are shown. b, Significantly reproducible gene expression patterns of individual replicates of Chiron+SB43 pre-treated human gastruloids (left), and resultant average gastruloid (right) along the AP axis.. c, Hierarchical clustering of reproducible tomo-seq gene expression patterns along the length of the AP axis (which has been normalised between 0 at the most anterior and 1 at the most posterior). Ribbon indicates standard deviation for the set of genes within each cluster. d, Expression detected for markers of all three germ layers. White rows indicate lack of expression detected for that gene. e, Gene expression traces along the AP axis of the four human gastruloids (gray lines, Chiron pre-treatment; blue lines, Chi+SB43 pre-treatment; solid lines, Replicate 1; dashed lines, Replicate 2). Traces show sustained posterior expression of tailbud-related genes (BRA, SOX2, CDX2), absent expression of Nodal signaling-related genes (NODAL, FOXA2, SHH and DAND5) and aberrant expression of various other genes (CLDN11, CHRD, TFF3, FN1).
Figure 19:
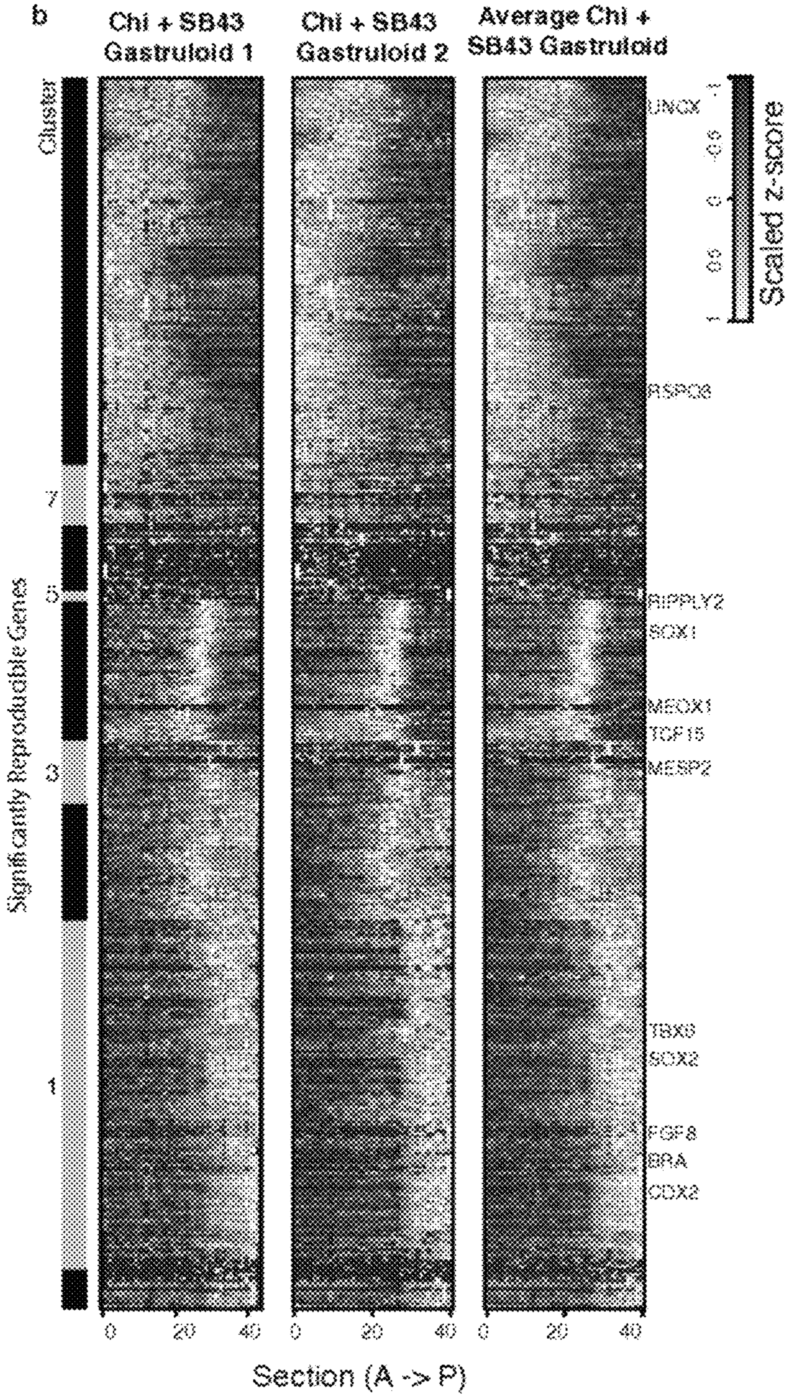
Figure 19:
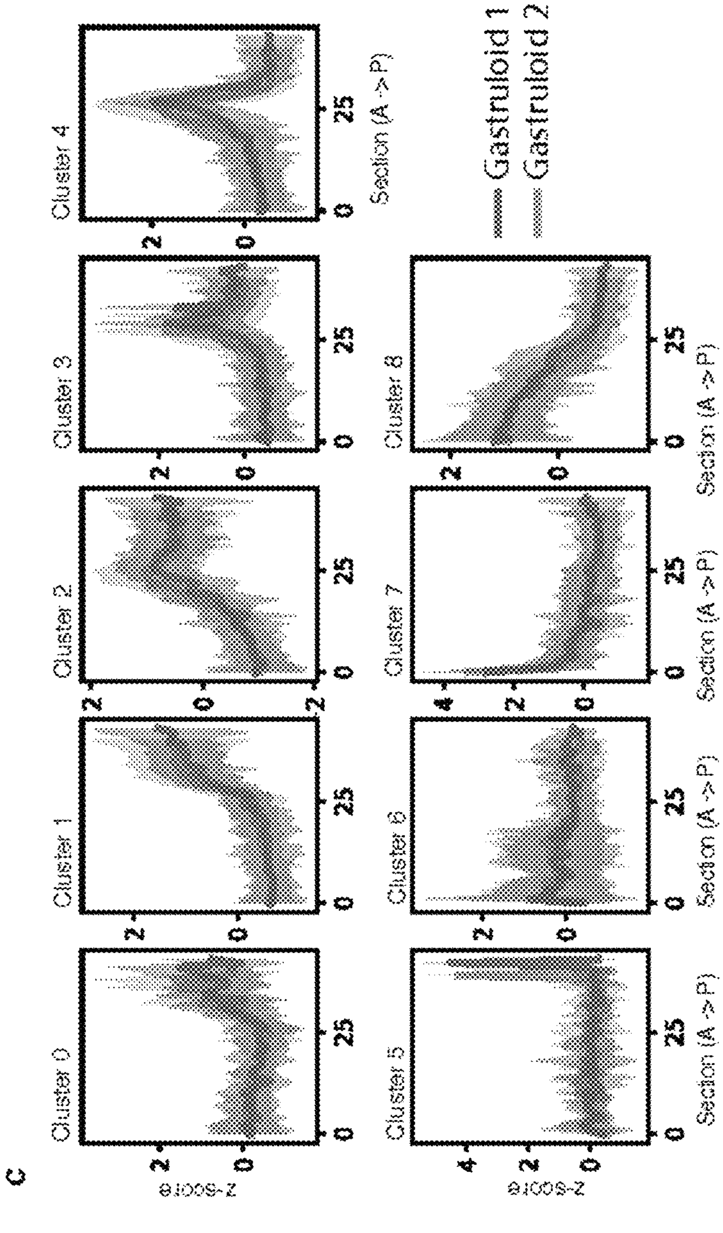
Figure 19:
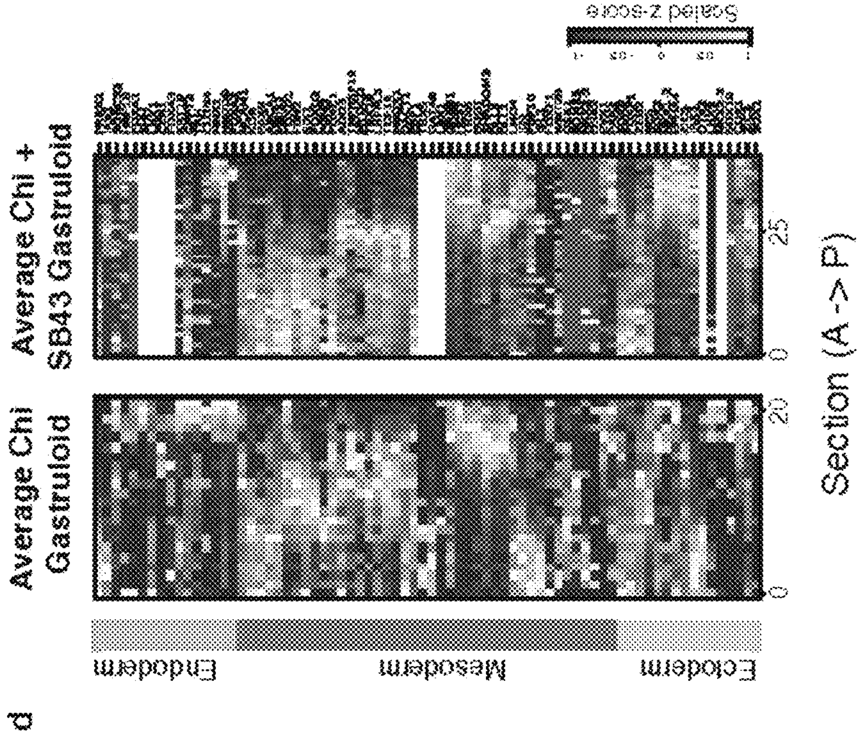
Figure 19:
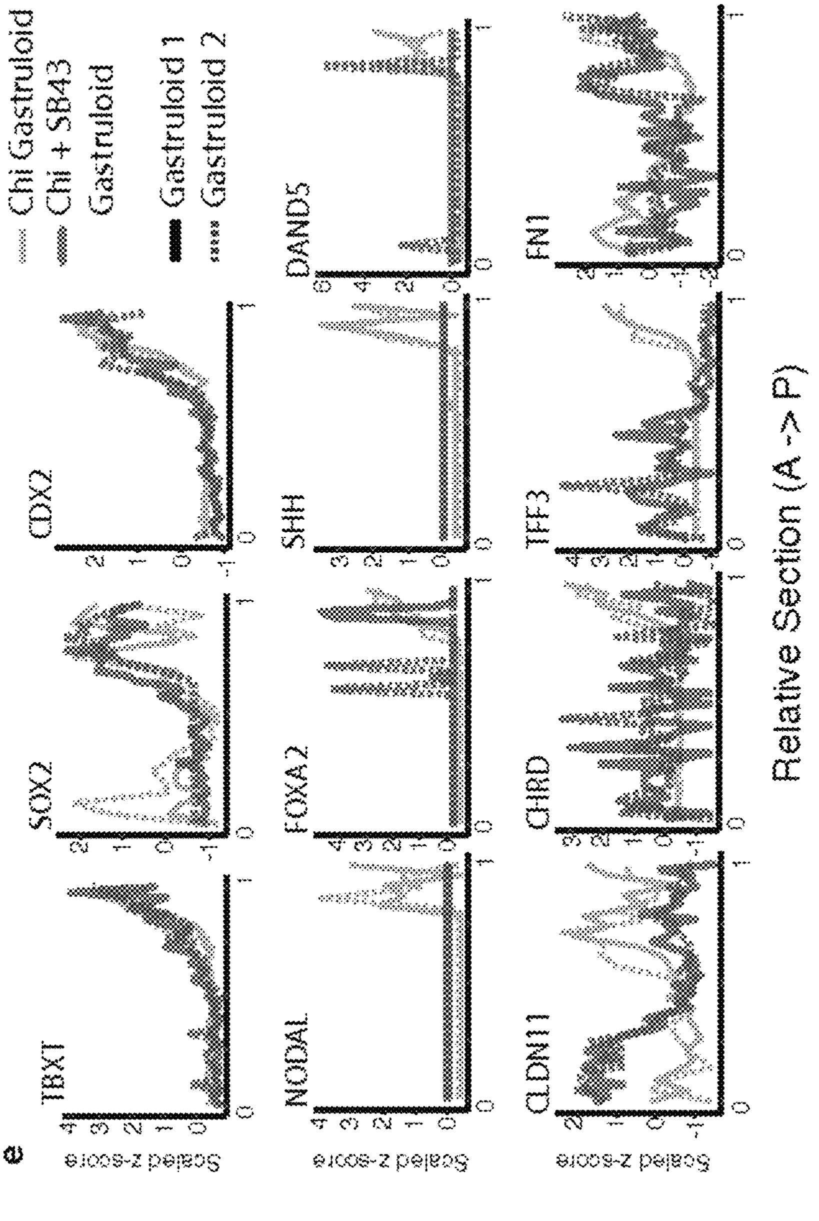

Of the genes that were reproducible in either or both conditions, 564 genes (33%) were differentially expressed between the two treatments (FIG. 18*f*), including down-regulation of many of the Nodal signalling components and targets. Conversely, we observed the up-regulation of some HOX genes (HOXC9, HOXA9, HOXC6) and of SOX2 (FIG. 18*f*). When we specifically examined germ layer markers we noticed a decrease in expression of genes associated with definitive endoderm (SHH, LHX1, CER1, FOXA3, SORCS2, FOXA2) consistent with a role of Nodal in the specification of this germ layer, and a loss of many genes associated with cardiac development (TBX5, GATA6, LBX1, NKX2.5) which is likely to be a consequence of the loss of induction from the endoderm (FIG. 19*d-e*).

REFERENCES

Allison, T. F., et al., *Identification and Single-Cell Functional Characterization of an Endodermally Biased Pluripotent Substate in Human Embryonic Stem Cells.* Stem Cell Reports, 2018. 10(6): p. 1895-1907.

Baillie-Johnson, P., et al., *Generation of aggregates of mouse ES cells that show symmetry breaking, polarisation and emergent collective behaviour.* JOVE, 2015. doi: 10.3791/53252(105).

Bradski, G. The OpenCV library. *Journal of Software Tools* Dr. Dobb#39; s (2000).

Chen et al., 2011. Chemically defined conditions for human iPS cell derivation and culture Nat Methods 8(5): 424-429.

Junker, J. P., et al., Genome-wide RNA Tomography in the zebrafish embryo. Cell, 2014. 159(3): p. 662-75.

Klopfenstein, D. V. et al. GOATOOLS: A Python Library for Gene Ontology analysis. *Sci Rep* 8, 10872, doi:10.1038/s41598-018-28948-z (2018)

Kruse, F., et al., Tomo-seq: A method to obtain genome-wide expression data with spatial resolution. Methods Cell Biol, 2016. 135: p. 299-307.

Muraro, M. J. et al. A Single-Cell Transcriptome Atlast of the Human Pancreas. *Cell Syst* 3, 385-394 e383, doi: 10.1016/j.cels.2016.09.002 (2016)

Martyn, I., et al., *Self-organization of a human organizer by combined Wnt and Nodal signalling.* Nature, 2018. 558(7708): p. 132-135.

Mendjan S, Mascetti V L, Ortmann D, Ortiz M, Karjosukarso D W, Ng Y, Moreau T, Pedersen R A. (2014) NANOG and CDX2 pattern distinct subtypes of human mesoderm during exit from pluripotency. Cell Stem Cell 4; 15(3):310-325.

Shao, Y., et al., *A pluripotent stem cell-based model for post-implantation human amniotic sac development.* Nat Commun, 2017. 8(1): p. 208.

Simunovic M., Metzger J. J., Etoc F., Yoney A., Ruzo A., Martyn I., Croft G., Brivanlou A. H., Siggia E. D. (2018) bioRxiv 330704; doi: https://doi.org/10.1101/330704

Turner, D. A., et al., *Wnt/beta-catenin and FGF signalling direct the specification and maintenance of a neuromesodermal axial progenitor in ensembles of mouse embryonic stem cells.* Development, 2014. 141(22): p. 4243-53.

Turner, D., et al., *Gastruloids develop the three body axes in the absence of extraembryonic tissues and spatially localised signalling.* bioRxiv, 2017[1]. doi.org/10.1101/104539.

Turner, D., et al., *Anteroposterior polarity and elongation in the absence of extra-embryonic tissues and of spatially localised signalling in gastruloids: mammalian embryonic organoids.* Development, 2017[2]. 144(21): p. 3894-3906.

Schindelin J, Arganda-Carreras I, Frise E, Kaynig V, Longair M, Pietzsch T, Preibisch S, Rueden C, Saalfeld S, Schmid B, Tinevez J Y, White D J, Hartenstein V, Eliceiri K, Tomancak P, Cardona A. (2012) Fiji: an open-source platform for biological-image analysis. Nature Methods 28; 9(7):676-82 van den Brink, S. C., et al., *Symmetry breaking, germ layer specification and axial organisation in aggregates of mouse embryonic stem cells.* Development, 2014. 141(22): p. 4231-42.

Warmflash, A., et al., *A method to recapitulate early embryonic spatial patterning in human embryonic stem cells.* Nat Methods, 2014. 11(8): p. 847-54.

The invention claimed is:

1. A polarised three-dimensional cellular aggregate generated in vitro from one or more human pluripotent stem cells, wherein:

(a) the polarised three-dimensional cellular aggregate comprises
  - i. cells comprising one or more markers characteristic of endodermal cells or derivatives of endodermal cells, wherein the one or more markers comprise CDX2 mRNA or polypeptide,
  - ii. cells comprising one or more markers characteristic of mesodermal cells or derivatives of mesodermal cells, wherein the one or more markers comprise BRA mRNA or polypeptide and
  - iii. cells comprising one or more markers characteristic of ectodermal cells or derivatives of ectodermal cells, wherein the one or more markers comprise SOX2 mRNA or polypeptide;

(b) the polarised three-dimensional cellular aggregate is polarised along an anterior-posterior axis defined by at least an anterior region of cells and a posterior region of cells, wherein the polarised three-dimensional cellular aggregate exhibits spatial collinearity of HOX gene expression along the anterior-posterior axis; wherein the cellular aggregate does not comprise extra-embryonic cells, amnion or yolk sac; wherein the cellular aggregate does not comprise forebrain, midbrain or hindbrain; and wherein all cells of the cellular aggregate are genetically descendants of the one or more human pluripotent stem cells;

(c) the polarised three-dimensional cellular aggregate is present in a culture plate, wherein the culture plate comprises a culture cultured in a medium comprising an activator of Wnt signalling and a Rock inhibitor; and (d) the polarised three-dimensional cellular aggregate does not have an inherent capacity of developing into a human being.

2. A polarised three-dimensional cellular aggregate generated in vitro from one or more human pluripotent stem cells, wherein:

(a) the polarised three-dimensional cellular aggregate comprises cells comprising one or more markers characteristic of primordial germ cells or derivatives of primordial germ cells, wherein the one or more markers comprise SOX17 mRNA or polypeptide;

(b) the polarised three-dimensional cellular aggregate is polarised along an anterior-posterior axis, and wherein the polarised three-dimensional cellular aggregate exhibits spatial collinearity of HOX gene expression along the anterior-posterior axis, wherein the cellular aggregate does not comprise extra-embryonic cells, amnion or yolk sac; wherein the polarized three-dimensional cellular aggregate does not comprise forebrain, midbrain or hindbrain; and wherein all cells of the cellular aggregate are genetically descendants of the one or more human pluripotent stem cells;

(c) the polarised three-dimensional cellular aggregate is present in a culture plate, wherein the culture plate comprises a culture cultured in a medium comprising an activator of Wnt signalling and a Rock inhibitor; and (d) the polarised three-dimensional cellular aggregate does not have an inherent capacity of developing into a human being.

3. A polarised three-dimensional cellular aggregate generated in vitro from one or more human pluripotent stem cells, wherein:

(a) the polarised three-dimensional cellular aggregate comprises i. cells comprising one or more markers characteristic of endodermal cells or derivatives of endodermal cells, wherein the one or more markers comprise CDX2 mRNA or polypeptide, ii. cells comprising one or more markers characteristic of mesodermal cells or derivatives of mesodermal cells, wherein the one or more markers comprise BRA mRNA or polypeptide, iii. cells comprising one or more markers characteristic of ectodermal cells or derivatives of ectodermal cells, wherein the one or more markers comprise SOX2 mRNA or polypeptide; and iv. cells comprising one or more markers characteristic of primordial germ cells or derivatives of primordial germ cells, wherein the one or more markers comprise SOX17 mRNA or polypeptide;

(b) the polarised three-dimensional cellular aggregate is polarised along an anterior-posterior axis, and wherein the polarised three-dimensional cellular aggregate exhibits spatial collinearity of HOX gene expression along an anterior-posterior axis; wherein the cellular aggregate does not comprise extra-embryonic cells, amnion or yolk sac; wherein the cellular aggregate does not comprise forebrain, midbrain or hindbrain, and wherein all cells of the cellular aggregate are genetically descendants of the one or more human pluripotent stem cells;

(c) the polarised three-dimensional cellular aggregate is present in a culture plate, wherein the culture plate comprises a culture cultured in a medium comprising an activator of Wnt signalling and a Rock inhibitor; and (d) the polarised three-dimensional cellular aggregate does not have an inherent capacity of developing into a human being.

4. The polarised three-dimensional cellular aggregate of claim 1, wherein:

(i) the polarised three-dimensional cellular aggregate is polarised along the dorso-ventral axis, wherein the dorsal-ventral axis is defined by at least a dorsal region of cells and a ventral region of cells, wherein the cells of the dorsal region express a higher or lower level of one or more genes than the cells of the ventral region; and/or (ii) the polarised three-dimensional cellular aggregate is polarised along the medio-lateral axis, wherein the medio-lateral axis is defined by at least a medial region of cells and two lateral regions of cells, wherein the cells of the medial region express a higher or lower level of one or more genes than the cells of the lateral regions; and/or (iii) the polarised three-dimensional cellular aggregate is polarised along the left-right axis, wherein the left-right axis is defined by at least a left region of cells and a right region of cells, wherein the cells of the left region express a higher or lower level of one or more genes than the cells of the right region.

5. The polarised three-dimensional cellular aggregate of claim 1, wherein:

(i) the cells of the anterior region express a lower level of one or more genes than the cells of the posterior region, and wherein the one or more genes are selected from BRA, WNT3a, CDX2, CDH2 (N-cadherin), BMP7, CHRD, CYP26A, DAND5, NOTO1, FOXA2, CER1, DLL1, DLL3, LEFTY1, LEFTY2, SHH and PTCH1; and/or (ii) the cells of the anterior region express a higher level of one or more genes than the cells of the posterior region, and wherein the one or more genes are selected from GATA6, HAND2, PRDM1, TBX1, BMP2, CDH3, LHX1, PAX8 and BMP4.

6. The polarised three-dimensional cellular aggregate of claim 1, wherein the polarised three-dimensional cellular aggregate comprises two or more of:

a. a region of cells expressing at least BRA RNA or polypeptide, b. a region of cells expressing at least SOX2 RNA or polypeptide, c. a region of cells expressing at least TBX6 RNA or polypeptide, d. a region of cells expressing at least MEOX1 RNA or polypeptide, e. a region of cells expressing at least MESP2 RNA or polypeptide, f. a region of cells expressing at least TCF15 RNA or polypeptide;

g. a region of cells expressing at least GATA6 RNA or polypeptide; and h. a region of cells expressing at least BMP2 RNA or polypeptide;

wherein two or more of (a)-(h) are in any order along the anterior-posterior axis in the polarised three-dimensional cellular aggregate.

7. The polarised three-dimensional cellular aggregate of claim 1, wherein the anterior-posterior axis has is further defined by a central region of cells between the anterior region of cells and the posterior region of cells, wherein the cells of the central region express a higher or lower level of one or more genes than the cells of the anterior or posterior regions, optionally wherein the cells of the central region express a higher level of one or more genes than the cells of the anterior or posterior regions, and wherein the one or more genes are selected from ALDH1A2, DKK1, MEOX1, MESP1, MESP2, OSR1, PITX2, TCF15, PAX3 and/or SIX1.

8. The polarised three-dimensional cellular aggregate of claim 4, wherein:

(i) the cells of the dorsal region express a lower level of one or more genes than the cells of the ventral region, and wherein the one or more genes are selected from SHH, NODAL, LEFTY1, 2, TBX6 and FLK1 (KDR); and/or (ii) the cells of the dorsal region express a higher level of one or more genes than the cells of the ventral region, and wherein the one or more genes are selected from SOX2, OTX2, IRX3, SOX1, POU3F1, POU3F2 AND PAX6; and/or (iii) the cells of the medial region express a lower level of one or more genes than the cells of the lateral regions, and wherein the one or more genes are selected from OSR1, PECAM, MEOX1, TBX6, PAX2, PAX2, LEFTY1 and PITX2; and/or (iv) the cells of the medial region express a higher level of one or more genes than the cells of the lateral regions, and wherein the one or more genes are selected from SOX1, SOX2, DAND5, CER1, FOXA2, and NOTO1; and/or (v) the cells of the right region express a lower or higher level of one or more genes than the cells of the left region, and wherein the one or more genes are selected from NODAL, LEFTY1, LEFTY2 and PITX2.

9. The polarised three-dimensional cellular aggregate of claim 1, (i) wherein the one or more markers characteristic of endodermal cells or derivatives of endodermal cells are one or more genes the expression of which is characteristic of endodermal cells or derivatives of endodermal cells (i) are selected from GSC, NEDD9, PYY, SHH, SORCS2, CER1, SOX17, FOXA2, TRH1 and FOXA1; or (ii) the one or more genes the expression of which is characteristic of endodermal cells or derivatives of endodermal cells are one or more genes the expression of which is characteristic of mesendodermal cells or derivatives of mesendodermal cells are selected from MIXL1, LEFTY1, LEFTY2, AXIN2, TRH1, NODAL, WNT3a, WMT5a, Dll1 and CDX2.

10. The polarised three-dimensional cellular aggregate of claim 1, wherein the one or more markers characteristic of mesodermal cells or derivatives of mesodermal cells are one or more genes the expression of which is characteristic of mesodermal cells or derivatives of mesodermal cells are selected from MEOX1, OSR1, PAX2, ALDH1A2, MESP1, MESP2, TBX6, TCF15, FLK1 (KDR), and TBX1.

11. The polarised three-dimensional cellular aggregate of claim 1, wherein the one or more markers characteristic of mesodermal cells are one or more genes the expression of which is characteristic of mesodermal cells, and wherein the one or more genes the expression of which is characteristic of mesodermal cells are one or more genes the expression of which is characteristic of axial mesoderm cells, wherein:

(i) the one or more genes the expression of which is characteristic of axial mesoderm cells are selected from BRA, NOTO1 and NOGGIN; or (ii) the one or more genes the expression of which is characteristic of axial mesodermal cells are one or more genes the expression of which is characteristic of paraxial mesoderm cells, wherein the one or more genes the expression of which is characteristic of paraxial mesoderm cells are selected from MEOX1, MSGN1, TBX6, TCF15, MESP1, MESP2, and ALDH1A2.

12. The polarised three-dimensional cellular aggregate of claim 1, wherein either:

(i) the one or more markers characteristic of ectodermal cells or derivatives of ectodermal cells are one or more genes the expression of which is characteristic of ectodermal cells or derivatives of ectodermal cells are selected from OTX2, GBX2, SIX1, SIX3, SOX3, DLX5, EYA2and BARX1.

13. The polarised three-dimensional cellular aggregate of claim 1, wherein:

the one or more markers characteristic of ectodermal cells or derivatives of ectodermal cells are one or more genes the expression of which is characteristic of ectodermal cells or derivatives of ectodermal cells, and wherein the one or more markers characteristic of ectodermal cells or derivatives of ectodermal cells are one or more genes characteristic of neural cells, selected from SOX1, SOX2, SOX3, POU3F1, POU3F2, PAX6, NKX1.2 and ZEB2; and/or the polarised three-dimensional cellular aggregate is elongate along the anterior-posterior axis.

14. The polarised three-dimensional cellular aggregate of claim 1, wherein the polarised three-dimensional cellular aggregate comprises one or more progenitor cells or derivatives of progenitor cells, and wherein the one or more progenitor cells or derivatives of progenitor cells are:

a. haematopoietic progenitor cells and/or derivatives of haematopoietic progenitor cells;

b. cardiac progenitor cells and/or derivatives of cardiac progenitor cells;

c. paraxial mesoderm and/or derivatives of paraxial mesoderm;

d. somites and/or derivatives of somites;

e. neural crest and/or derivatives of neural crest;

f. neural ectoderm and/or derivatives of neural ectoderm;

g. placodal ectoderm and/or derivatives of placodal ectoderm;

h. intermediate mesoderm progenitor cells and/or derivatives of intermediate mesoderm progenitor cells;

i. axial mesoderm progenitor cells;

j. neuromesodermal progenitor cells and/or derivatives of neuromesodermal progenitor cells;

k. lateral plate mesoderm and/or derivatives of lateral plate mesoderm;

l. primordial germ cells and/or derivatives of primordial germ cells;

m. node cells and/or derivatives of node cells; and/or n. endoderm and/or derivatives of endoderm.

15. The polarised three-dimensional cellular aggregate of claim 1, wherein either:

(i) the polarised three-dimensional cellular aggregate is generated in vitro from one or more human embryonic stem cells (ESCs) or the polarised three-dimensional cellular aggregate is generated in vitro from one or more human induced pluripotent stem cells (iPSCs); and/or (ii) the three-dimensional cellular aggregate is generated in vitro from a single pluripotent stem cell.

16. A method for obtaining a polarised three-dimensional cellular aggregate generated in vitro from one or more human pluripotent stem cells, the method comprising:

(a) generating a cell suspension from one or more human pluripotent stem cells, wherein the cell suspension comprises one or more disassociated human pluripotent stem cells;

(b) culturing the cell suspension under conditions that promote the transformation of at least one of the disassociated human pluripotent stem cells into a three-dimensional cellular aggregate; and (c) culturing the three-dimensional cellular aggregate under conditions comprising in a medium comprising an activator of Wnt signalling and a Rock inhibitor that promote the transformation of the three-dimensional cellular aggregate into a polarised three-dimensional cellular aggregate, wherein the activator of Wnt signalling is selected from one or more of a GSK3 inhibitor, CHI99021, WNT3, WNT3a, WNT5, WNT8, and WNT11;

whereby the polarised three-dimensional cellular aggregate is generated which is polarised along an anterior-posterior axis having spatial collinearity of expression of HOX genes along the anterior-posterior axis; and wherein the polarised three-dimensional cellular aggregate comprises:

i. cells comprising one or more markers characteristic of endodermal cells or derivatives of endodermal cells, wherein the one or more markers comprise CDX2 mRNA or polypeptide, ii. cells comprising one or more markers characteristic of mesodermal cells or derivatives of mesodermal cells, wherein the one or more markers comprise BRA mRNA or polypeptide, and iii. cells comprising one or more markers characteristic of ectodermal cells or derivatives of ectodermal cells, wherein the one or more markers comprise SOX2 mRNA or polypeptide.

17. A method for obtaining one or more progenitor cells or derivatives thereof, the method comprising (a) generating a cell suspension from one or more human pluripotent stem cells, wherein the cell suspension comprises one or more disassociated human pluripotent stem cells;

(b) culturing the cell suspension under conditions that promote the transformation of at least one of the disassociated human pluripotent stem cells into a three-dimensional cellular aggregate; and (c) culturing the three-dimensional cellular aggregate under conditions comprising in a medium comprising an activator of Wnt signalling and a Rock inhibitor that promote the transformation of the three-dimensional cellular aggregate into a polarised three-dimensional cellular aggregate:

whereby the polarised three-dimensional cellular aggregate is generated which is polarised along an anterior-posterior axis having spatial collinearity of expression of HOX genes along the anterior-posterior axis; and wherein the polarised three-dimensional cellular aggregate comprises:

i. cells comprising one or more markers characteristic of endodermal cells or derivatives of endodermal cells, wherein the one or more markers comprise CDX2 mRNA or polypeptide, ii. cells comprising one or more markers characteristic of mesodermal cells or derivatives of mesodermal cells, wherein the one or more markers comprise BRA mRNA or polypeptide, and iii. cells comprising one or more markers characteristic of ectodermal cells or derivatives of ectodermal cells, wherein the one or more markers comprise SOX2 mRNA or polypeptide; and (d) culturing the polarised three-dimensional cellular aggregate under conditions that promote the differentiation of one or more cells of the polarised-three dimensional cellular aggregate into progenitor cells or derivatives thereof; whereby one or more progenitor cells or derivatives thereof are generated and wherein the one or more progenitor cells or derivatives thereof are:

a. haematopoietic progenitor cells and/or derivatives thereof;

b. cardiac progenitor cells and/or derivatives thereof;

c. paraxial mesoderm and/or derivatives thereof;

d. somites and/or derivatives thereof;

e. neural crest and/or derivatives thereof;

f. neural ectoderm and/or derivatives thereof;

g. placodal ectoderm and/or derivatives thereof;

h. intermediate mesoderm progenitor cells and/or derivatives thereof;

i. axial mesoderm progenitor cells;

j. neuromesodermal progenitor cells and/or derivatives thereof;

k. lateral plate mesoderm and/or derivatives thereof;

I. primordial germ cells and/or derivatives thereof;

m. node cells and/or derivatives thereof; and/or n. endoderm and/or derivatives thereof.

* * * * *